(12) United States Patent
Suzuki et al.

(10) Patent No.: US 9,247,775 B2
(45) Date of Patent: Feb. 2, 2016

(54) MASK

(75) Inventors: Migaku Suzuki, Tokyo (JP); Yoshio Hirai, Tokyo (JP)

(73) Assignee: DAIO PAPER CORPORATION, Shikokuchuo-shi (JP)

( * ) Notice: Subject to any disclaimer, the term of this patent is extended or adjusted under 35 U.S.C. 154(b) by 352 days.

(21) Appl. No.: 13/356,086

(22) Filed: Jan. 23, 2012

(65) Prior Publication Data
US 2013/0186414 A1      Jul. 25, 2013

(51) Int. Cl.
A62B 18/02      (2006.01)
A42B 1/08       (2006.01)
A41D 13/11      (2006.01)
A61F 9/06       (2006.01)

(52) U.S. Cl.
CPC ............ *A41D 13/1161* (2013.01); *A41D 13/11* (2013.01); *A61F 9/06* (2013.01)

(58) Field of Classification Search
CPC ...................................................... A41D 13/11
USPC ................... 128/846, 857, 863, 206.19, 139, 128/206.12, 201.23, 201.24, 201.25, 128/201.27, 201.28, 201.29, 206.13, 128/206.16, 206.17, 205.25, 206.27, 128/206.21, 206.28; 2/7, 9, 206, 173, 424, 2/2.1, 6, 10, 171, 455, 410, 8.1
See application file for complete search history.

(56) References Cited

U.S. PATENT DOCUMENTS

| | | | | |
|---|---|---|---|---|
| 2,556,589 | A * | 6/1951 | Le Duc | 128/206.12 |
| 2,787,264 | A * | 4/1957 | Thiebault et al. | 128/206.19 |
| 3,288,138 | A * | 11/1966 | Sachs | 128/863 |
| 6,102,040 | A * | 8/2000 | Tayebi et al. | 128/206.24 |
| 6,520,181 | B2 * | 2/2003 | Baumann et al. | 128/206.19 |
| 7,185,653 | B2 | 3/2007 | Lee | |
| 8,146,594 | B2 * | 4/2012 | Bostock et al. | 128/206.12 |
| 8,251,065 | B2 * | 8/2012 | Kim | 128/206.19 |
| 2004/0202700 | A1 * | 10/2004 | Phaneuf et al. | 424/443 |

FOREIGN PATENT DOCUMENTS

| | | |
|---|---|---|
| CN | 1593691 A | 3/2005 |
| CN | 101282852 A | 10/2008 |
| JP | A-10-5360 | 1/1998 |
| JP | A-10-15091 | 1/1998 |

(Continued)

OTHER PUBLICATIONS

Mar. 9, 2015 Office Action issued in Chinese Application No. 201210020658.X.

*Primary Examiner* — Victoria J Hicks
*Assistant Examiner* — Tarla Patel
(74) *Attorney, Agent, or Firm* — Oliff PLC

(57) ABSTRACT

To provide a mask less liable to cause a shift in wearing position. The mask includes a main-body portion for covering a lower face portion of a wearer and a fixation portion, coupled to the main body portion, for fixing the main-body portion to the lower face portion of the wearer. The main-body portion includes: a main-sheet portion; a lower body for holding a lower jaw of the wearer, the lower body being made of a stretchable material and provided across right and left end portions of the main-sheet portion on a lower, inner side of the main-sheet portion; and/or an upper body for holding the nose of the wearer, the upper body being made of a stretchable material and provided across the right and left end portions of the main-sheet portion on an upper, inner side of the main-sheet portion.

20 Claims, 38 Drawing Sheets

(56) References Cited

FOREIGN PATENT DOCUMENTS

| | | |
|---|---|---|
| JP | A-2007-54270 | 3/2007 |
| JP | A-2007-54381 | 3/2007 |
| JP | A-2007-68827 | 3/2007 |
| JP | U-3138154 | 12/2007 |
| JP | A-2008-12248 | 1/2008 |

\* cited by examiner (A)

(B)

(C)

(D)

(A)

(B)

(A)

(B)

(A)

(B)

(A)

(B)

(A)

(B)

(A)

(B)

(A) (B)

(A) (B)

(A) (B)

(A)  (B)

(A)

(B)

(A)

(B)

MASK

TECHNICAL FIELD

The present invention relates to a mask.

BACKGROUND ART

For conventional masks, there have been proposed various methods of causing peripheral portions of a mask to be held in close contact with skin of a wearer for the purpose of preventing leakage of exhaled air and intrusion of outside air.

For example, Patent Document 1 describes a sanitary mask ear-loop cords attached to both right and left side portions of a mask main body, in which an upper portion of the mask main body is once bent downward to an inner side, and then bent again upward to the inner side, and in which a flexible wire is attached to a leading edge of the upper folded portion so that a central part of the leading edge is expanded to enable immovable support of the mask by causing the mask to be held in close contact from a nose part to cheek parts.

Patent Document 2 describes a mask including a main-body portion for covering the face of a wearer, and ear-loop cords attached to the main-body portion, in which auxiliary pieces each made of an air-permeable material are provided on an inner side of the main-body portion so as to be interposed in gaps between the main-body portion and the face of the wearer.

Patent Document 3 describes a three-dimensional mask including a mask main body formed by bonding a pair of right and left non-woven fabric sheets to each other, and ear-loop portions provided on both side portions of the mask main body, the mask main body being horizontally opened at the time of wearing of the three-dimensional mask so that a bonded portion of the non-woven fabric sheets projects forward, in which at least parts of folded-back pieces, which are folded back at a fold portion toward a rear surface side of the mask main body, are bonded to upper portions of the non-woven fabric sheets of the mask main body, the folded-back pieces being horizontally connected to each other and formed to rise at the fold portion from the rear surface side of the mask main body in association with horizontal opening movement of the mask main body.

Patent Document 4 describes a three-dimensional mask including a mask main body having a front-surface-side member made of an air-permeable material, a rear-surface-side member made of an air-permeable material and a convex member including a top, the convex member being sandwiched between the front-surface-side member and the rear-surface-side member, so as to project to the front surface side, and ear-loop portions provided on both sides of the mask main body so as to be engaged with the ears of a wearer, in which the mask main body includes an absence region formed below a lower end portion of the convex member, which is free from the convex member, and in which an elastic member having stretchability is arranged between the front-surface-side member and the rear-surface-side member in a lower end portion of the mask main body, the elastic member shrinking to form a jaw accommodating portion.

Patent Document 5 describes a gathered mask including three-dimensional gathers over an upper edge as well as right and left parts on a rear surface of a mask main body, and a wire provided above the upper part.

Patent Document 6 describes a mask including a nose-portion covering piece and a jaw-portion covering piece which are arranged in an overlapping state on a rear surface of a mask main body formed of a filter member such as non-woven fabric and each of which is made of the same material as that for the mask main body, in which an upper edge portion of the nose-portion covering piece is attached to an upper end portion of the mask main body through intermediation of a linear heat-fused portion curved downward in a circular-arc shape from a central portion in a width direction of the mask main body to both side-end portions, in which a lower edge portion of the jaw-portion covering piece is attached to a lower end portion of the mask main body through intermediation of another linear heat-fused portion curved upward in a circular-arc shape from the central portion in the width direction of the mask main body to both the side-end portions, in which an free-end portion of each of the nose-portion covering piece and the jaw-portion covering piece is formed to be expandable rearward, with the respective heat-fused portions being used as fulcrums, and in which cord attachment jigs are mounted to both the side-end portions of the mask main body so that ear-loop cords are attached to the cord attachment jigs.

Patent Document 7 describes a three-dimensional mask made of non-woven fabric, including a face covering portion and ear-loop portions, in which a V-shaped notch is provided to at least one of an upper side and a lower side of a center of the face covering portion so that the face covering portion is provided with three-dimensional properties by bonding both oblique lines of the notch, in which the face covering portion is formed of a continuous and single non-woven fabric piece, and in which a collar portion jettying upward is provided at a center on an upper side of the face covering portion.

PRIOR ART DOCUMENTS

Patent Documents

[Patent Document 1] JP 10-5360 A (the term "JP XX-XXXXXX A" as used herein means an "unexamined published Japanese patent application")
[Patent Document 2] JP 10-15091 A
[Patent Document 3] JP 2007-54270 A
[Patent Document 4] JP 2007-68827 A
[Patent Document 5] JP 2008-12248 A
[Patent Document 6] JP 3138154 U (Japanese Utility Model Registration No. 3138154)
[Patent Document 7] JP 2007-054381 A

SUMMARY OF THE INVENTION

Subject to be Solved by the Invention

However, as a result of extensive studies on performances of those masks, the inventor of the present invention has found out that a wearing position of each of all the masks is liable to shift during actual wearing. Specifically, the inventor of the present invention has found out that the shift occurs particularly when the jaw moves up and down in accordance with opening and closing of the mouth of a wearer during conversation.

In the masks provided for the purpose of preventing leakage of exhaled air and intrusion of outside air, such a shift of the wearing position is problematic because achievement of the purpose is hindered. Further, also as for masks which are not provided for the purpose of preventing leakage of exhaled air and intrusion of outside air, for example, the shift of the wearing position brings discomfort to the wearer, and hence is problematic.

Therefore, the present invention has an object to provide a mask which is less liable to cause a shift of a wearing position.

As a result of extensive studies for the purpose of achieving the above-mentioned object, the inventor of the present invention completed a mask having a novel structure.

Specifically, the present invention provides a mask according to Items (1) to (20) described below.

(1) A mask, including:
a main-body portion for covering a lower face portion of a wearer including a nose and a mouth; and
at least one fixation portion for fixing the main-body portion to the lower face portion of the wearer, the at least one fixation portion being coupled to the main-body portion,
in which the main-body portion includes:
a main-sheet portion; and
a lower belt-like body for holding a lower jaw of the wearer, the lower belt-like body being made of a band-like stretchable material and provided across both right and left end portions of the main-sheet portion in a lower portion on an inner side of the main-sheet portion, and/or an upper belt-like body for holding the nose of the wearer, the upper belt-like body being made of a band-like stretchable material and provided across both the right and left end portions of the main-sheet portion in an upper portion on the inner side of the main-sheet portion.

(2) A mask according to Item (1) described above,
in which the lower belt-like body and/or the upper belt-like body is provided so as to be positioned between the main-sheet portion and skin of the wearer during wearing.

(3) A mask according to Item (2) described above,
in which the lower belt-like body is provided so as to be held in contact with a face of the wearer, covering a region of the face of the wearer from the lower jaw to both cheeks via a jawbone; and/or the upper belt-like body is provided so as to be held in contact with the face of the wearer, covering a region of the face of the wearer from a nose tip to both the cheeks via wings of the nose.

(4) A mask according to Item (1) described above,
in which an inner surface of the main-sheet portion and the skin of the wearer are out of contact from each other during wearing.

(5) A mask according to Item (4) described above,
in which, during wearing, a shortest distance between the inner surface of the main-sheet portion and a horizontally central, lowermost portion of a part of the nose of the wearer which comes into contact with the main-body portion is 0.5 mm or more.

(6) A mask according to Item (4) described above,
in which, during wearing, a distance between the inner surface of the main-sheet portion and a horizontally central, lowermost portion of an upper lip of the wearer is 3 mm or more.

(7) A mask according to Item (4) described above,
in which, during wearing, a shortest distance between the inner surface of the main-sheet portion and a horizontally central, uppermost portion of a part of a jaw of the wearer which comes into contact with the main-body portion is 0.5 mm or more.

(8) A mask according to Item (4) described above,
in which, during wearing, a distance between the inner surface of the main-sheet portion and a cheek of the wearer is 1 mm or more.

(9) A mask according to Item (1) described above,
in which a maximum stretching rate in a horizontal direction of the at least one of the lower belt-like body and the upper belt-like body is 1.5 or more.

(10) A mask according to Item (1) described above,
in which the main-body portion includes the lower belt-like body, and
in which the lower belt-like body is configured so that an entire lower marginal portion thereof is not coupled to the main-sheet portion and forms a stretchable jaw band to be caught by the lower jaw of the wearer.

(11) A mask according to Item (1) described above,
in which the main-body portion includes the lower belt-like body, and
in which the lower belt-like body is configured so that an entire lower marginal portion or a part of the lower marginal portion thereof is coupled to the main-sheet portion and forms a jaw wrapping pocket for accommodating the lower jaw of the wearer.

(12) A mask according to Item (11) described above,
in which the lower belt-like body is folded back so that a doubled part is formed between the main-sheet portion and the skin of the wearer during wearing.

(13) A mask according to Item (1) described above,
in which the main-body portion includes the lower belt-like body, and
in which a jaw wrapping pocket for accommodating the lower jaw of the wearer is formed of a bag-like member having an opening provided on an upper side thereof, the bag-like member being obtained by coupling the lower belt-like body and a sheet-like object, which is provided on an outer side of the lower belt-like body, to each other at lower edge portions and both right and left sides thereof, the bag-like member being coupled to the main-sheet portion at a portion of the sheet-like object so that the lower belt-like body is positioned in a lower portion on the inner side of the main-sheet portion.

(14) A mask according to Item (11) described above,
in which a depth of the jaw wrapping pocket is 20 mm or more.

(15) A mask according to Item (1) described above,
in which the main-body portion includes the lower belt-like body, and
in which the lower belt-like body includes a slit or a hole so that the lower jaw of the wearer is accommodated in the slit or the hole.

(16) A mask according to Item (1) described above,
in which the main-body portion includes the upper belt-like body, and
in which the upper belt-like body is configured so that an entire upper marginal portion thereof is not coupled to the main-sheet portion and forms a stretchable nose band to be caught by the nose of the wearer.

(17) A mask according to Item (1) described above,
in which the main-body portion includes the upper belt-like body, and
in which the upper belt-like body is configured so that an entire upper marginal portion or a part of the upper marginal portion thereof is coupled to the main-sheet portion and forms a nose wrapping pocket for accommodating the nose of the wearer.

(18) A mask according to Item (17) described above,
in which the upper belt-like body is folded back so that a doubled part is formed between the main-sheet portion and the skin of the wearer during wearing.

(19) A mask according to Item (1) described above,
in which the main-body portion includes the upper belt-like body, and
in which a nose wrapping pocket for accommodating the nose of the wearer is formed of a bag-like member having an opening provided on a lower side thereof, the bag-like member being obtained by coupling the upper belt-like body and a sheet-like object, which is provided on an outer side of the upper belt-like body, to each other at upper edge portions and both right and left sides thereof, the bag-like member being coupled to the main-sheet portion at a portion of the sheet-like object so that the upper belt-like body is positioned in an upper portion on the inner side of the main-sheet portion.

(20) A mask according to Item (17) described above, in which a depth of the nose wrapping pocket is 20 mm or more.

Effect of the Invention

The mask according to the present invention is less liable to cause a shift of wearing positions.

EMBODIMENTS OF THE INVENTION

Hereinafter, a mask of the present invention is described in detail based on preferred embodiments illustrated in the attached drawings. In the specification of the present invention, when the mask of the present invention is actually worn, a side close to skin of a wearer is referred to as "inner" side and a side far therefrom is referred to as "outer" side. In addition, when the mask of the present invention is actually worn, a side corresponding to an upper side of a body of the wearer is referred to as "upper" side and a side corresponding to a lower side thereof is referred to as "lower" side.

Figure 1:
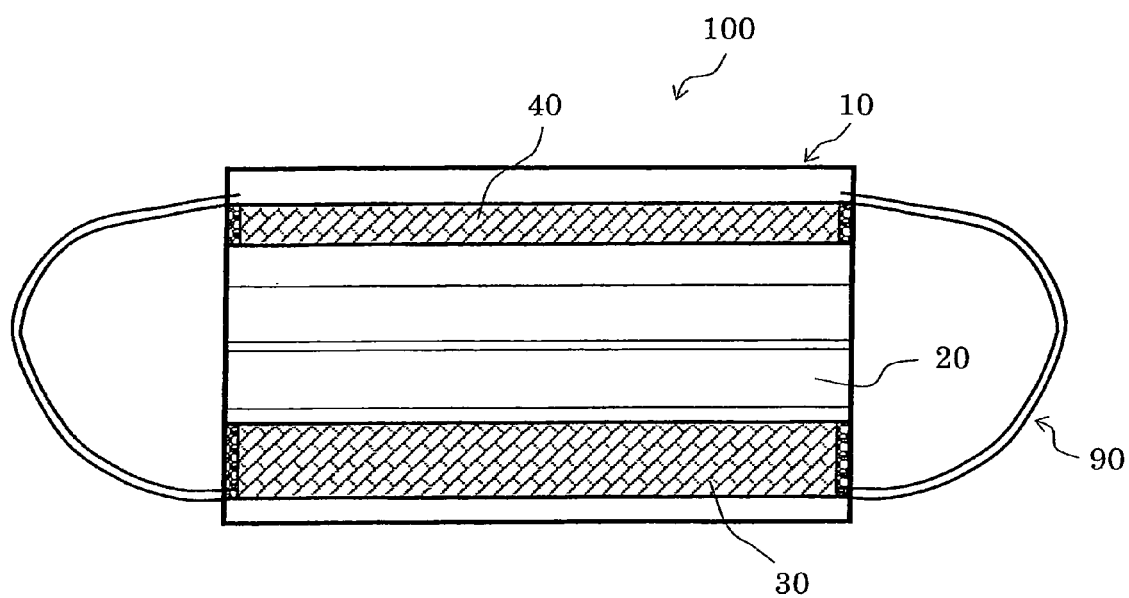
FIG. 1 is a schematic plan view illustrating an example of a mask according to the present invention.

FIG. 1 is a schematic plan view illustrating an example of a mask according to the present invention. Note that, all the plan views of the attached drawings are viewed from the inner side, and an upper side of the mask is positioned on an upper side in illustration of each of the plan views.

A mask 100 according to the present invention basically includes a main-body portion 10 for covering a lower face portion of the wearer including the nose and the mouth and fixation portions 90 coupled to the main-body portion 10, the fixation portions 90 fixing the main-body portion 10 to the lower face portion of the wearer.

The main-body portion 10 includes: a main-sheet portion 20; a lower belt-like body 30 for holding the lower jaw of the wearer, the lower belt-like body 30 being made of a belt-like stretchable material directly coupled to both right and left end portions of the main-sheet portion 20 and provided across both the right and left end portions in a lower portion on the inner side of the main-sheet portion 20; and an upper belt-like body 40 for holding the nose of the wearer, the upper belt-like body 40 being made of a belt-like stretchable material directly coupled to both the right and left end portions of the main-sheet portion 20 and provided across both the right and left end portions in an upper portion on the inner side of the main-sheet portion 20.

The main-body portion 10 of the mask 100 according to the present invention includes both the lower belt-like body 30 and the upper belt-like body 40, but the present invention is not limited thereto. The main-body portion may include only the lower belt-like body, or the main-body portion may include only the upper belt-like body. The case where the main-body portion includes both the lower belt-like body and the upper belt-like body is preferred because a shift of wearing positions is less liable to occur.

The main-sheet portion 20 is not particularly limited. For example, a main-body portion of a conventionally well-known mask can be used as the main-sheet portion 20.

The main-sheet portion 20 includes pleats extending in a horizontal direction. The number of the pleats is not particularly limited. For example, one pleat may be provided or two or more pleats may be provided.

In the present invention, a structure of the main-sheet portion is not particularly limited. For example, the main-sheet portion may have a planar shape free from the pleats. Alternatively, the main-sheet portion may have a three-dimensional structure of projecting outward at a central portion in the horizontal direction.

One of preferred modes of the main-sheet portion 20 is to include a laminated body including an inner-surface sheet, a pathogen inactivating layer, and an outer-surface sheet laminated in the stated order from the wearer side. As described below, it is preferred that the pathogen inactivating layer be made of a plurality of sheet-like materials.

Materials for the inner-surface sheet are not particularly limited. For example, it is possible to employ: non-woven fabrics such as a dry-process non-woven fabric, a wet-process non-woven fabric, a spun-melt non-woven fabric, and a spun-lace non-woven fabric; a chemical fiber textile; and knits. Of those, materials having lower basis weight are preferred because of excellent air-permeability.

In particular, one of preferred modes of the inner-surface sheet is to be made of a porous material. Specific examples of the porous material include: a net-like, mesh-like, or gauze-like non-woven fabric; a film with openings; and a net, a mesh, and laces obtained by interweaving or knitting chemical synthetic filaments. When the porous inner-surface sheet is employed, a contact area against the skin decreases, which provides excellent wearing comfort to the wearer.

Further, another of the preferred modes of the inner-surface sheet is to have a ridge-and-furrow-shaped projection-and-recess structure formed on a surface thereof. In this mode, the contact area against the skin decreases, and the inner-surface sheet has cushioning properties. Thus, what is called a "soft touch" feel can be obtained, which provides excellent wearing comfort to the wearer.

Further, still another of the preferred modes of the inner-surface sheet is to be formed of a film with funnel-like openings as proposed in JP 2002-238946 A by the inventor of the present invention. This mode is advantageous in that exhaled air is dispersed in a distributive manner, and hence the entire surface of a laminated body can be easily and efficiently used.

The inner-surface sheet may be made of a hydrophilic material or a hydrophobic material.

As a material for the inner-surface sheet, there may be used a material that has undergone dirt-proof treatment, antimicrobial treatment, water-repellent treatment, or the like.

Further, it is preferred that the material for the inner-surface sheet be excellent in safety in case of being ingested from the mouth into the body of the wearer.

Still further, it is preferred that the material for the inner-surface sheet does not generate powder dust, dropped waste fiber, and the like, for example, through friction during use.

Yet further, it is preferred that the material for the inner-surface sheet be resistant to stain and adhesion of body fat or cosmetics such as a lipstick owing to contact with the lips of the wearer.

Yet further, it is preferred that the material for the inner-surface sheet be able to prevent growth of pathogens exhaled from the wearer and indigenous bacteria on the surface thereof.

The inner-surface sheet may be arranged over the entire laminated body, or may be arranged at a part of the laminated body, for example, arranged at a part in abutment with a periphery of the lip portion.

Alternatively, the inner-surface sheet may be arranged by being merely laminated on the pathogen inactivating layer, and the surface of the inner-surface sheet and a surface of the pathogen inactivating layer may be integrated with each other by bonding.

When the inner-surface sheet and the pathogen inactivating layer are merely laminated on each other, it is possible to easily practice a mode in which the inner-surface sheet and the pathogen inactivating layer are separated from each other so that the inner-surface sheet is replaceable. In this mode, for example, in a case of using the mask according to the present invention for a long period of time, by replacement of the inner-surface sheet at the time of taking off a mask for dining, bathing, and the like, it is possible to maintain a clean state and provide excellent wearing comfort as an unused product.

Materials for the outer-surface sheet are not particularly limited. For example, it is possible to employ: non-woven fabrics such as a dry-process non-woven fabric, a wet-process non-woven fabric, a spun-melt non-woven fabric, and a spun-lace non-woven fabric; a chemical fiber textile; and knits. Of those, materials having a relatively high density and relatively-fine fineness of the constituent fiber are preferred because the following can be captured: airborne droplets and the like scattered by exhalation of the wearer; and dust and the like carried by inhalation of the wearer.

In particular, a spun-melt non-woven fabric made of synthetic fibers such as PE, PP, PET, EVA, a PE/PP bicomponent fiber, and a PE/PET bicomponent fiber is preferred, and an SMS (spun-bonded layer, melt-blown layer, and spun-bonded layer) non-woven fabric and an SMMS (spun-bonded layer, melt-blown layer, melt-blown layer, and spun-bonded layer) non-woven fabric, which are laminated bodies formed with melt blowing non-woven fabric, are more preferred.

The outer-surface sheet may be made of a hydrophilic material or a hydrophobic material.

As a material for the outer-surface sheet, there may be used a material that has undergone dirt-proof treatment, antimicrobial treatment, water-repellent treatment, or the like.

Further, it is preferred that the material for the outer-surface sheet have a smooth surface so that the surface is resistant to stain even when the surface is touched by the hand at the time of taking off the mask according to the present invention.

Still further, it is preferred that the material for the outer-surface sheet does not generate powder dust, or cause fuzz loss, and the like, for example, through friction during use.

The outer-surface sheet may be arranged over the entire laminated body, or may be arranged at a part of the laminated body.

Alternatively, the outer-surface sheet may be arranged by being merely laminated under the pathogen inactivating layer, and the surface of the outer-surface sheet and the surface of the pathogen inactivating layer may be integrated with each other by bonding.

The pathogen inactivating layer is a layer for inactivating pathogens.

In the present invention, the term "pathogens" collectively refers to microbes, viruses, and the like which cause respiratory diseases such as tuberculosis, influenza, pneumonia, bronchitis, and pharyngitis. Specifically, bacteria, molds, rickettsiae, mites, and viruses can be exemplified.

In the present invention, the term "inactivation" means harmlessness treatment, detoxication, paralyzation, and the like with respect to activities of the pathogens. Examples of specific means for inactivation include filtration removal, adsorptive removal, thermal denaturation, chemical denaturation, and antibody responses.

The structure of the pathogen inactivating layer is not particularly limited as long as a function of inactivating the pathogens is exerted. However, the pathogen inactivating layer is preferred to be made of one or more sheet-like materials, and more preferred to be made of a plurality of sheet-like materials.

In this case, one of preferred modes of the pathogen inactivating layer is that at least one of the plurality of sheet-like materials forming the pathogen inactivating layer is folded. In this mode, a folding rate obtained by dividing an area prior to folding of the folded sheet by an area in a folded state of the sheet is preferred to be 1.5 or more, and more preferred to be 2.0 or more.

The air-permeability of the laminated body is preferred to be larger than those of the lower belt-like body 30 and the upper belt-like body 40. In this case, exhaled air more easily passes the laminated body, with the result that the exhaled air is less liable to leak.

The lower belt-like body 30 is provided in the lower portion on the inner side of the main-sheet portion 20. The lower belt-like body 30 is directly coupled to both the right and left end portions of the main-sheet portion 20 and provided across both the right and left end portions. (Both the right and left end portions are indicated by deep-color cross-hatching.

Hereinafter, in some of other drawings, coupling portions are similarly indicated by deep-color cross-hatching).

The upper belt-like body 40 is provided in the upper portion on the inner side of the main-sheet portion 20. The upper belt-like body 40 is directly coupled to both the right and left end portions of the main-sheet portion 20 and provided across both the right and left end portions.

A method of coupling the lower belt-like body 30 or the upper belt-like body 40 and the main-sheet portion 20 to each other is not particularly limited, and hot melting, using an adhesive, ultrasonic sealing, and heat sealing can be exemplified.

Both the lower belt-like body 30 and the upper belt-like body 40 of the mask 100 are directly coupled to the main-sheet portion 20. However, the present invention is not limited thereto as long as a state in which the lower belt-like body and the upper belt-like body are provided across both the right and left end portions is achieved (for example, refer to FIGS. 12 and 15).

Each of the lower belt-like body 30 and the upper belt-like body 40 is made of a belt-like stretchable material.

Although the stretchable material is not particularly limited, the following three stretchable materials can be exemplified.

(1) Stretchable Material Made of a Filamentary Elastic Body (Elastic Yarn)

Specifically, the following can be exemplified: what is called a tape-like or tubular rubber band obtained by kitting or weaving elastic yarns such as a rubber yarn and polyurethane filaments; a stretchable knit or textile obtained by interknitting or interweaving an elastic yarn and synthetic filaments such as nylon filaments and polyester filaments; and materials stretchable along with deformation of composition, such as a stretchable bandage, a tubular bandage, and a stretchable supporter which are obtained by forming an elastic yarn and a spun yarn into a net-like shape or additionally into a tubular shape. Specifically, a stretchable bandage obtained by interknitting urethane filaments and a cotton yarn (more specifically, stretchable bandage manufactured by Hakujuji Co., ltd.) can be exemplified.

(2) Stretchable Films

Specifically, the followings can be exemplified: synthetic resin films such as a polyurethane film, an ethylene-vinyl acetate copolymer (EVA) film, a styrene-ethylene-butylene-styrene (SEBS) copolymer film, and a styrene-butadiene rubber (SBR) film; and synthetic non-woven fabrics such as a polyurethane non-woven fabric. The stretchable films include a stretchable film having a constant stretchability in any direction, a stretchable film having a stretchability only in one direction, and a stretchable film having stretchabilities different from each other between one direction and another direction.

(3) Laminated Body Made of Non-Woven Fabrics and the Stretchable Material of Item (1) Above or the Stretchable Films of Item (2) Above Specifically, the followings can be exemplified: a laminated body obtained by bonding two non-woven fabric pieces with a bonding agent over and beneath a plurality of elastic yarns, which are arrayed in parallel and extended; and a laminated body formed of a SEBS film and a non-woven fabric having a high stretchability in one direction (stretchability in the one direction is higher than a stretchability in the direction orthogonal to the one direction). More specific examples of such laminated bodies include FlexAire 541 Elastic Laminate manufactured by Tredegar Corporation in the U.S., which is a stretchable material having a uni-directional extensibility.

Stretchabilities in the horizontal direction of the lower belt-like body and the upper belt-like body of the mask according to the present invention have an influence on prevention of a shift of wearing positions of the mask. Thus, it is preferred to employ a stretchable material which easily stretches rightward and leftward with a low tension, and less deforms in the width direction, and whose stretchability in the one direction is higher than a stretchability in the direction orthogonal to the one direction.

The stretchable material for each of the lower belt-like body 30 and the upper belt-like body 40 has a belt-like shape.

In the present invention, the expression "belt-like" means that a horizontal length is longer than a vertical length and that a length (thickness) in a front-to-rear direction is rather shorter (smaller) than those lengths.

Figure 2:
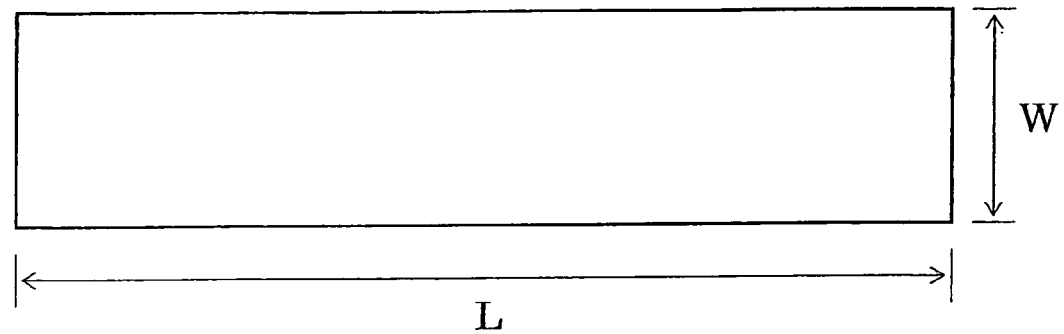
FIG. 2 is a schematic plan view illustrating an example of a belt-like stretchable material.

FIG. 2 is a schematic plan view illustrating an example of the belt-like stretchable material.

As illustrated in FIG. 2, a horizontal length L is longer than a vertical length W in the belt-like stretchable material. A ratio of the horizontal length L to the vertical length W (L/W) is preferred to be 1.5 or more.

Figure 3:
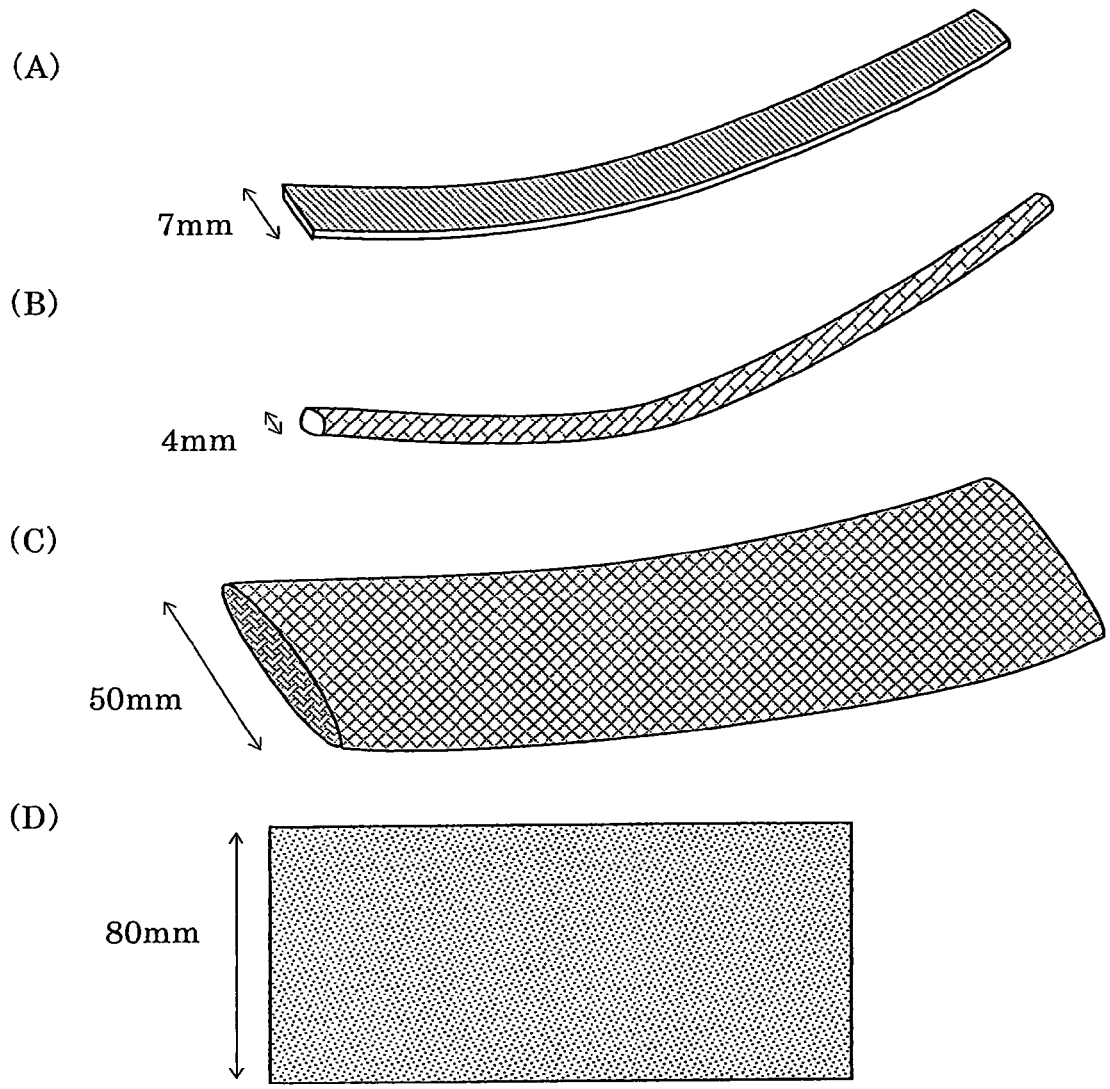
FIGS. 3A to 3D are schematic views illustrating various examples of the belt-like stretchable material.

FIGS. 3A to 3D are schematic views illustrating various examples of the belt-like stretchable material. FIGS. 3A, 3B, and 3C are perspective views, and FIG. 3D is a plan view. Note that, all the numerical values representing vertical lengths illustrated in FIGS. 3A to 3D are merely examples, and hence the present invention is not limited to those numerical values.

The belt-like stretchable material illustrated in FIG. 3A is a plain-woven rubber cord. Examples of the rubber cord include a rubber cord the same as that used for the waist portion of an underwear.

The belt-like stretchable material illustrated in FIG. 3B is obtained by interknitting polyurethane filaments and woolly nylon filaments into a cord-like shape.

The belt-like stretchable material illustrated in FIG. 3C is a tubular knit bandage. Examples of the tubular knit bandage include a tubular knit bandage the same as that used for stretchably covering the elbow, the knee, and the like, and a tubular knit bandage the same as that used as a headband.

The belt-like stretchable material illustrated in FIG. 3D is obtained by cutting a sheet of the stretchable films into a rectangular shape.

When the belt-like stretchable member is used as the lower belt-like body or the upper belt-like body, a maximum stretching rate in the horizontal direction of the belt-like stretchable member (rate of a maximum value of a length of restorative tension with respect to a value of a length in a state without tension) is preferred to be 1.5 or more.

When the mask according to the present invention is worn, normally, the lower belt-like body and the upper belt-like body are preferred not to be used under a tension of the maximum stretching rate but to be used under a tension of a stretching rate (rate of a length in a state under tension with respect to a length in the state without tension) lower than the maximum stretching rate. For example, the mask is used with a stretching rate of approximately 1.3 set with respect to a maximum stretching rate of 1.5, or with a stretching of approximately 1.5 set with respect to a maximum stretching rate of 2.0.

The lower belt-like body 30 holds the lower jaw of the wearer during wearing.

The entire lower marginal portion of the lower belt-like body 30 is not coupled to the main-sheet portion 20. Thus, the lower belt-like body 30 serves as a stretchable jaw band to be caught by the lower jaw of the wearer. During wearing, a central portion of the lower belt-like body 30 is pulled inward (to the wearer's side) and slightly downward so as to be positioned on a lower side (throat side) with respect to a leading end portion of the lower jaw. After that, the pulling of the central portion of the lower belt-like body 30 is stopped. In this way, the lower belt-like body 30 under tension holds the lower jaw by being caught by the lower side (throat side) with respect to the leading end portion of the lower jaw. As a result, the main-body portion 10 is fixed to the lower face portion of the wearer synergistically with an action of the fixation portions 90.

Note that, a surface of the lower belt-like body 30 which comes into contact with the lower jaw of the wearer may be a surface illustrated in FIG. 1, or an unillustrated surface on a rear side of the illustrated surface. Further, for example, at the time of fixation, the lower belt-like body 30 may be appropriately twisted in conformity with a shape of the jaw of the wearer and the like.

A vertical length of the stretchable jaw band is preferred to be 10 mm or more. When the vertical length is 15 mm or more, a shift of wearing positions is less liable to occur.

The upper belt-like body 40 holds the nose of the wearer during wearing.

The entire upper marginal portion of the upper belt-like body 40 is not coupled to the main-sheet portion 20. Thus, the upper belt-like body 40 serves as a stretchable nose band to be caught by the nose of the wearer. During wearing, a central portion of the upper belt-like body 40 is pulled inward (to the wearer's side) and slightly upward so as to be positioned on an upper side with respect to a nose tip. After that, the pulling of the central portion of the upper belt-like body 40 is stopped. In this way, the upper belt-like body 40 under tension holds the nose by being caught by the nose tip or a nose bridge. As a result, the main-body portion 10 is fixed to the lower face portion of the wearer synergistically with the action of the fixation portions 90.

Note that, a surface of the upper belt-like body 40 which comes into contact with the nose of the wearer may be a surface illustrated in FIG. 1, or an unillustrated surface on the rear side of the illustrated surface. Further, for example, at the time of fixation, the upper belt-like body 40 may be appropriately twisted in conformity with a shape of the nose of the wearer and the like.

A vertical length of the stretchable nose band is preferred to be 2 mm or more. When the vertical length is 5 mm or more, a shift of wearing positions is less liable to occur.

The main-body portion 10 of the mask 100 according to the present invention may include other members than the main-sheet portion 20, the lower belt-like body 30, and the upper belt-like body 40.

The fixation portions 90 are coupled to the main-body portion 10, and fix the main-body portion 10 to the lower face portion of the wearer.

Each of the fixation portions 90 is made of a looped stretchable material so as to be looped around each ear of the wearer. The stretchable material is not particularly limited, and an interwoven belt made of a rubber yarn and cotton, an interknitted net made of urethane filaments and polyester filaments, a woolly nylon knitted in a tubular shape, and a stretchable non-woven fabric can be exemplified.

In particular, as proposed in JP 6-328600 A and JP 7-252762 A by the inventor of the present invention, the fixation portion 90 is preferred to be formed by providing slits or cutouts to a composite elastic body having a uni-directional extensibility, and is more preferred to be formed by providing slits or cutouts to a composite elastic body having a uni-directional extensibility, the composite elastic body being formed by laminating a non-woven fabric piece(s) on one or both surfaces of an elastomer film. In this case, the main-body portion can be stably fixed during wearing, and in addition, traces are less liable to be left on the skin of the wearer.

In the present invention, the materials for the fixation portions are not limited to the looped stretchable material. Specifically, the followings can be exemplified: two cords provided respectively on both right and left sides of the main-body portion so as to be looped around the ears of the wearer by being tied to each other; structural bodies each designed like a temple of glasses so as to be hooked to the ears of the wearer from above; and a looped headband to be looped around the head of the wearer, which is similar to that of an eye bandage.

The mask 100 according to the present invention can be obtained by uniting (bonding) the above-mentioned various members. The uniting method is not particularly limited, and the followings can be exemplified: sewing with use of a sewing thread and the like; adhesion by hot melting and the like; and welding by heat sealing, ultrasonic sealing, and the like. In a case of sewing with use of a sewing thread, sealing treatment with use of a resin, a tackifier tape, and the like can be performed on seams.

As described above, the main-body portion 10 of the mask 100 according to the present invention includes the lower belt-like body 30 and/or the upper belt-like body 40. Thus, for example, even when the jaw moves up and down in accordance with opening and closing of the mouth of the wearer during conversation, a shift of wearing positions is less liable to occur.

More detailed description is made of the lower belt-like body and the upper belt-like body.

Figure 4:
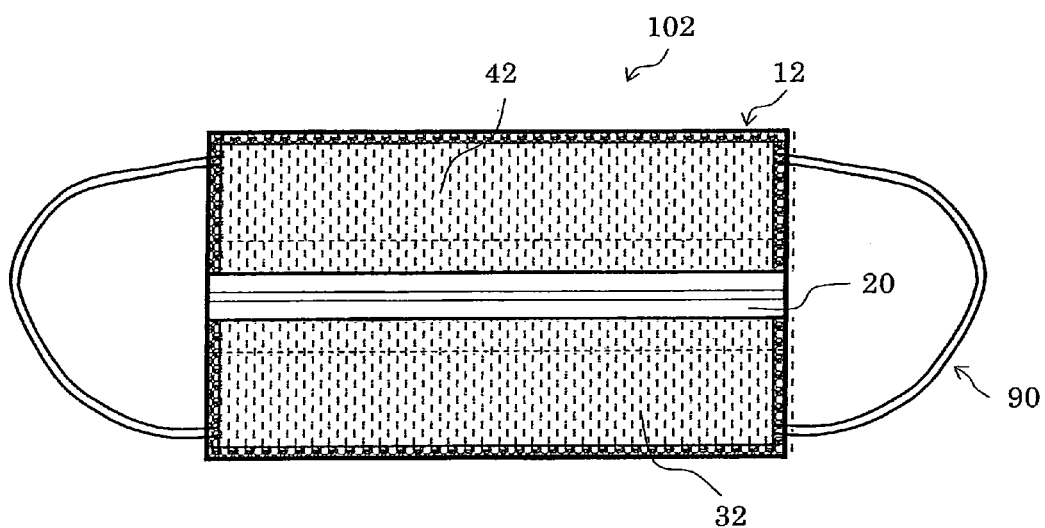
FIG. 4 is a schematic plan view illustrating another example of the mask according to the present invention.

FIG. 4 is a schematic plan view illustrating another example of the mask according to the present invention.

A mask 102 illustrated in FIG. 4 is basically the same as the mask 100 except that a main-sheet portion 20 of a main-body portion 12 is provided with a lower belt-like body 32 and an upper belt-like body 42 instead of the lower belt-like body 30 and the upper belt-like body 40.

Although the lower belt-like body 32 is basically the same as the lower belt-like body 30, not only both right and left end portions of the lower belt-like body 32 but also the entire lower marginal portion thereof is coupled to the main-sheet portion 20. In this way, the lower belt-like body 32 forms a jaw wrapping pocket for accommodating the lower jaw of the wearer. During wearing, a central portion of the lower belt-like body 32 is pulled inward (to the wearer's side) and slightly downward so that the lower jaw is accommodated in a space formed with use of the lower belt-like body 32. After that, the pulling of the central portion of the lower belt-like body 32 is stopped. In this way, the lower belt-like body 32 under tension holds the lower jaw by being caught by the lower side (throat side) with respect to the leading end portion of the lower jaw. As a result, the main-body portion 12 is fixed to the lower face portion of the wearer synergistically with an action of the fixation portions 90.

Note that, a surface of the lower belt-like body 32 which comes into contact with the lower jaw of the wearer is an unillustrated surface on a rear side of the surface illustrated in FIG. 4.

In the lower belt-like body 32, the entire lower marginal portion thereof is also coupled to the main-sheet portion 20, but the present invention is not limited thereto. For example, the mask according to the present invention may be used in a mode that only a part of the lower marginal portion of the lower belt-like body is coupled to the main-sheet portion.

A depth (maximum value of the vertical length) of the jaw wrapping pocket is preferred to be 20 mm or more. When the depth is 20 mm or more, a shift of wearing positions is less liable to occur.

Although the upper belt-like body 42 is basically the same as the upper belt-like body 40, not only both right and left end portions of the upper belt-like body 42 but also the entire upper marginal portion thereof is coupled to the main-sheet portion 20. In this way, the upper belt-like body 42 together with the main-sheet portion 20 forms a nose wrapping pocket for accommodating the nose of the wearer. During wearing, a central portion of the upper belt-like body 42 is pulled inward (to the wearer's side) and slightly upward so that the nose is accommodated in a space formed with use of the upper belt-like body 42. After that, the pulling of the central portion of the upper belt-like body 42 is stopped. In this way, the upper belt-like body 42 under tension holds the nose by being caught by the nose tip or the nose bridge. As a result, the main-body portion 12 is fixed to the lower face portion of the wearer synergistically with an action of the fixation portions 90.

Note that, a surface of the upper belt-like body 42 which comes into contact with the nose of the wearer is an unillustrated surface on a rear side of the surface illustrated in FIG. 4.

In the upper belt-like body 42, the entire upper marginal portion thereof is also coupled to the main-sheet portion 20, but the present invention is not limited thereto. For example, the mask according to the present invention may be used in a mode that only a part of the upper marginal portion of the upper belt-like body is coupled to the main-sheet portion.

A depth (maximum value of the vertical length) of the nose wrapping pocket is preferred to be 20 mm or more. When the depth is 20 mm or more, a shift of wearing positions is less liable to occur.

As described above, only both right and left end portions of each of the lower belt-like body and the upper belt-like body may be coupled to the main-sheet portion (mode of the stretchable jaw band and the stretchable nose band illustrated in FIG. 1). Alternatively, a part or the entirety of the respective lower and upper marginal portions of each of the lower belt-like body and the upper belt-like body may be coupled to the main-sheet portion (mode of the jaw wrapping pocket and the nose wrapping pocket illustrated in FIG. 4).

Description is made of states of the lower belt-like body, the upper belt-like body, and the main-sheet portion during wearing.

FIGS. 5A to 5D are schematic views each illustrating the state of the lower belt-like body, the upper belt-like body, and the main-sheet portion during wearing.

Figure 5:
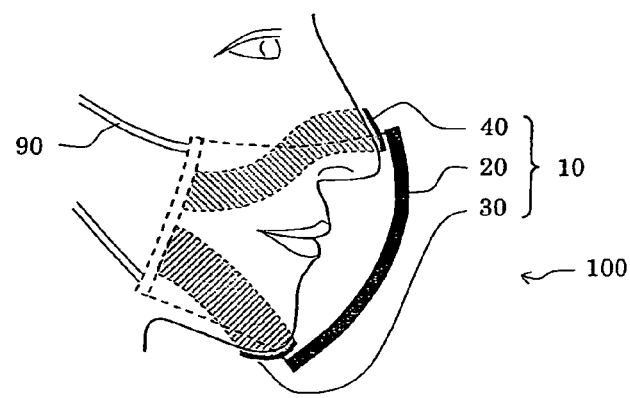
FIGS. 5A to 5D are schematic views each illustrating a state of a lower belt-like body, an upper belt-like body, and a main-sheet portion during wearing.
Figure 5:
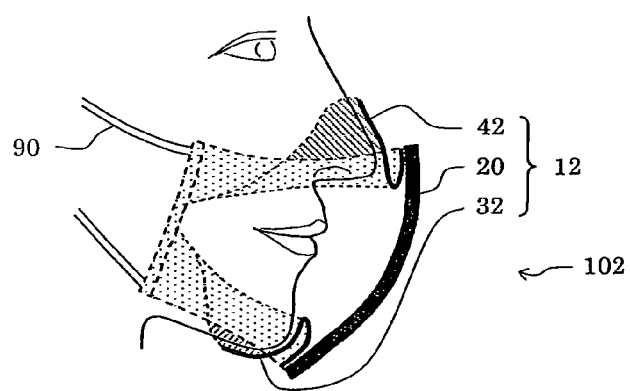
Figure 5:
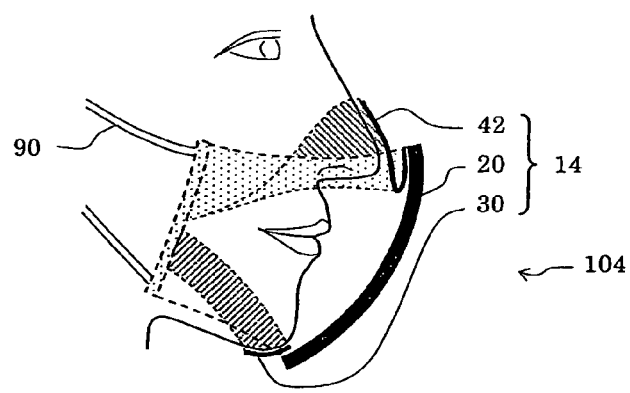
Figure 5:
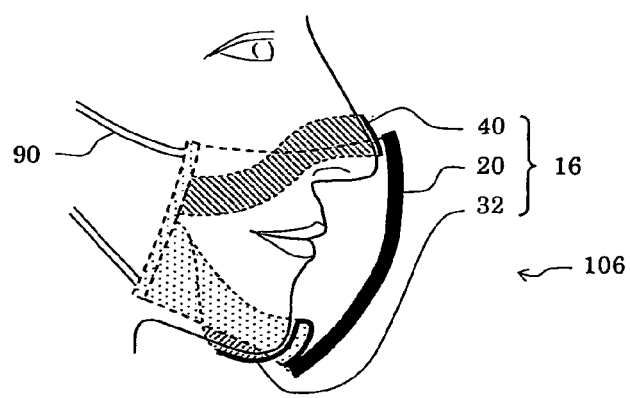

FIG. 5A illustrates a state of wearing the mask 100 illustrated in FIG. 1. The lower belt-like body 30 serves as the stretchable jaw band, and holds the lower jaw of the wearer by being caught by the lower jaw. Further, the upper belt-like body 40 serves as the stretchable nose band, and holds the nose of the wearer by being caught by the nose.

The following can be exemplified as a method for achieving the state illustrated in FIG. 5A: using a stretchable bandage as a stretchable material for both the stretchable jaw band and the stretchable nose band, the stretchable bandage being obtained by interweaving urethane filaments and a cotton yarn (such as a stretchable bandage manufactured by Hakujuji Co., Ltd.); and setting the vertical length of each of the stretchable jaw band and the stretchable nose band to 30 mm.

Further, as illustrated in FIG. 5A, by existing (being interposed) between the main-sheet portion 20 and the skin of the wearer, the lower belt-like body 30 and the upper belt-like body 40 function to prevent contact of an inner surface of the main-sheet portion 20 and the skin of the wearer.

FIG. 5B illustrates a state of wearing the mask 102 illustrated in FIG. 4. The lower belt-like body 32 forms the jaw wrapping pocket, and holds the lower jaw of the wearer by covering a part of the face from the entire lower jaw to both the cheeks. Further, the upper belt-like body 42 forms the nose wrapping pocket, and holds the nose of the wearer by covering a part of the face from the entire nose to both the cheeks.

The following can be exemplified as a method for achieving the state illustrated in FIG. 5B: using a stretchable material having a uni-directional extensibility (such as FlexAire 541 Elastic Laminate manufactured by Tredegar Corporation in the U.S.) as a stretchable material for both the jaw wrapping pocket and the nose wrapping pocket; and setting the depth of each of the jaw wrapping pocket and the nose wrapping pocket to 50 mm.

Further, as illustrated in FIG. 5B, by existing (being interposed) between the main-sheet portion 20 and the skin of the wearer, the lower belt-like body 32 and the upper belt-like body 42 function to prevent contact of the inner surface of the main-sheet portion 20 to the skin of the wearer. Thus, in FIG. 5B, the inner surface of the main-sheet portion 20 and the skin of the wearer are out of contact with each other. In this mode, for example, even when the jaw moves up and down in accordance with opening and closing of the mouth of the wearer during conversation, the movement is less liable to be transmitted to the main-sheet portion 20. Thus, a shift of wearing positions is much less liable to occur.

The following mode can be exemplified as a measure for preventing contact of the inner surface of the main-sheet portion 20 to the skin of the wearer as described above: employing a structure for accommodating the lower jaw of the wearer under a state in which the lower belt-like body 32 is folded back at a position above a coupling portion of the lower marginal portion thereof with respect to the main-sheet portion 20; and employing a structure for accommodating the nose of the wearer under a state in which the upper belt-like body 42 is folded back at a position below a coupling portion of the upper marginal portion thereof with respect to the main-sheet portion 20. In this mode, at least by an amount corresponding to a thickness of the folded-back portion of each of the lower belt-like body 32 and the upper belt-like body 42, a degree by which the inner surface of the main-sheet portion 20 and the skin of the wearer are spaced apart from each other further increases.

FIG. 5C illustrates a state of wearing a mask 104. The mask 104 is basically the same as the mask 100 except that a main-sheet portion 20 of a main-body portion 14 is provided with the upper belt-like body 42 the same as that of the mask 102 instead of the upper belt-like body 40.

The lower belt-like body 30 serves as the stretchable jaw band, and holds the lower jaw of the wearer by being caught by the lower jaw. Further, the upper belt-like body 42 forms the nose wrapping pocket, and holds the nose of the wearer by covering a part of the face from the entire nose to both the cheeks.

Further, as illustrated in FIG. 5C, by existing (being interposed) between the main-sheet portion 20 and the skin of the wearer, the lower belt-like body 30 and the upper belt-like body 42 function to prevent contact of an inner surface of the main-sheet portion 20 to the skin of the wearer.

FIG. 5D illustrates a state of wearing a mask 106. The mask 106 is basically the same as the mask 100 except that a main-sheet portion 20 of a main-body portion 16 is provided with the lower belt-like body 32 the same as that of the mask 102 instead of the lower belt-like body 30.

The lower belt-like body 32 serves as the jaw wrapping pocket, and holds the lower jaw of the wearer by covering a part of the face from the entire lower jaw to both the cheeks. Further, the upper belt-like body 40 forms the stretchable nose band, and holds the nose of the wearer by being caught by the nose.

Further, as illustrated in FIG. 5D, by existing (being interposed) between the main-sheet portion 20 and the skin of the wearer, the lower belt-like body 32 and the upper belt-like body 40 function to prevent contact of an inner surface of the main-sheet portion 20 to the skin of the wearer.

Further, description is made of deformed states of the lower belt-like body and the upper belt-like body by way of various examples of the upper belt-like body.

Figure 6:
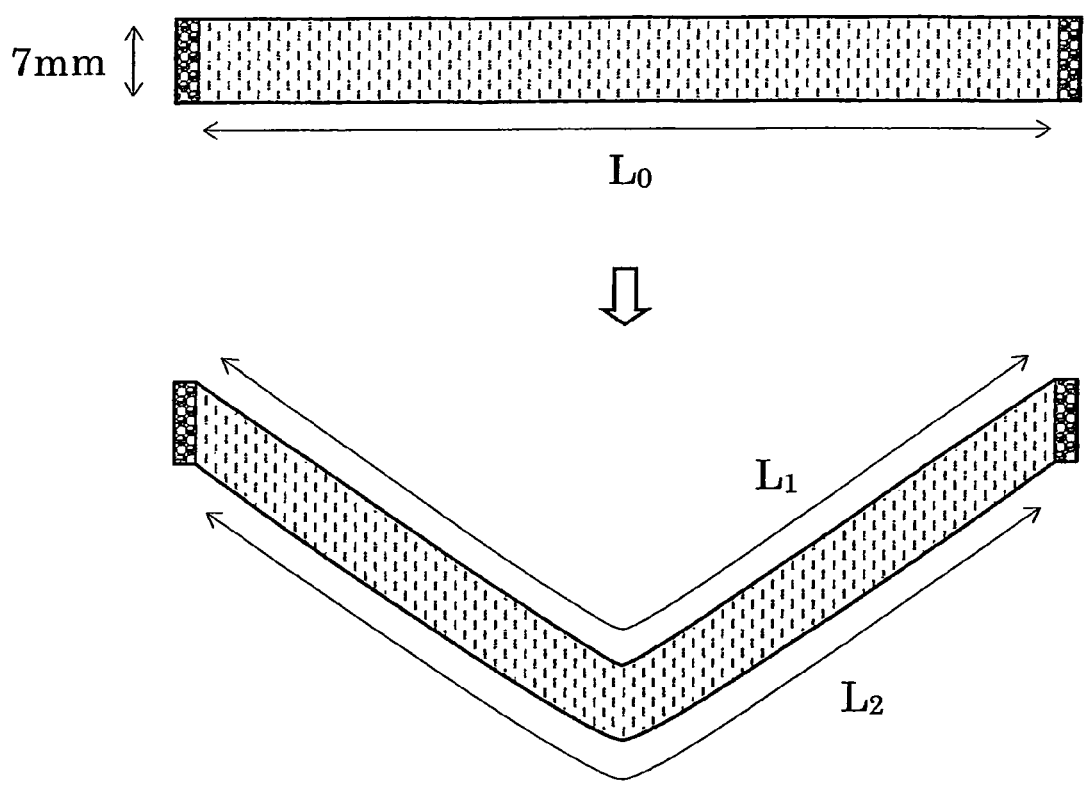
FIG. 6 is a schematic plan view of an upper belt-like body in which only both right and left end portions are to be directly coupled to the main-sheet portion.

FIG. 6 is a schematic plan view of an upper belt-like body in which only both right and left end portions are to be directly coupled to the main-sheet portion.

As illustrated in an upper part of FIG. 6, a horizontal length of the upper belt-like body is $L_0$, and a vertical length thereof (for example, 7 mm) is rather shorter than the horizontal length $L_0$.

By pinching and pulling downward a central portion in the horizontal direction of the upper belt-like body with fingers, as illustrated in a lower part of FIG. 6, a horizontal length of an upper edge portion becomes $L_1$, and a horizontal length of a lower edge portion becomes $L_2$. In this mode, the vertical length is relatively rather short, and hence $L_1$ and $L_2$ are substantially equal to each other.

Figure 7:
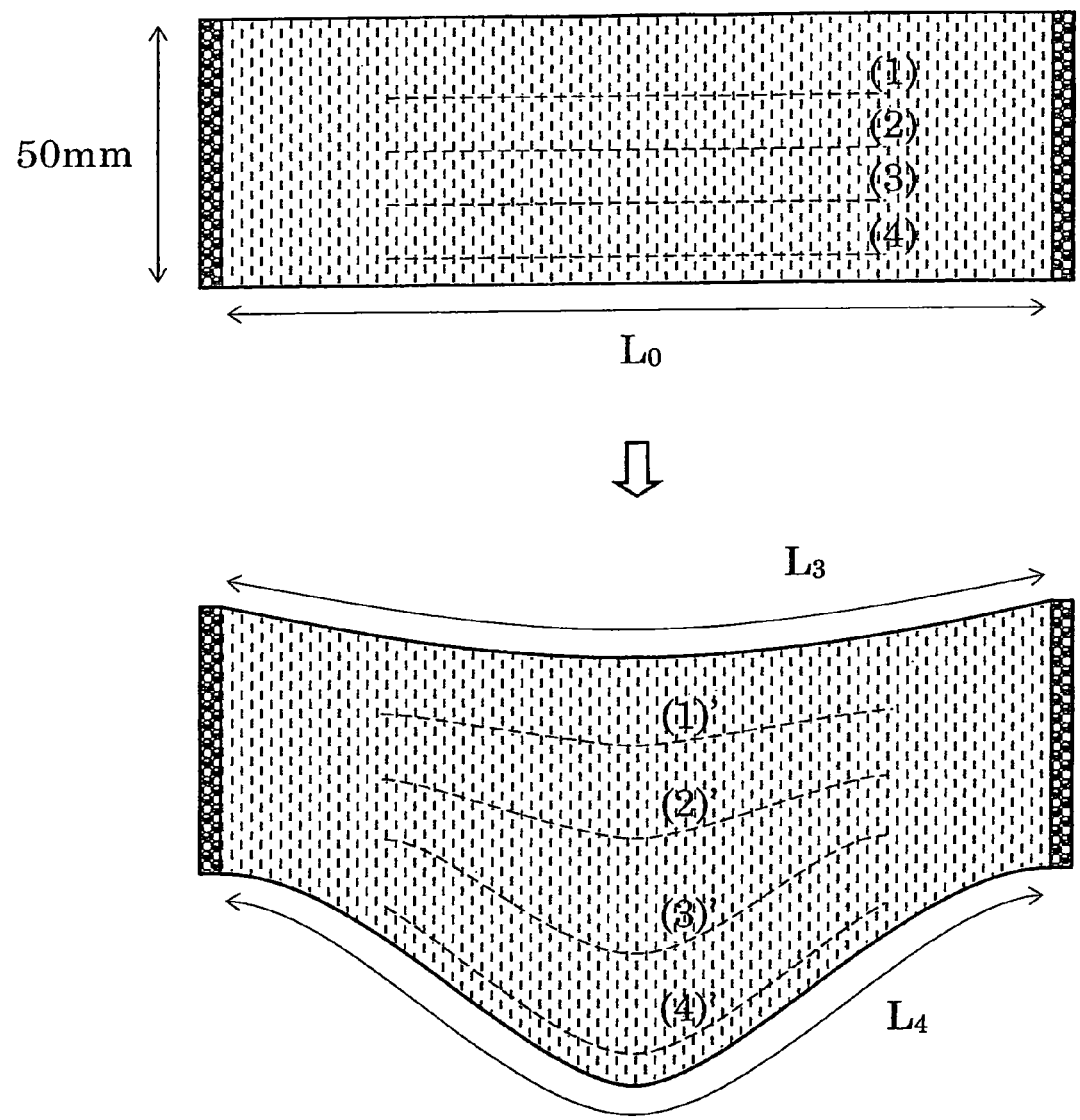
FIG. 7 is a schematic plan view of another upper belt-like body in which only both right and left end portions are to be directly coupled to the main-sheet portion.

FIG. 7 is a schematic plan view of another upper belt-like body in which only both right and left end portions are to be directly coupled to the main-sheet portion.

As illustrated in an upper part of FIG. 7, a horizontal length of the upper belt-like body is $L_0$, and a vertical length thereof (for example, 50 mm) is shorter than the horizontal length $L_0$ but relatively wide.

By pinching and pulling downward a vicinity of a lower edge portion of a central portion in the horizontal direction of the upper belt-like body with fingers, as illustrated in a lower part of FIG. 7, a horizontal length of an upper edge portion becomes $L_3$, and a horizontal length of the lower edge portion becomes $L_4$. In this mode, the vertical length is relatively rather long, and hence a vicinity of the pinched lower edge portion and a vicinity of the upper edge portion are different from each other in deformed state. Specifically, $L_4$ is rather longer than and $L_3$. Further, with regard to a deformed state of a part between the upper edge portion and the lower edge portion, a deformed rate on a lower side is higher than that on an upper side. Specifically, although pre-deformation lengths of parts (1), (2), (3), and (4) are equal to each other, with regard to post-deformation lengths of parts (1)', (2)', (3)', and (4)' corresponding respectively to those parts, the following relation is established: $(1)' < (2)' < (3)' < (4)'$.

The upper belt-like body as illustrated in FIGS. 6 and 7 is provided to serve as the stretchable nose band. In the present invention, materials, shapes, and the like of such a stretchable nose band and a stretchable jaw band are determined in consideration of the deformed states as described above.

Figure 8:
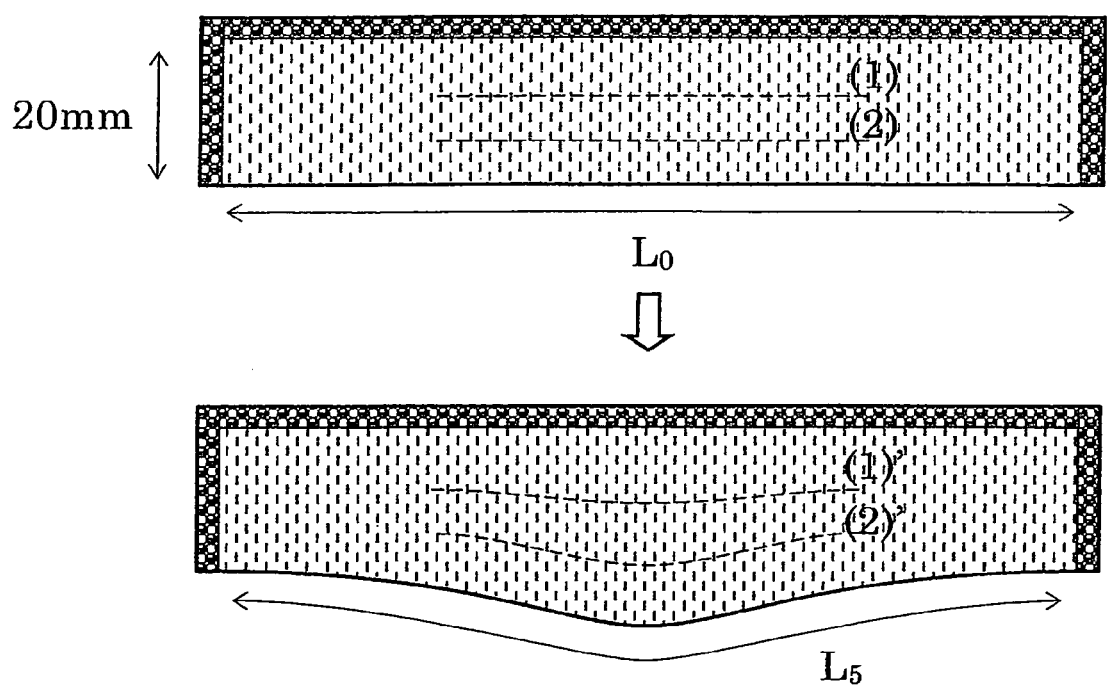
FIG. 8 is a schematic plan view of upper belt-like portion in which both right and left end portions and the entire upper edge portion are to be directly coupled to the main-sheet portion.

FIG. 8 is a schematic plan view of still another upper belt-like portion in which both right and left end portions and the entire upper edge portion are to be directly coupled to the main-sheet portion.

As illustrated in an upper part of FIG. 8, a horizontal length of the upper belt-like body is $L_0$, and a vertical length thereof (except the length of a part of being coupled to the main-sheet portion; hereinafter, also referred to as "depth") (for example, 20 mm) is shorter than the horizontal length $L_0$.

Even by pinching and pulling downward a vicinity of a lower edge portion of a central portion in the horizontal direction of the upper belt-like body with fingers, as illustrated in a lower part of FIG. 8, a horizontal length of the upper edge portion remains as $L_0$ because the upper edge portion is fixed. Meanwhile, a horizontal length of the lower edge portion becomes $L_5$, which is longer than $L_0$. Further, with regard to a deformed state of a part between the upper edge portion and the lower edge portion, a deformed rate on a lower side is higher than that on an upper side. Specifically, although pre-deformation lengths of parts (1) and (2) are equal to each other, with regard to post-deformation lengths of parts (1)' and (2)' corresponding respectively to those parts, the following relation is established: (1)'<(2)'.

In this mode, three sides of both right and left ends and the upper edge portion of the upper belt-like body are fixed to the main-sheet portion, and hence stretching properties are poor in comparison with the original stretchability of the stretchable material.

Figure 9:
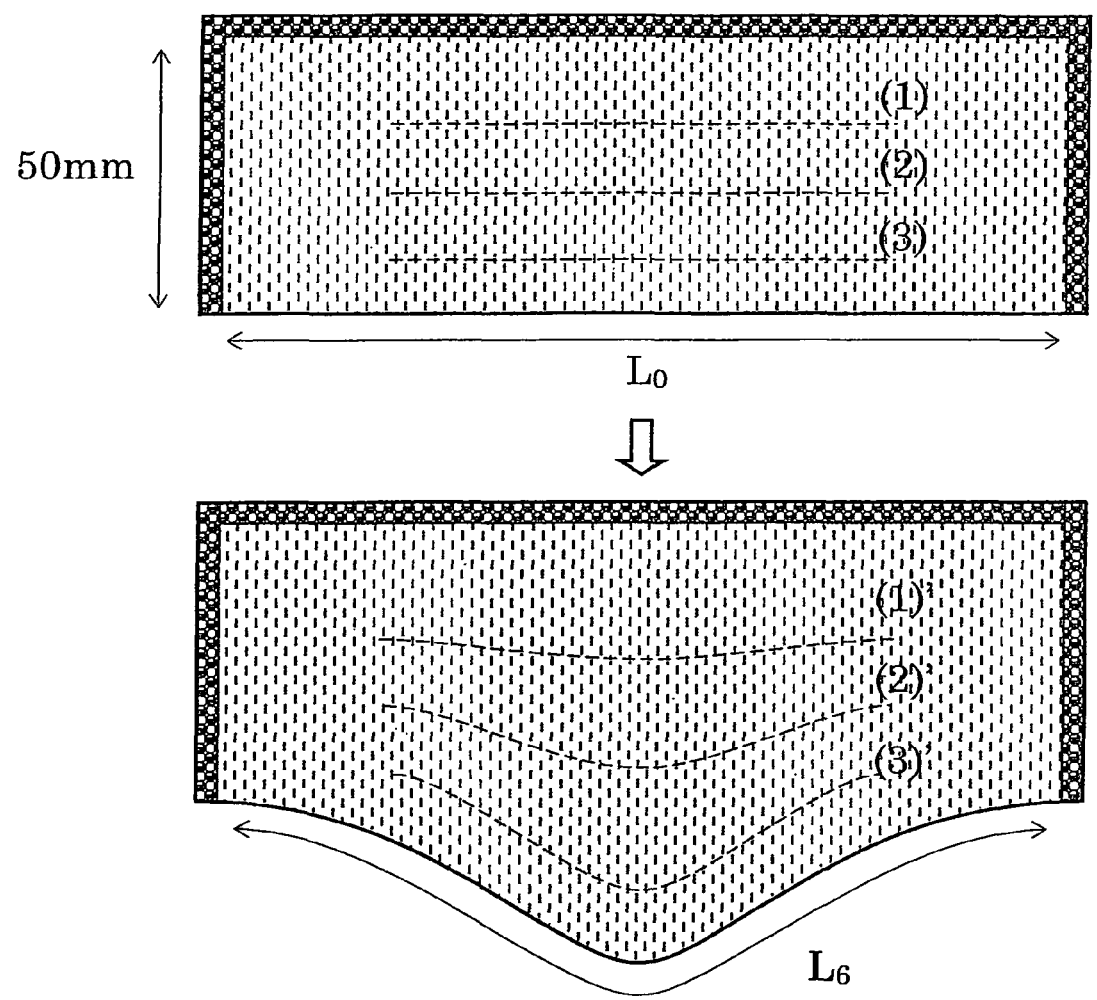
FIG. 9 is a schematic plan view of another upper belt-like portion in which both right and left end portions and the entire upper edge portion are to be directly coupled to the main-sheet portion.

FIG. 9 is a schematic plan view of yet another upper belt-like portion in which both right and left end portions and the entire upper edge portion are to be directly coupled to the main-sheet portion.

As illustrated in an upper part of FIG. 9, a horizontal length of the upper belt-like body is $L_0$, and a vertical length thereof (for example, 50 mm) is shorter than the horizontal length $L_0$ and longer than that of the upper belt-like body illustrated in FIG. 8.

Even by pinching and pulling downward a vicinity of a lower edge portion of a central portion in the horizontal direction of the upper belt-like body with fingers, as illustrated in a lower part of FIG. 9, a horizontal length of the upper edge portion remains as $L_0$ because the upper edge portion is fixed. Meanwhile, a horizontal length of the lower edge portion becomes $L_6$, which is longer than $L_0$. Further, with regard to a deformed state of a part between the upper edge portion and the lower edge portion, a deformed rate on a lower side is higher than that on an upper side. Specifically, although pre-deformation lengths of parts (1), (2), and (3) are equal to each other, with regard to post-deformation lengths of parts (1)', (2)', and (3)' corresponding respectively to those parts, the following relation is established: (1)'<(2)'<(3)'.

In this mode, three sides of both right and left ends and the upper edge portion of the upper belt-like body are fixed to the main-sheet portion, and hence stretching properties are poor in comparison with original stretchability of the stretchable material. However, the vertical length is longer than the vertical length of the upper belt-like body illustrated in FIG. 8, and hence an influence of fixation of the upper edge portion is reduced. As a result, the upper belt-like body in this mode can be more easily stretched.

The upper belt-like body as illustrated in FIGS. 8 and 9 is provided to serve as the nose wrapping pocket. In the present invention, materials, shapes, and the like of such a nose wrapping pocket and a jaw wrapping pocket are determined in consideration of the deformed states as described above.

In particular, with regard to the nose wrapping pocket, it is preferred to consider that the nose tip and the wings of the nose form a complex curved shape and there are significant personal differences of the shape. This is because conventional masks have problems of leakage of exhaled air and a shift of the mask around the nose.

In the present invention, the nose wrapping pocket is preferred to be used in a mode of covering the nose tip and the wings of the nose, and more preferred to be used in a mode of covering also the nose bridge (refer to FIGS. 5B and 5C). When the nose wrapping pocket covers also the nose bridge, exhaled air is less liable to leak even when some gaps are generated around the wings of the nose.

From the above-mentioned viewpoints, at the central portion in the horizontal direction, the depth of the nose wrapping pocket is preferred to be 20 mm or more, and more preferred to be 30 mm or more.

In addition, in terms of usability of, for example, preventing covering up to a vicinity of the eyes of the wearer during wearing, the depth of the nose wrapping pocket is preferred to be 100 mm or less.

Description is made of a relation between a stretchable material to be used for the nose wrapping pocket and a shape thereof.

FIGS. 10A to 10E are schematic plan views of masks including nose wrapping pockets, which are made of various materials and have various shapes. FIGS. 10A to 10E each illustrate only the main-sheet portion and the nose wrapping pocket. In addition, FIGS. 10A to 10E each show sizes of the main-sheet portion and the nose wrapping pocket of each sample prepared as described below.

Figure 10:
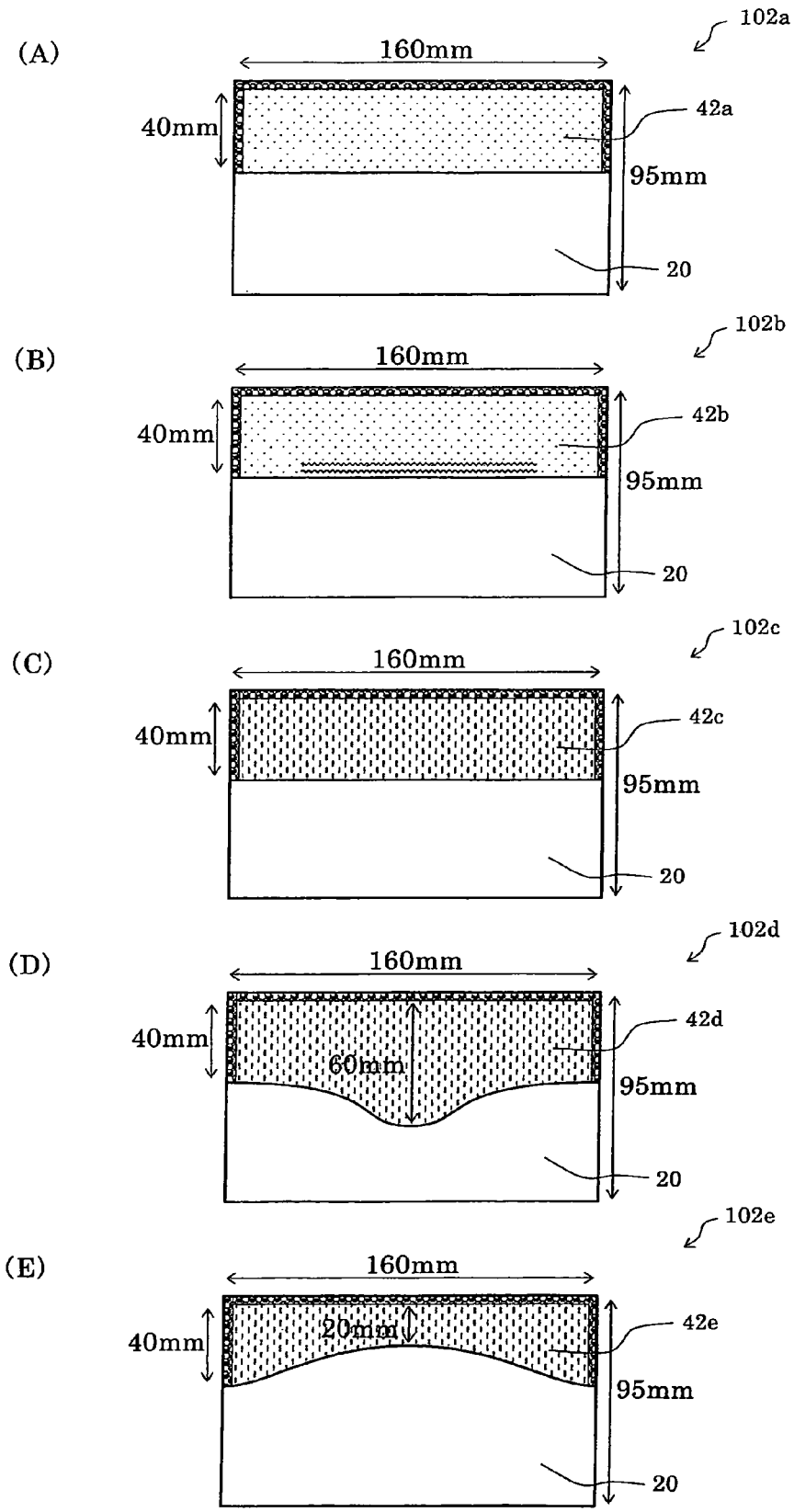
FIGS. 10A to 10D are schematic plan views of masks made of various materials and having nose wrapping pockets of various shapes.

Not only both right and left end portions of an upper belt-like body 42a, which is made of a non-stretchable material, of a mask 102a illustrated in FIG. 10A but also the entire upper marginal portion are coupled to the upper portion of the main-sheet portion 20, forming the nose wrapping pocket.

The upper belt-like body 42a of the mask 102a used as a sample in a wearing test described below was made of a PP•SMS non-woven fabric (manufactured by Avgol Ltd., with a basis weight of 13 g/m$^2$, and a breaking elongation of 30%), had a rectangular shape, and was coupled to the main-sheet portion 20 by heat sealing, the PP•SMS non-woven fabric being a non-stretchable material.

A mask 102b illustrated in FIG. 10B is the same as the mask 102a except that an upper belt-like body 42b, which is made of a non-stretchable material, is used instead of the upper belt-like body 42a.

The upper belt-like body 42b of the mask 102b used as a sample in the wearing test described below was formed by coupling and attaching, with a tackifier, two urethane-filament pieces in a state of being extended by 1.3 times to a vicinity of a lower edge portion of the upper belt-like body 42a, the two urethane-filament pieces each having a decitex of 470.

A mask 102c illustrated in FIG. 10C is the same as the mask 102a except that an upper belt-like body 42c, which is made of a stretchable material, is used instead of the upper belt-like body 42a.

The upper belt-like body 42c of the mask 102c used as a sample in the wearing test described below was made of a composite elastic body of an SEBS film and a PP non-woven fabric (manufactured by Tredegar Corporation, with a basis weight of 40 g/m$^2$, and a breaking elongation of 220%), coupled to the main-sheet portion 20 by heat sealing in a state of being extended by 1.3 times, the composite elastic body being a stretchable material having a uni-directional extensibility.

A mask 102d illustrated in FIG. 10D is the same as the mask 102c except that an upper belt-like body 42d, which is made of a stretchable material, is used instead of the upper belt-like body 42c.

The upper belt-like body 42d of the mask 102d used as a sample in the wearing test described below was obtained by increasing a vertical length of a horizontally central portion of the upper belt-like body 42c.

A mask 102e illustrated in FIG. 10E is the same as the mask 102c except that an upper belt-like body 42e, which is made of a stretchable material, is used instead of the upper belt-like body 42c.

The upper belt-like body 42e of the mask 102e used as a sample in the wearing test described below was obtained by decreasing the vertical length of the horizontally central portion of the upper belt-like body 42c.

The wearing tests of the masks illustrated in FIGS. 10A to 10E were performed. In the wearing tests, the masks were worn by a participant so that wearability, covering states, and formation states of gaps around the nose were evaluated. Tee following Table 1 shows results of the tests.

TABLE 1

| Sample | Wearability | Covering state and formation state of gaps around the nose | Comprehensive evaluation |
|---|---|---|---|
| 102a | Difficult to wear owing to low tensibility of the upper belt-like body. | The upper belt-like body was held in contact only with the nose tip, and loosened around the wings of the nose. Large gaps were formed. | x |
| 102b | Difficult to wear owing to low tensibility of the upper belt-like body. | The upper belt-like body was held in contact only with the nose tip and the tip of the wings of the nose. Gaps were formed. | x |
| 102c | The entire nose was able to be effectively covered owing to high tensibility of the upper belt-like body. | Covered along curved surfaces from the nose tip and the wings of the nose to the face. Gaps were not formed, but tension to the nose tip was felt. | ○ |
| 102d | The entire nose was able to be quite effectively covered owing to high tensibility of the upper belt-like body. | Covered along curved surfaces from the nose tip including an upper portion of the nose bridge and the wings of the nose to the face. Gaps were not formed, and soft covering was achieved without a tensile feel. | □ |
| 102e | The upper belt-like body is slightly difficult to pinch, but the entire nose was able to be covered. | Although fitting over the nose tip and covering up to the wings of the nose, the mask was slightly poor in stability. Gaps were slightly formed. | △ |

□: excellent,
○: good,
△: wearable,
x: poor

Table 1 clearly shows that, when the nose wrapping pocket is formed of the upper belt-like body made of a non-stretchable material (masks 102a and 102b), the masks are difficult to wear, and gaps are formed around the nose.

In contrast, when the nose wrapping pocket is formed of the upper belt-like body made of a stretchable material (masks 102c, 102d, and 102e), the masks are easily worn. In addition, gaps are not formed around the nose, or if any, slightly formed. Of those masks, the mask having the increased vertical length of the horizontally central portion of the upper belt-like body forming the nose wrapping pocket (mask 102d) is markedly preferred.

Next, description is made of the shapes of the jaw wrapping pocket and the nose wrapping pocket.

FIGS. 11A to 11F are schematic plan views of various jaw wrapping pockets. In FIGS. 11A to 11F, a coupling portion coupled to the main-sheet portion (not shown) is illustrated by a solid line, and an opening portion is illustrated by a dotted line. Note that, the entire solid line part of the jaw wrapping pocket may be coupled to the main-sheet portion, or part of the solid line part thereof may be coupled to the main-sheet portion.

Figure 11:
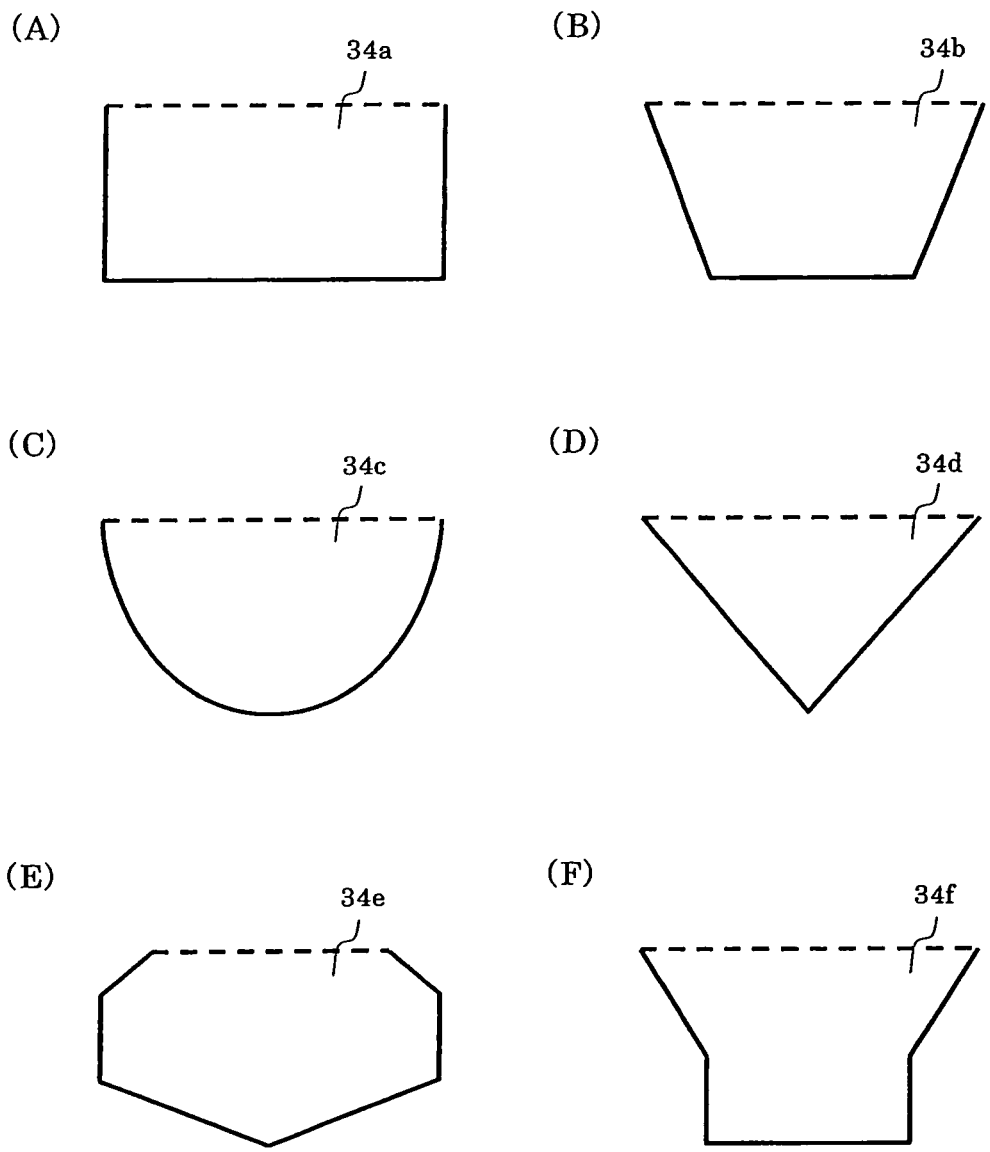
FIGS. 11A to 11F are schematic plan views of various jaw wrapping pockets.

A lower belt-like body 34a of the jaw wrapping pocket illustrated in FIG. 11A has a horizontally-long rectangular shape, and both right and left edge portions and a lower edge portion of the lower belt-like body 34a are to be coupled to the main-sheet portion.

A lower belt-like body 34b of the jaw wrapping pocket illustrated in FIG. 11B has a horizontally-long trapezoidal shape in which an upper side is longer than a lower side, and both right and left edge portions and a lower edge portion of the lower belt-like body 34b are to be coupled to the main-sheet portion.

A lower belt-like body 34c of the jaw wrapping pocket illustrated in FIG. 11C has a substantially semi-circular shape in which a chordal part is provided on an upper side, and an arc part provided from both right and left edge portions of the lower belt-like body 34c to a lower edge portion thereof is to be coupled to the main-sheet portion.

A lower belt-like body 34d of the jaw wrapping pocket illustrated in FIG. 11D has a horizontally-long isosceles triangular shape in which a base part is provided on an upper side, and two sides from both right and left edge portions of the lower belt-like body 34d to a lower edge portion thereof are to be coupled to the main-sheet portion.

In the present invention, even in such modes as those of the jaw wrapping pockets illustrated in FIGS. 11C and 11D, in which both right and left edge portions and the lower edge portion of the lower belt-like body are integrated with each other and difficult to be clearly separated from each other, the lower belt-like body corresponds to a lower belt-like body provided across both right and left end portions of the main-sheet portion.

A lower belt-like body 34e of the jaw wrapping pocket illustrated in FIG. 11E has a horizontally-long heptagonal shape, and six sides from both right and left edge portions of the lower belt-like body 34e to a lower edge portion thereof are to be coupled to the main-sheet portion.

A lower belt-like body 34f of the jaw wrapping pocket illustrated in FIG. 11F has a horizontally-long hexagonal shape, and five sides from both right and left edge portions of the lower belt-like body 34f to a lower edge portion thereof are to be coupled to the main-sheet portion.

In the present invention, it is possible to use such polygonal lower belt-like bodies as those of the jaw wrapping pockets illustrated in FIGS. 11E and 11F. In such cases, the lower belt-like body is not limited to a mode in which only one side of the lower belt-like body is not coupled to the main-sheet portion, and may be used in a mode in which two or more sides are not coupled to the main-sheet portion. For example, in FIG. 11E, two sides on both right and left sides of the uncoupled one side need not be coupled to the main-sheet portion as well.

One of preferred modes of the shapes of the above-mentioned various jaw wrapping pockets is to round off angular parts so as to achieve a soft touch.

In the above, the jaw wrapping pocket is described as an example with reference to FIGS. 11A to 11F, but the same applies to the nose wrapping pocket.

As described above, in the present invention, the jaw wrapping pocket and the nose wrapping pocket are not particularly limited in shape as long as the jaw wrapping pocket and the nose wrapping pocket are provided across both right and left end portions of the main-sheet portion.

Each of the lower belt-like body forming the jaw wrapping pocket and the upper belt-like body forming the nose wrapping pocket may be directly coupled to the main-sheet portion or may be indirectly coupled to the main-sheet portion as long as the lower belt-like body and the upper belt-like body are provided across both right and left end portions of the main-sheet portion.

Figure 12:
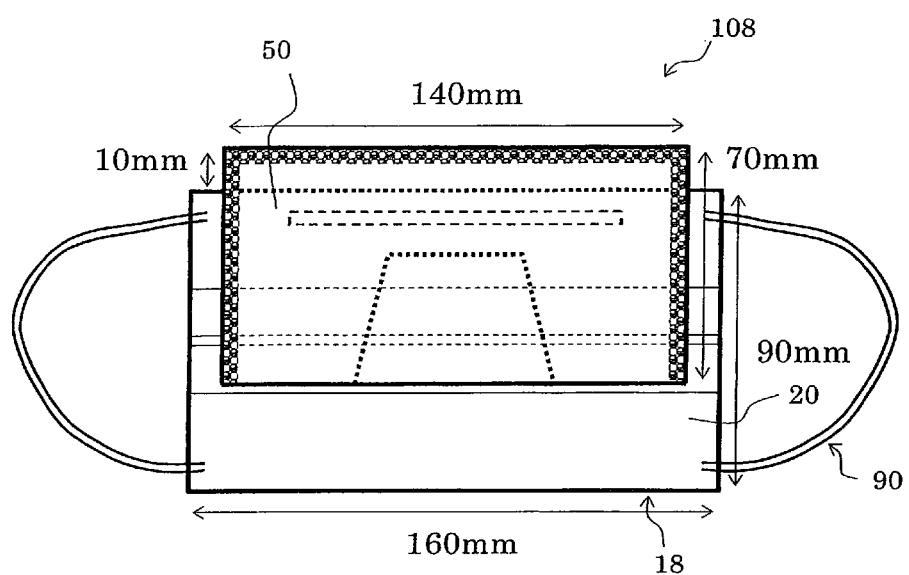
FIG. 12 is a schematic plan view of a mask in which an upper belt-like body forming the nose wrapping pocket is coupled indirectly to the main-sheet portion.
Figure 14:
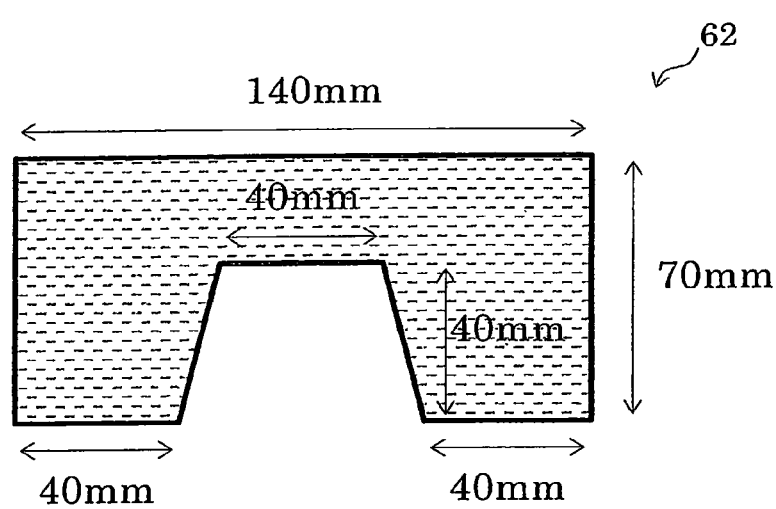
FIGS. 14A and 14B are schematic plan views respectively illustrating a composite sheet and a stretchable composite sheet forming the nose-wrapping-pocket structural body.
Figure 14:
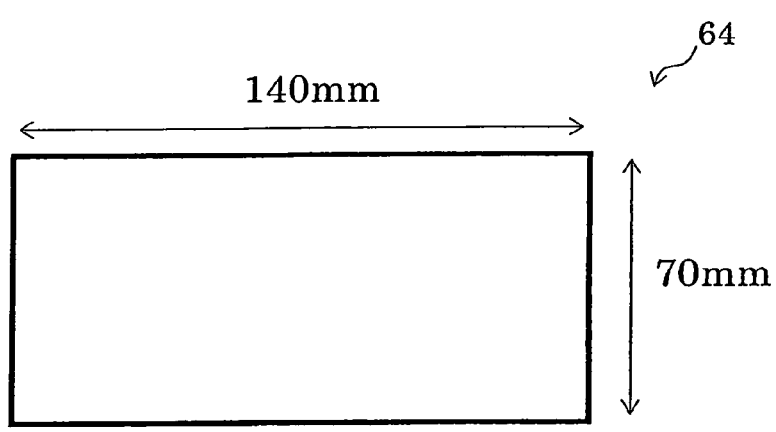

FIG. 12 is a schematic plan view of a mask in which an upper belt-like body forming the nose wrapping pocket is coupled indirectly to the main-sheet portion. Note that, the size of the mask illustrated in FIG. 12 is the same as that of a mask of Example 6 described below, but the present invention is not limited thereto (the same applies to FIG. 14).

A mask 108 illustrated in FIG. 12 basically includes a main-body portion 18 for covering the lower face portion of the wearer including the nose and the mouth and the fixation portions 90 which are coupled to the main-body portion 18 and fix the main-body portion 18 to the lower face portion of the wearer.

The main-body portion 18 includes the main-sheet portion 20 and a nose-wrapping-pocket structural body including an upper belt-like body 50 for holding the nose of the wearer, the upper belt-like body 50 being made of a belt-like stretchable material indirectly coupled to both the right and left end portions of the main-sheet portion 20 and provided across both the right and left end portions in the upper portion on the inner side of the main-sheet portion 20. Detailed description is made below of the upper belt-like body 50, members for coupling the upper belt-like body 50 to the main-sheet portion 20, and the like.

Figure 13:
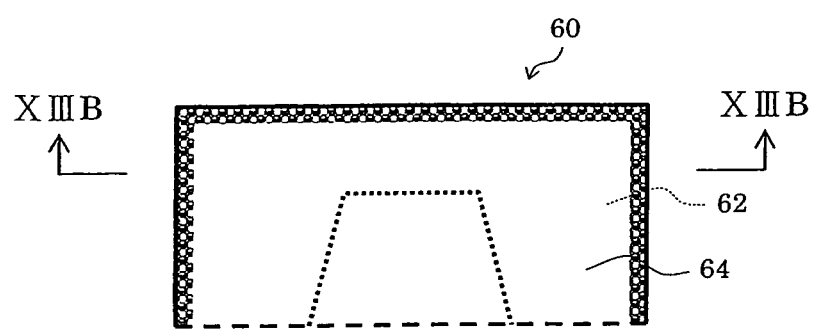
FIGS. 13A and 13B are schematic views each illustrating the nose-wrapping-pocket structural body including the upper belt-like body.
Figure 13:
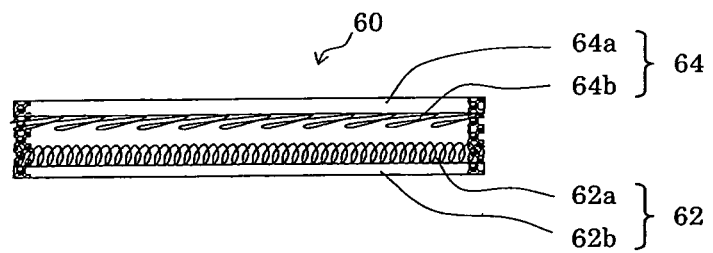

FIGS. 13A and 13B are schematic views each illustrating the nose-wrapping-pocket structural body including the upper belt-like body. Specifically, FIG. 13A is a plan view, and FIG. 13B is a lateral end view taken along the line XIIIB-XIIIB of FIG. 13A.

Further, FIGS. 14A and 14B are schematic plan views respectively illustrating a composite sheet and a stretchable composite sheet forming the nose-wrapping-pocket structural body.

As illustrated in FIGS. 13A and 13B, a nose-wrapping-pocket structural body 60 is formed by coupling a composite sheet 62 and a stretchable composite sheet 64, which is provided on an inner side of the composite sheet 62, to each other at an upper edge portion and both right and left edge portions thereof.

Specifically, a material for the composite sheet 62 is not particularly limited. For example, it is possible to use a composite sheet obtained by laminating an LLD·PE film (for example, that manufactured by Tonen Chemical Corporation, with a thickness of 20 μm) 62b on an outer side of a PE/PP spun-bonded non-woven fabric (for example, that manufactured by Chisso Corporation, with a basis weight of 20 g/m$^2$) 62a. The composite sheet 62 has a planar shape as illustrated in FIG. 14A. A trapezoidal cutout part of the composite sheet 62 is a part to fit to the lip portion, and such a cutout portion facilitates airflow.

Further, a material for the stretchable composite sheet 64 is not particularly limited as long as the stretchable composite sheet 64 is made of a belt-like stretchable material. For example, it is possible to use a stretchable composite sheet obtained by coupling to each other, by heat fusion, a polyurethane film 64a having an isotropic stretchability in a planar direction (for example, that manufactured by Sheedom Co., Ltd., with a thickness of 25 μm) and a PE/PET spun-lace non-woven fabric 64b having a uni-directional stretchability in the horizontal direction (for example, manufactured by UNITIKA Ltd., with a basis weight of 30 g/m$^2$), the PE/PET spun-lace non-woven fabric 64b being positioned on the outer side of the polyurethane film 64a. The stretchable composite sheet 64 has a planar shape as illustrated in FIG. 14B.

The nose-wrapping-pocket structural body 60 can be obtained by laminating the stretchable composite sheet 64 on the inner side of the composite sheet 62 so that the PE/PP spun-bonded non-woven fabric 62a and the PE/PET spun-lace non-woven fabric 64b are adjacent to each other, and by coupling the upper edge portions, and both the right and left edge portions of the stretchable composite sheet 64 and the composite sheet 62 to each other.

The main-body portion 18 of the mask 108 illustrated in FIG. 12 can be obtained by coupling the nose-wrapping-pocket structural body 60 as described above to the main-sheet portion 20. In the main-body portion 18, the stretchable composite sheet 64 of the nose-wrapping-pocket structural body 60 serves as the upper belt-like body 50.

The nose-wrapping-pocket structural body 60 and the main-sheet portion 20 can be coupled to each other, for example, by coupling means disoposed between the composite sheet 62 and the main-sheet portion 20. The coupling means is not particularly limited, and coupling methods using a hook-and-loop fastener, an adhesive, a tackifier, and the like can be exemplified.

In the main-body portion 18 of the mask 108 illustrated in FIG. 12, the main-sheet portion 20 and the nose-wrapping-pocket structural body 60 are coupled to each other so that an upper edge portion of the nose-wrapping-pocket structural body 60 is positioned above the upper edge portion of the main-sheet portion 20. However, in the present invention, a positional relation of the main-sheet portion and the nose-wrapping-pocket structural body is not particularly limited as long as the stretchable composite sheet 64 is provided across both the right and left end portions of the main-sheet portion 20 so as to serve as the upper belt-like body 50.

One of the preferred modes of the present invention is to provide, as in the case of the mask 108 illustrated in FIG. 12, a separate member such as the nose-wrapping-pocket structural body to the main-sheet portion so that a part of the separate member serves as the upper belt-like body.

Specifically, in the one of the preferred modes of the present invention, the nose wrapping pocket for accommodating the nose of the wearer is formed of a bag-like member having an opening provided on a lower side thereof (nose-wrapping-pocket structural body 60 in the case of the mask 108), the bag-like member being obtained by coupling an upper belt-like body (stretchable composite sheet 64 in the case of the mask 108) and a sheet-like object (composite sheet 62 in the case of the mask 108), which is provided on an outer side of the upper belt-like body, to each other at an upper edge portion and both right and left sides thereof, the bag-like member being coupled to the main-sheet portion at a portion of the sheet-like object so that the upper belt-like body is positioned in an upper portion on the inner side of the main-sheet portion.

Note that, each of the upper belt-like body and the sheet-like object of the mask 108 illustrated in FIG. 12 is a composite member made of two different materials, but the present invention is not limited thereto. For example, each of the upper belt-like body and the sheet-like object may be a member made of a single material, or may be a composite member made of three or more materials. For example, in Example 8 described below, a member made of a spun-bonded non-woven fabric is used for the sheet-like object.

Figure 15:
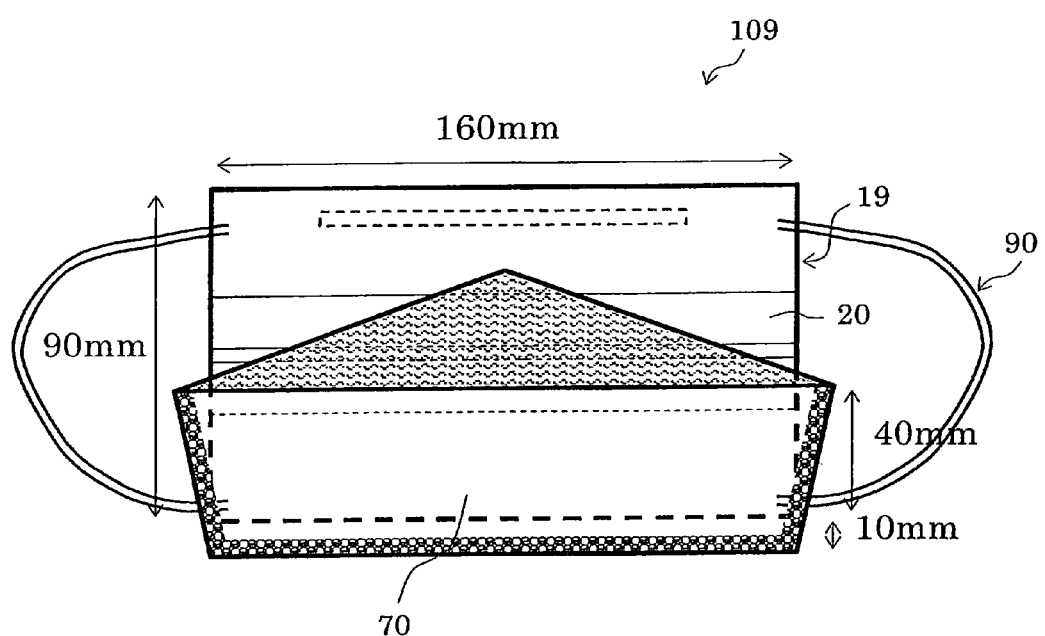
FIG. 15 is a schematic plan view of a mask in which a lower belt-like body forming the jaw wrapping pocket is coupled indirectly to the main-sheet portion.
Figure 17:
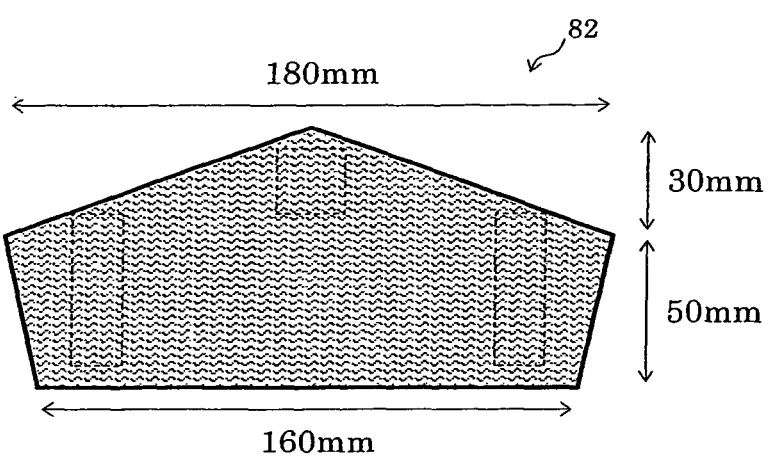
FIGS. 17A and 17B are schematic plan views respectively illustrating a non-woven fabric sheet and a stretchable composite sheet forming the jaw-wrapping-pocket structural body.
Figure 17:
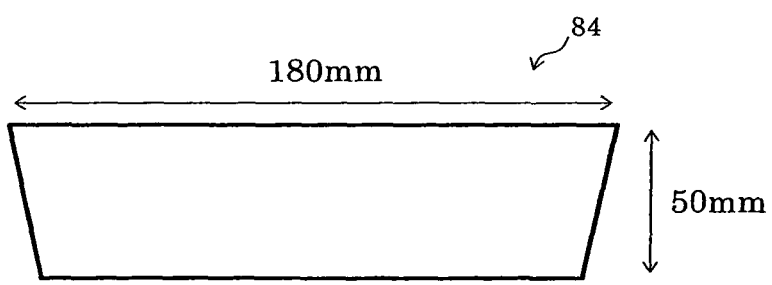

FIG. 15 is a schematic plan view of a mask in which a lower belt-like body forming the jaw wrapping pocket is coupled indirectly to the main-sheet portion. Note that, the size of the mask illustrated in FIG. 15 is the same as that of a mask of Example 7 described below, but the present invention is not limited thereto (the same applies to FIG. 17).

A mask 109 illustrated in FIG. 15 basically includes a main-body portion 19 for covering the lower face portion of the wearer including the nose and the mouth and the fixation portions 90 which are coupled to the main-body portion 19 and fix the main-body portion 19 to the lower face portion of the wearer.

The main-body portion 19 includes the main-sheet portion 20 and a jaw-wrapping-pocket structural body including a lower belt-like body 70 for holding the jaw of the wearer, the lower belt-like body 70 being made of a belt-like stretchable material indirectly coupled to both the right and left end portions of the main-sheet portion 20 and provided across both the right and left end portions in the lower portion on the inner side of the main-sheet portion 20. Detailed description is made below of the lower belt-like body 70, members for coupling the lower belt-like body 70 to the main-sheet portion 20, and the like.

Figure 16:
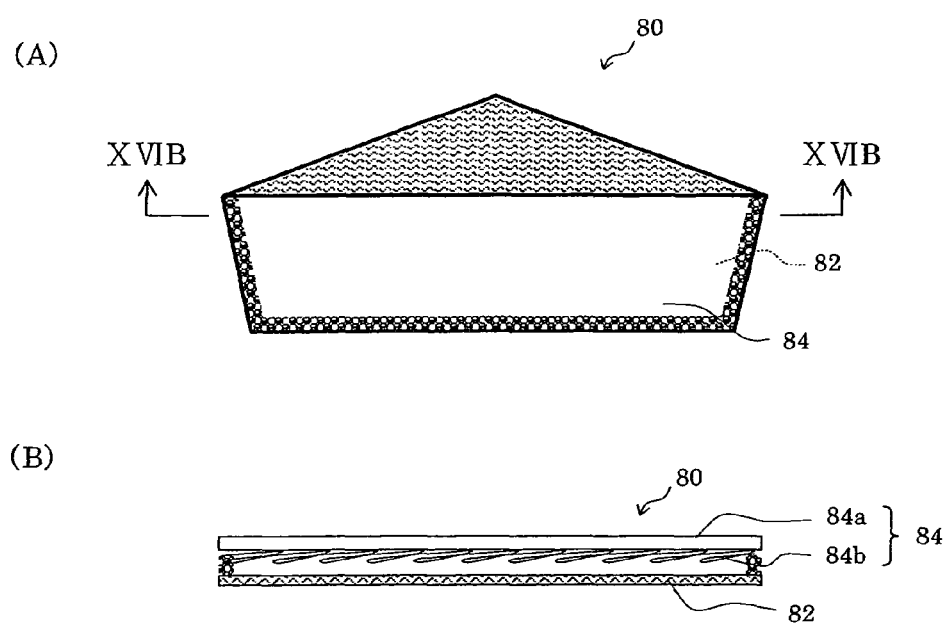
FIGS. 16A and 16B are schematic views each illustrating a jaw-wrapping-pocket structural body including the lower belt-like body.

FIGS. 16A and 16B are schematic views each illustrating the jaw-wrapping-pocket structural body including the lower belt-like body. Specifically, FIG. 16A is a plan view, and FIG. 16B is a lateral end view taken along the line XVIB-XVIB of FIG. 16A.

Further, FIGS. 17A and 17B are schematic plan views respectively illustrating a non-woven fabric sheet and a stretchable composite sheet forming the jaw-wrapping-pocket structural body.

As illustrated in FIGS. 16A and 16B, a jaw-wrapping-pocket structural body 80 is formed by coupling a non-woven fabric sheet 82 and a stretchable composite sheet 84, which is provided on an inner side of the non-woven fabric sheet 82, to each other at a lower edge portion and both right and left edge portions thereof.

Specifically, the non-woven fabric sheet 82 is preferred to be air-permeable, and for example, a gauze-like TCF non-woven fabric (for example, #403, manufactured by FUTAMURA CHEMICAL CO., LTD., with a basis weight of 30 g/m$^2$) can be used as the non-woven fabric sheet 82. The non-woven fabric sheet 82 has a planar shape as illustrated in FIG. 17A.

The jaw-wrapping-pocket structural body 80 has a shape in which an isosceles triangular part of the non-woven fabric sheet 82 is exposed and the exposed portion is assumed to be a part to be brought into contact with the lips. Note that, tackifier tapes each having a peelable layer are provided at three parts (on the outer surface) each surrounded by dotted lines in FIG. 17A.

Further, a material for the stretchable composite sheet 84 is not particularly limited as long as the stretchable composite sheet 84 is made of a belt-like stretchable material. For example, it is possible to use a stretchable composite sheet obtained by coupling to each other, by heat fusion, a polyurethane film 84a having an isotropic stretchability in a planar direction (for example, that manufactured by Sheedom Co., Ltd., with a thickness of 25 μm) and a PE/PET spun-lace non-woven fabric 84b having a uni-directional stretchability in the horizontal direction (for example, that manufactured by UNITIKA Ltd., with a basis weight of 30 g/m$^2$), the PE/PET spun-lace non-woven fabric 84b being positioned on the outer side of the polyurethane film 84a. The stretchable composite sheet 84 has a planar shape as illustrated in FIG. 17B.

The jaw-wrapping-pocket structural body 80 can be obtained by laminating the stretchable composite sheet 84 on the inner side of the non-woven fabric sheet 82 so that the non-woven fabric sheet 82 and the PE/PET spun-lace non-woven fabric 84b are adjacent to each other and that an upper edge portion of the non-woven fabric sheet 82 protrudes from the upper edge portion of the stretchable composite sheet 84, and by coupling, by heat fusion, the lower edge portions and both the right and left edge portions of the stretchable composite sheet 84 and the non-woven fabric sheet 82 to each other.

The main-body portion 19 of the mask 109 illustrated in FIG. 15 can be obtained by coupling the jaw-wrapping-pocket structural body 80 as described above to the main-sheet portion 20. In the main-body portion 19, the stretchable composite sheet 84 of the jaw-wrapping-pocket structural body 80 serves as the lower belt-like body 70.

The main-sheet portion 20 and the jaw-wrapping-pocket structural body 80 are coupled to each other with the above-mentioned tackifier tapes disposed on a rear surface of the non-woven fabric sheet 82.

In the main-body portion 19 of the mask 109 illustrated in FIG. 15, the main-sheet portion 20 and the jaw-wrapping-pocket structural body 80 are coupled to each other so that a lower edge portion of the jaw-wrapping-pocket structural body 80 is positioned below the lower edge portion of the main-sheet portion 20 and that both the right and left edge portions of the jaw-wrapping-pocket structural body 80 are positioned on horizontally outer sides of both the right and left edge portions of the main-sheet portion 20. However, in the present invention, a positional relation of the main-sheet portion and the jaw-wrapping-pocket structural body is not particularly limited as long as the stretchable composite sheet 84 is provided across both the right and left end portions of the main-sheet portion 20 so as to serve as the lower belt-like body 70.

One of the preferred modes of the present invention is to provide, as in the case of the mask 109 illustrated in FIG. 15, a separate member such as the jaw-wrapping-pocket structural body to the main-sheet portion so that a part of the separate member serves as the lower belt-like body.

Specifically, in the one of the preferred modes of the present invention, the jaw wrapping pocket for accommodating the jaw of the wearer is formed of a bag-like member having an opening provided on a upper side thereof (jaw-wrapping-pocket structural body 80 in the case of the mask 109), the bag-like member being obtained by coupling a lower belt-like body (stretchable composite sheet 84 in the case of the mask 109) and a sheet-like object (non-woven fabric sheet 82 in the case of the mask 109), which is provided on the outer side of the lower belt-like body, to each other at a lower edge portion and both right and left sides thereof, the bag-like member being coupled to the main-sheet portion at a portion of the sheet-like object so that the lower belt-like body is positioned in an lower portion on the inner side of the main-sheet portion.

Note that, the lower belt-like body of the mask 109 illustrated in FIG. 15 is a composite member made of two materials, but the present invention is not limited thereto. For example, the lower belt-like body may be a member made of a single material, or may be a composite member made of three or more materials. Further, the sheet-like object of the mask 109 illustrated in FIG. 15 is a member made of a single material, but the present invention is not limited thereto. For example, the sheet-like object may be a composite member made of two or more materials.

In the present invention, as methods of forming the jaw wrapping pocket and the nose wrapping pocket with use of the lower belt-like body and the upper belt-like body, as described above, the followings are exemplified: a method of coupling the lower belt-like body and the upper belt-like body directly to the main-sheet portion; a method of coupling the bag-like member formed of the lower belt-like body and the bag-like member formed of the upper belt-like body to the main-sheet portion; and a method combining those methods (for example, a method of coupling the lower belt-like body directly to the main-sheet portion and coupling the bag-like member formed of the upper belt-like body to the main-sheet portion, and a method of coupling the bag-like member formed of the lower belt-like body to the main-body portion and coupling the upper belt-like body directly to the main-sheet portion).

The method of coupling the lower belt-like body and the upper belt-like body directly to the main-sheet portion has advantages that material cost is saved and manufacturing steps are simplified.

In the methods of coupling the bag-like member formed of the lower belt-like body and the bag-like member formed of the upper belt-like body to the main-sheet portion, depending on a mode of coupling the bag-like members to the main-sheet portion, the lower belt-like body and the upper belt-like body can each be positioned on the outer side or the inner side in the horizontal direction with respect to the right and left edge portions of the main-sheet portion. The bag-like members and the main-sheet portion are coupled relatively easily to each other, and hence the structure of the main-sheet portion of the bag-like member can be designed independently of each other. As a result, various modes can be achieved.

Further, the bag-like member may be formed detachably so that only the bag-like member is detached and disposed when the bag-like member is tainted as a result of wearing, and the main-sheet portion may be made of a washable material so as to be used a plurality of times.

Description is made below of shapes of the jaw wrapping pocket and the nose wrapping pocket using the bag-like member described above.

Figure 18:
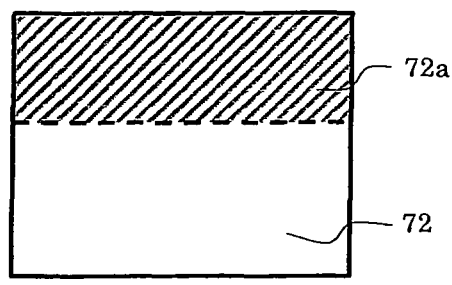
FIGS. 18A and 18B are schematic plan views of various jaw wrapping pockets.
Figure 18:
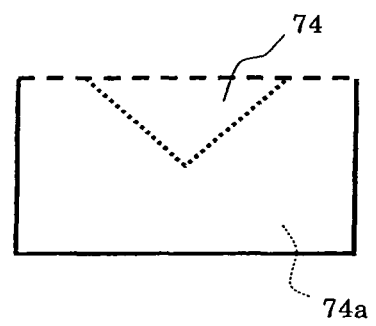

FIGS. 18A and 18B are schematic plan views of various jaw wrapping pockets. In FIGS. 18A and 18B, an edge portion of the jaw wrapping pocket is illustrated by a solid line, and an opening portion thereof is illustrated by a dotted line. Note that, unlike the description with reference to FIG. 17A, the jaw wrapping pocket and the main-sheet portion (not shown) do not need to be coupled to each other at the edge portions of the jaw wrapping pocket. The jaw wrapping pocket and the main-sheet portion may be partially coupled to each other with a tackifier and the like so as not to shift from each other.

A lower belt-like body 72 of the jaw wrapping pocket illustrated in FIG. 18A has a horizontally-long rectangular shape, and the lower belt-like body 72 and a sheet-like object 72a, which is provided on an outer side of the lower belt-like body 72 are coupled to each other at a lower edge portion and both right and left sides thereof so that an upper edge portion of the sheet-like object 72a protrudes. In this way, the bag-like member having an opening provided on the upper side thereof is formed. The bag-like member and the main-sheet portion are coupled to each other normally by coupling means provided on an outer surface of the sheet-like object 72a.

A lower belt-like body 74 of the jaw wrapping pocket illustrated in FIG. 18B has a horizontally-long rectangular shape, and the lower belt-like body 74 and a sheet-like object 74a, which is provided on an outer side of the lower belt-like body 74 (and which has a cutout portion provided at a center of an upper edge portion), are coupled to each other at a lower edge portion and both right and left sides thereof. In this way, the bag-like member having an opening provided on the upper side thereof is formed. The bag-like member and the main-sheet portion are coupled to each other normally by coupling means provided on an outer surface of the sheet-like object 74a.

In this mode using the bag-like member, the lower belt-like body and the sheet-like object are not particularly limited in shape as long as an overlapping part therebetween is secured.

In the above, the jaw wrapping pocket is described as an example, but the same applies to the nose wrapping pocket.

Further, in the present invention, one of preferred modes of the lower belt-like body is to include a slit or a hole for accommodating the lower jaw of the wearer.

Figure 29:
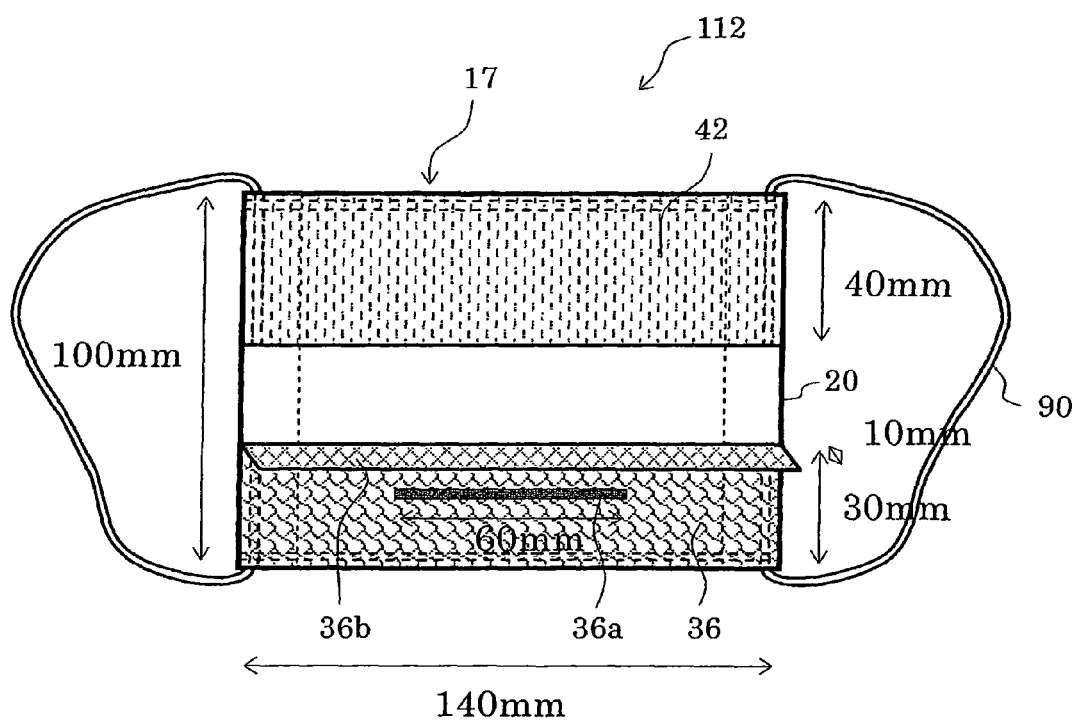
FIG. 29 is a schematic plan view illustrating yet another example of the mask according to the present invention.

FIG. 29 is a schematic plan view illustrating yet another example of the mask according to the present invention (note that, the flap 36b is perspectively illustrated). Note that, the size of the mask in FIG. 29 is the same as that of the mask of Example 4 described below, but the present invention is not limited thereto.

A mask 112 illustrated in FIG. 29 is basically the same as the mask 102 except that a main-sheet portion 20 of a main-body portion 17 is provided with a lower belt-like body 36 instead of the lower belt-like body 32.

The lower belt-like body 36 is basically the same as the lower belt-like body 32 except that the lower belt-like body 36 includes a slit 36a and the flap 36b.

The slit 36a accommodates the lower jaw of the wearer during wearing. With this, the lower belt-like body 36 more reliably accommodates the lower jaw, and a shift is less liable to occur.

The flap 36b provides an effect of facilitating insertion of the lower jaw into the slit 36a by being drawn at the time of accommodating the lower jaw.

Note that, the lower belt-like body 36 includes the slit 36a, but the same effect can be achieved even when the lower belt-like body includes a hole instead of the slit.

In the present invention, one of preferred modes of the lower belt-like body and/or the upper belt-like body is a mode in which the lower belt-like body and/or the upper belt-like body are provided so as to be positioned between the main-body portion and the skin of the wearer.

Figure 19:
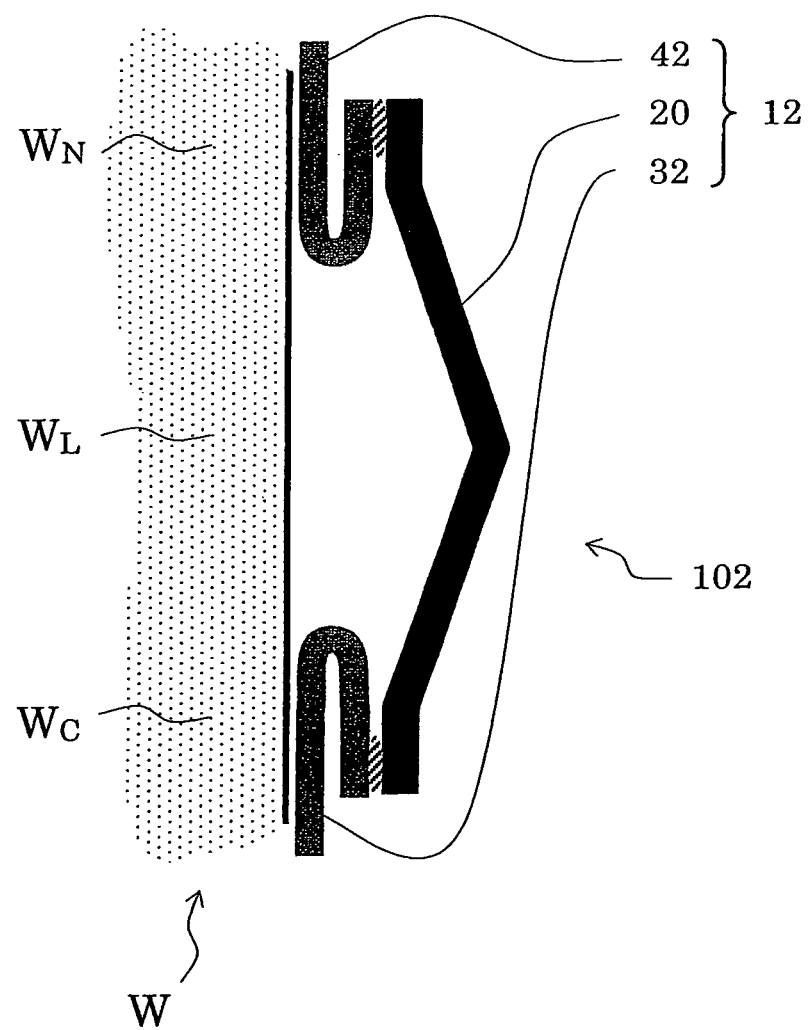
FIG. 19 is a schematic end view of a central portion in a horizontal direction of the mask according to the present invention when the mask is worn, in which the lower belt-like body and the upper belt-like body are provided so as to be positioned between the main-sheet portion and skin of a wearer during wearing.

FIG. 19 is a schematic end view of a horizontally central portion of the mask according to the present invention during wearing, in which the lower belt-like body and the upper belt-like body are provided so as to be positioned between the main-sheet portion and the skin of the wearer during wearing.

The mask 102 illustrated in FIG. 19 is the mask 102 illustrated in FIGS. 4 and 5B. As described above, the entire lower edge portion of the lower belt-like body 32 is coupled to the main-sheet portion 20 (in FIG. 19, shaded portion is the coupled portion) so as to form the jaw wrapping pocket for accommodating a part of the lower jaw $W_C$ of the skin W of the wearer. The entire upper edge portion of the upper belt-like body 42 is coupled to the main-sheet portion 20 (in FIG. 19, another shaded portion is the coupled portion) so as to form the nose wrapping pocket for accommodating a part of the nose tip $W_N$ of the skin W of the wearer.

As illustrated in FIG. 19, when the lower belt-like body 32 is folded back during wearing, a doubled part is formed between the main-sheet portion 20 and the skin W of the wearer. Similarly, as illustrated in FIG. 19, when the upper belt-like body 42 is folded back during wearing, another doubled part is formed between the main-sheet portion 20 and the skin W of the wearer. Further, parts of lips $W_L$ of the skin W of the wearer are not held in contact with any part of the mask 102.

With such a structure, the inner surface of the main-sheet portion 20 and the skin W of the wearer are out of contact with each other during wearing.

Figure 20:
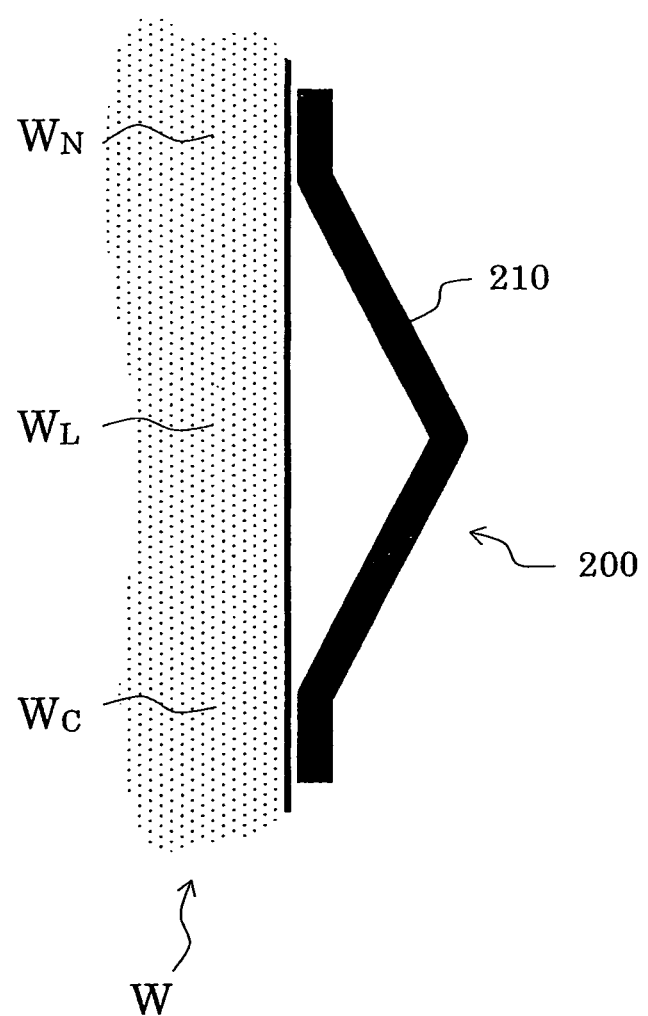
FIG. 20 is a schematic end view of a central portion in a horizontal direction of a conventionally well-known ultra three-dimensional mask when the ultra three-dimensional mask is worn.

FIG. 20 is a schematic end view of a central portion of a conventionally well-known ultra three-dimensional mask in the horizontal direction when the mask is worn.

During wearing, an inner surface of a main-body sheet portion 210 of a mask 200 illustrated in FIG. 20 is held in direct contact with the lower jaw $W_C$ and the nose tip $W_N$ of the skin W of the wearer.

As described above, at the lower jaw, the nose tip, and both the cheeks, the skin of the wearer is held in firm contact with the inner surface of the main-body sheet portion of a conventionally well-known, so-called ultra three-dimensional mask. The same applies to what is called a three-dimensional mask.

Further, as in the case of the three-dimensional mask, the lower jaw, the nose tip, and both the cheeks are held in contact with an inner surface of a main-body sheet portion of a conventionally well-known pleated mask. In addition, the mouth may be held in contact with the inner surface of the main-body sheet portion in some cases.

As described above, any of the conventionally-well known masks has a structure in which the skin of the wearer is held in contact with the inner surface of the main-body sheet portion.

In contrast, in the above-mentioned mode of the present invention, in which at least one of the lower belt-like bodies and the upper belt-like bodies are provided so as to be positioned between the main-sheet portion and the skin of the wearer during wearing, it is possible to easily achieve a wearing state (floating state) in which the inner surface of the main-sheet portion and the skin of the wearer are out of contact with each other.

Further, description is made of still another mode of the present invention in which at least one of the lower belt-like body and the upper belt-like body are provided so as to be positioned between the main-sheet portion and the skin of the wearer during wearing.

FIGS. 21A and 21B are schematic views illustrating still another example of the mask according to the present invention. FIG. 21A is a plan view, and FIG. 21B is a perspective view. Note that, the size of the mask illustrated in FIGS. 21A and 21B is the same as that of a mask of Example 5 described below, but the present invention is not limited thereto.

A mask 110 illustrated in FIGS. 21A and 21B is basically the same as the mask 102 except that the main-sheet portion 20 of a main-body portion 11 is provided with a lower belt-like body 34 and an upper belt-like body 44 instead of the lower belt-like body 32 and the upper belt-like body 42, and provided with fixation portions 92 instead of the fixation portions 90, the lower belt-like body 34 and the upper belt-like body 44 having different shapes as those of the lower belt-like body 32 and the upper belt-like body 42, respectively, the fixation portions 92 having different shapes as those of the fixation portions 90.

A vertical length of the lower belt-like body 34 is long at both right and left edge portions and a central portion in the horizontal direction, and is short therebetween (at two portions on right and left sides).

Similarly, a vertical length of the upper belt-like body 44 is long at both horizontal edge portions and a central portion in the right and left direction, and is short therebetween (at two portions on right and left sides).

The lower belt-like body 34 and the upper belt-like body 44 are coupled to the main-sheet portion 20 under a state in which the lower belt-like body 34 and the upper belt-like body 44 are overlapped on each other in vicinities of both the right and left edge portions so that the upper belt-like body 44 is positioned on an outer side and the lower belt-like body 34 is positioned on an inner side. Specifically, both the edge portions of the upper belt-like body 44 are coupled to both the right and left edge portions of the main-sheet portion 20, and both the edge portions of the lower belt-like body 34 are coupled to parts at which the lower belt-like body 34 is overlapped on both the right and left edge portions of the main-sheet portion 20 and both the edge portions of the upper belt-like body 44.

The shapes of the fixation portions 92 are different from those of the fixation portions 90.

Figure 21:
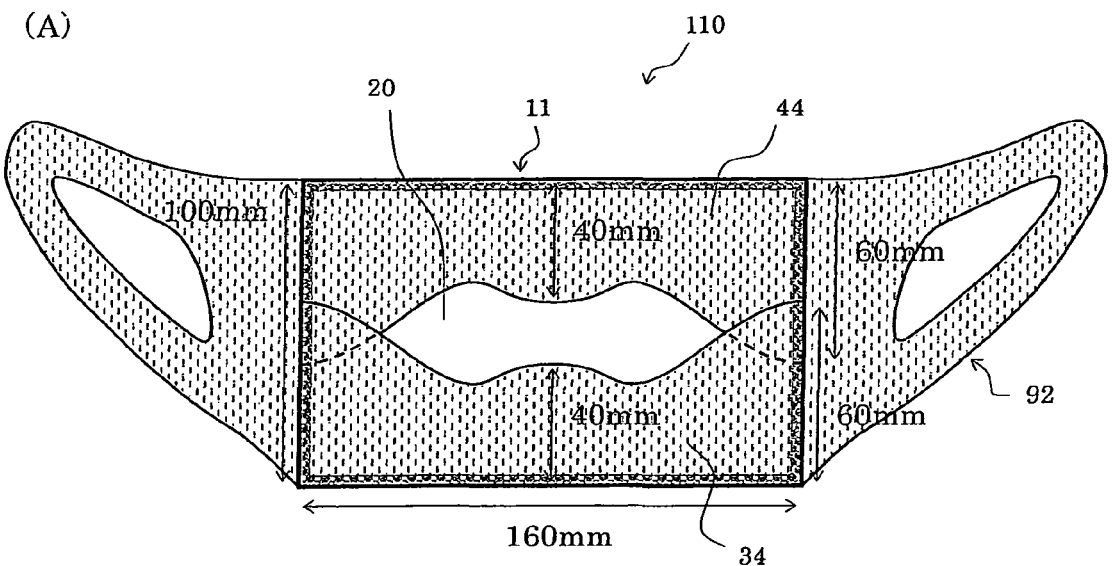
FIGS. 21A and 21B are schematic views illustrating still another example of the mask according to the present invention.
Figure 21:
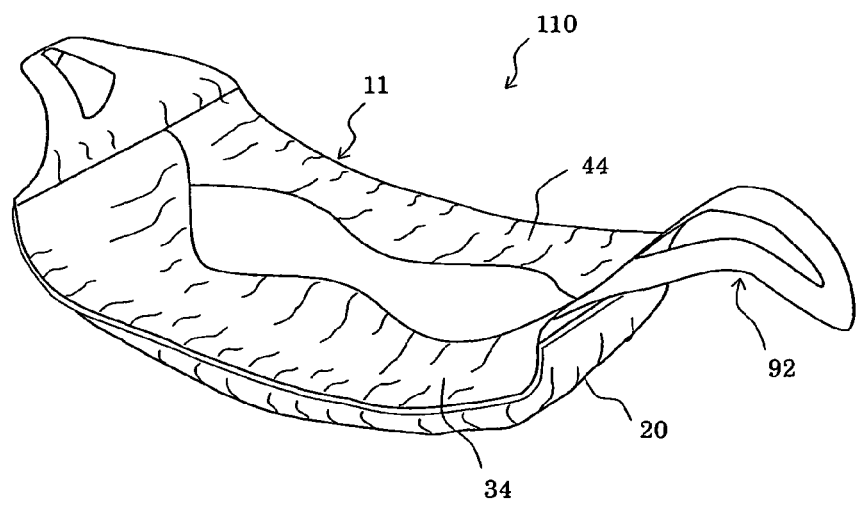
Figure 22:
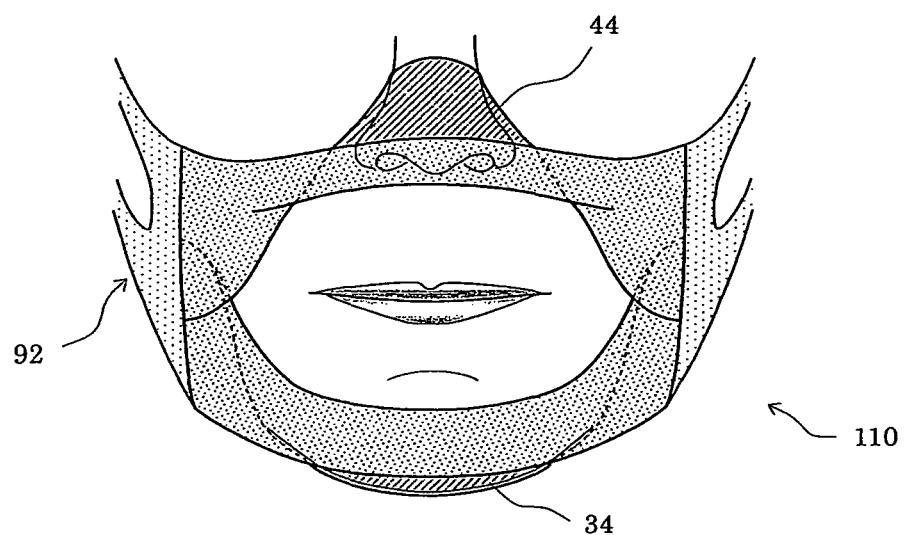
FIGS. 22A and 22B are schematic views illustrating the mask according to the present invention illustrated in FIGS. 21A and 21B, when the mask is worn.
Figure 22:
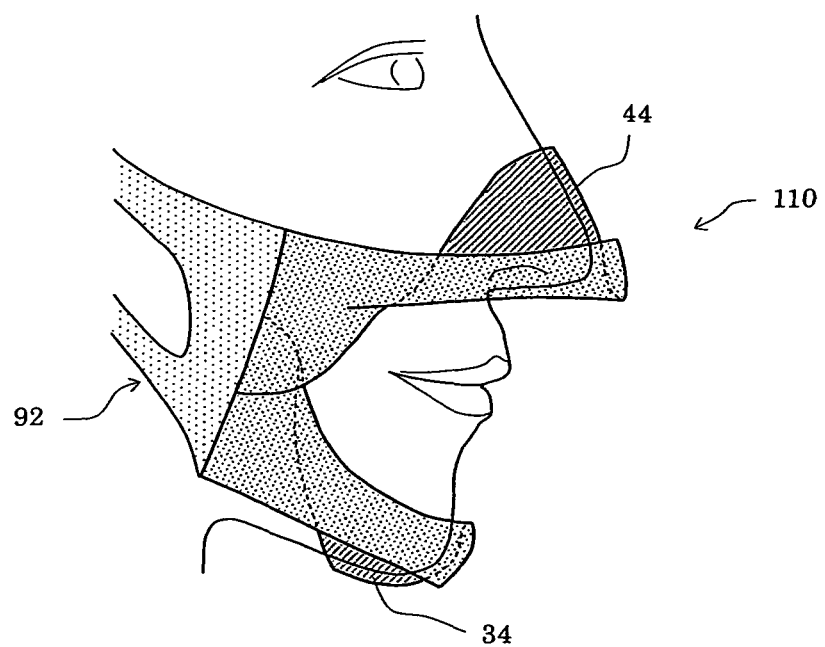

FIGS. 22A and 22B are schematic views illustrating the mask according to the present invention illustrated in FIGS. 21A and 21B, when the mask is worn. FIG. 22A illustrates a front side of the face of the wearer, and FIG. 22B illustrates a right side of the face of the wearer. FIGS. 22A and 22B do not illustrate the main-sheet portion in order to clearly illustrate an existing state of the lower belt-like body and the upper belt-like body.

The lower belt-like body 34 and the upper belt-like body 44 of the mask 110 are provided so as to be positioned between the main-sheet portion (not shown) and the skin of the wearer during wearing.

The lower belt-like body 34 is provided so as to be held in contact with the face of the wearer, covering a region of the face of the wearer from the lower jaw to both the cheeks via the jawbone. Further, the upper belt-like body 44 is provided so as to be held in contact with the face of the wearer, covering a region of the face from the nose tip to both the cheeks via the wings of the nose of the face.

As described above, the lower belt-like body 34 and the upper belt-like body 44 have the parts at which the lower belt-like body 34 and the upper belt-like body 44 are overlapped on each other in the vicinities of both the horizontal edge portions, and hence form an annular structure surrounding a peripheral portion of the lips of the face of the wearer. The main-sheet portion is to be positioned on the outer side of the lower belt-like body 34 and the upper belt-like body 44. Thus, the main-sheet portion is in a state of being out of contact with the face of the wearer (floating state). In other words, a space is formed between the main-sheet portion and the peripheral portion of the lips.

As described above, the lower belt-like body 34, the upper belt-like body 44, and the main-sheet portion are out of contact with the peripheral portion of the lips, and hence the wearer does not feel a burden during talking or mouth breathing. Further, a nostril portion of the mask is open to the space in the peripheral portion of the lips, and hence the wearer does not feel a burden also during nose breathing.

Further, the lower belt-like body 34 is doubled by being folded back at a part covering the lower jaw, and the upper belt-like body 44 is doubled by being folded back at a part covering the nose tip. In this way, between the main-sheet portion and the skin of the wearer, doubled parts are formed by folding back the lower belt-like body 34 and the upper belt-like body 44 during wearing. Thus, it is possible to easily achieve the wearing state (floating state) in which the inner surface of the main-sheet portion and the skin of the wearer are out of contact with each other. Further, the lower belt-like body 34 and the upper belt-like body 44 are folded back, and hence fitting properties with respect to the skin of the wearer are enhanced, which provides an advantage that exhaled air is less liable to leak.

Note that, the mask 110 illustrated in FIGS. 21A and 21B includes both the lower belt-like body 34 and the upper belt-like body 44, but the present invention is not limited thereto. For example, the mask 110 may include only the lower belt-like body, or only the upper belt-like body.

In the following, further description is made of the space to be formed between the main-sheet portion and the skin of the wearer (hereinafter, also referred to as "inner-mask space").

Figure 23:
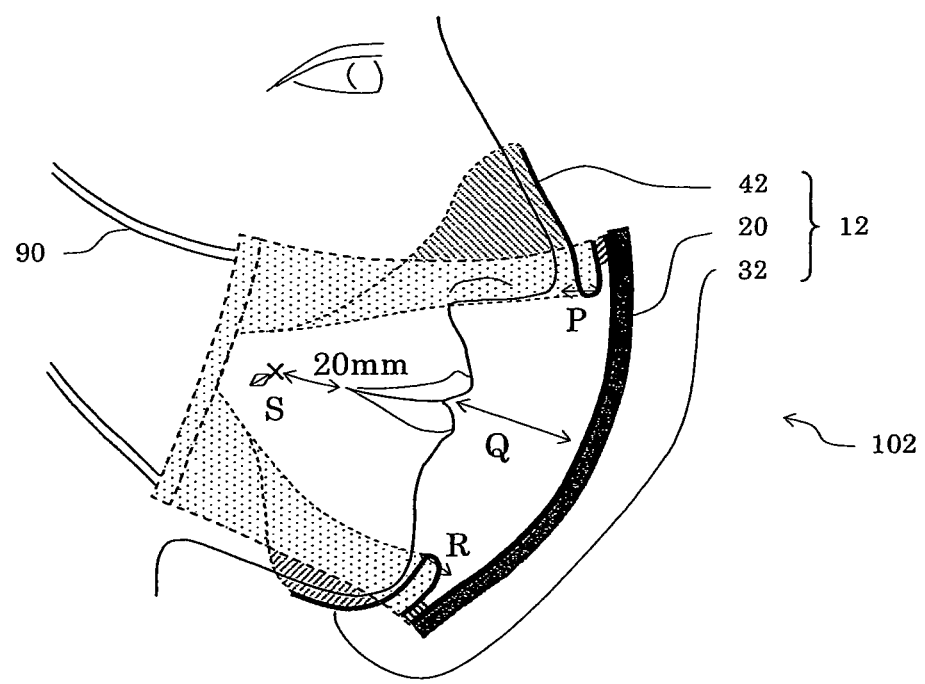
FIG. 23 is an explanatory diagram illustrating an inner-mask space.

FIG. 23 is an explanatory diagram illustrating the inner-mask space.

FIG. 23 is basically the same as FIG. 5B except that reference symbols for description of the inner-mask space are added.

Reference symbol P represents a shortest distance between the inner surface of the main-sheet portion 20 and a horizontally central, lowermost portion of a part of the nose of the wearer which comes into contact with the main-body portion 12.

Reference symbol Q represents a shortest distance between the inner surface of the main-sheet portion 20 and a horizontally central, lowermost portion of the upper lip of the wearer.

Reference symbol R represents a shortest distance between the inner surface of the main-sheet portion 20 and a horizontally central, uppermost portion of a part of the jaw of the wearer which comes into contact with the main-body portion 12.

Reference symbol S represents a shortest distance between the inner surface of the main-sheet portion 20 and a part of the cheek, which is at a position 20 mm away from a corner of the mouth of the wearer, the position being on an extension line extending outward from a closing line of the upper and lower lips in a lip-closed state.

The distances P, Q, R, and S are each or collectively referred to as "inner-mask-space distance."

The mode of the present invention, in which the inner surface of the main-sheet portion and the skin of the wearer are out of contact with each other during wearing, is achieved as follows, for example, as illustrated in FIG. 23. The lower belt-like body 32 is provided so that the lower belt-like body 32 exists between the main-sheet portion and the skin of the wearer during wearing, and the upper belt-like body 42 is provided so that the upper belt-like body 42 exists between the main-sheet portion and the skin of the wearer during wearing. Further, the upper belt-like body 42 is held in contact with the nose of the wearer, and supports the main-sheet portion 20. Thus, the distance P (shortest distance between the inner surface of the main-sheet portion 20 and the horizontally central, lowermost portion of the part of the nose of the wearer which comes into contact with the upper belt-like body 42) and the distance R (shortest distance between the inner surface of the main-sheet portion 20 and the horizontally central, uppermost portion of the part of the jaw of the wearer which comes into contact with the lower belt-like body 32) are respectively determined depending mainly on thicknesses of the upper belt-like body 42 and the lower belt-like body 32. In this regard, further description is made of the distance P with reference to the drawings.

Figure 24:
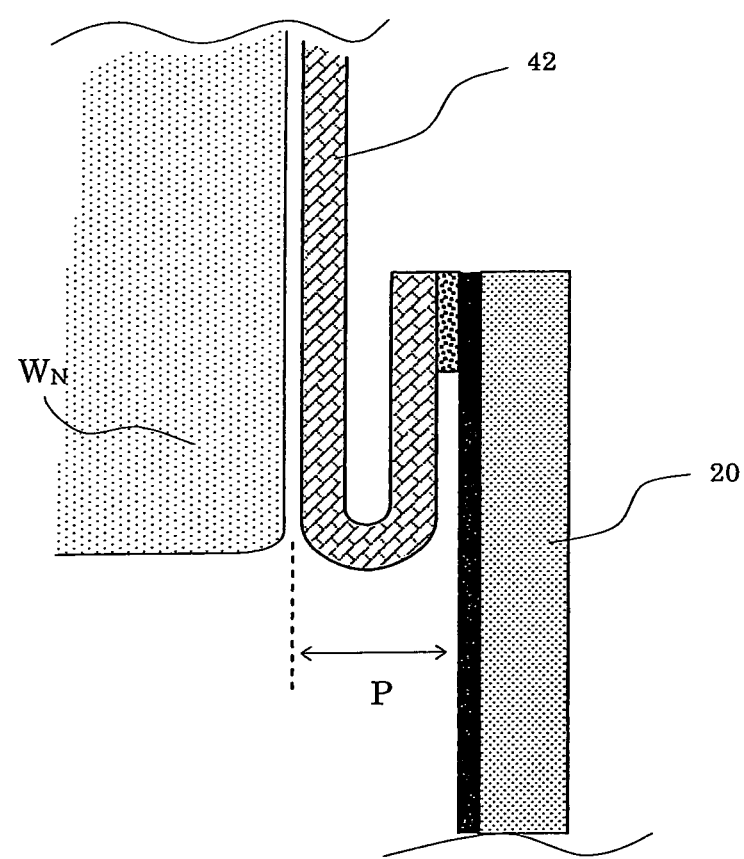
FIG. 24 is an enlarged explanatory diagram illustrating a vicinity of a contact part of the upper belt-like body and the nose of a wearer in FIG. 23.

FIG. 24 is an enlarged explanatory diagram illustrating a vicinity of the contact part of the upper belt-like body 42 with the nose of the wearer in FIG. 23. As illustrated in FIG. 24, the distance P (shortest distance between the inner surface of the main-sheet portion 20 and the horizontally central, lowermost portion of the part of the nose of the wearer which comes into contact with the upper belt-like body 42) is substantially equal to a sum of the following thicknesses: a thickness twice as large as that of the upper belt-like body 42 provided so as to be folded back at the time of wearing; a thickness corresponding to a distance between folded-back parts of the upper belt-like body 42; and a thickness of a bonded part (formed of an adhesive, for example) between the upper belt-like body 42 and the main-sheet portion 20. Thus, the thickness twice as large as that of the upper belt-like body 42, that is, the thickness of the folded-back upper belt-like body 42, contributes to the distance P. Specifically, the upper belt-like body 42 is structured to be folded back at the time of wearing so that the doubled parts are formed between the main-sheet portion 20 and the skin of the wearer. As a result, the distance P can be increased in comparison with that in a case where only an upper belt-like body that is not folded back exists between the main-sheet portion and the skin of the wearer or that in a case where the upper belt-like body does not exist between the main-sheet portion and the skin of the wearer. In this way, the floating state is easily achieved.

The above describes the distance P with reference to FIG. 24, but the same applies to the distance R. Specifically, the lower belt-like body 32 is structured to be folded back as well at the time of wearing so that the doubled parts are formed between the main-sheet portion 20 and the skin of the wearer. As a result, the distance R can be increased in comparison with that in a case where only an upper belt-like body that is not folded back exists between the main-sheet portion and the skin of the wearer or that in a case where the upper belt-like body does not exist between the main-sheet portion and the skin of the wearer. In this way, the floating state is easily achieved.

Each of the distances P and R is preferred to be 0.5 mm or more, and more preferred to be 1 mm or more. This is because, by setting the ranges of the distances P and R as described above, the floating state is easily achieved, and thus a shift is less liable to occur. Simultaneously, each of the distances P and R is preferred to be 10 mm or less, and more preferred to be 5 mm or less. This is because, by setting the ranges of the distances P and R as described above, a loose feel is prevented, and thus that excellent wearing comfort is obtained.

In order to set the ranges of the distances P and R as described above, there can be exemplified a method of setting the thicknesses of the upper belt-like body 42 and the lower belt-like body 32 to fall within particular ranges.

For example, when a stretchable film, a stretchable bandage obtained by forming an elastic yarn and a spun yarn into a net-like shape, and a laminated body formed by combination of those members and a non-woven fabric are used as the upper belt-like body 42 and the lower belt-like body 32, the upper belt-like body 42 and the lower belt-like body 32 normally have thicknesses of 0.5 mm or more when using commercially available products. Thus, with use of those products, the upper belt-like body 42 and the lower belt-like body 32 can doubly exist between the main-sheet portion 20 and the skin of the wearer. As a result, each of the distances P and R is easily set to 1 mm or more.

In addition, by coupling the upper belt-like body 42 and the lower belt-like body 32 under tension to the main-sheet portion 20 and then shrinking the same, peaks and valleys are formed. Also in this way, the distances P and R can be increased.

The lip portion of a normal mask is a part which is most easily tainted, and is also a part which should be kept cleanest. Thus, the distance Q is preferred to be 3 mm or more, and more preferred to be 5 mm or more. This is because, by setting the range of the distance Q as described above, the inner surface of the main-sheet portion is less liable to be tainted even when, for example, the wearer eats a throat lozenge, or keeps chewing gum or chocolate in his/her mouth. Further, even when the wearer talks while wearing lipstick, a lipstick mark is less liable to adhere to the main-sheet portion. Simultaneously, the distance Q is preferred to be 25 mm or less, and more preferred to be 20 mm or less. This is because, by setting the range of the distance Q as described above, a loose feel is prevented, and thus excellent wearing comfort is obtained.

The distance S is preferred to be 1 mm or more, and more preferred to be 2 mm or more. This is because, by setting the range of the distance S as described above, it is possible to suppress an inconvenience that the mouth touches the inner surface of the main-sheet portion during talking and the like. Simultaneously, the distance S is preferred to be 15 mm or less, and more preferred to be 10 mm or less. This is because, by setting the range of the distance S as described above, a loose feel is prevented, and thus excellent wearing comfort is obtained.

The relationship among the distances P, Q, R, and S is not particularly limited, but normally, the following relationship is established: $Q>S>P\approx R$.

The distances P, Q, R, and S are measured as follows.

Round holes are formed with a hollow punch (with a diameter of 5 mm) at positions on the main-sheet portion of the mask to be worn by the wearer, at which the distances P, Q, R, and S are to be measured. Next, a plastic round bar (with a diameter of 3 mm) provided with a length scale (0.5 mm unit) is inserted from an end portion thereof into the round holes, and the scale is read under a state in which the round bar is held in contact with positions on the skin of the wearer, at which the distances P, Q, R, and S are to be measured. Then, lengths of the inserted parts are to be measured. In addition, a thickness of the main-sheet portion is measured, and the measured thickness is subtracted from each of the lengths of the inserted parts. In this way, the distances P, Q, R, and S are calculated.

Note that, the scale is read in 0.5 mm units. When the inner surface of the main-sheet portion and the skin of the wearer is held in contact with each other, the length is 0 mm. The measurement is performed on a premise that an average (note that, rounded to 0.5 mm unit) of measured values of each of the distances P, Q, R, and S of at least four wearers is obtained as a value of each of the distances P, Q, R, and S.

The main-body portion 10 of the mask 100 according to the present invention may include other members than the main-sheet portion 20, the lower belt-like body 30, and the upper belt-like body 40.

For example, the main-body portion 10 includes the upper belt-like body 40 as illustrated in FIG. 1, but the mask according to the present invention may include, instead of the upper belt-like body, a tape member deformable in conformity with the shape of the nose of the wearer or a wire member deformable in conformity with the shape of the nose of the wearer, the tape member and the wire member being provided in the upper portion of the main-sheet portion. Those members can be used together with the upper belt-like body.

The tape member deformable in conformity with the shape of the nose of the wearer and the wire member deformable in conformity with the shape of the nose of the wearer are provided in the upper portion of the main-sheet portion. A protruding portion of the nose has a shape which greatly varies in height, and the nose tip is liable to be subjected to high tension, and hence gaps are liable to be formed at a root of the nose. The tape member and the wire member suppress formation of such gaps.

The tape member deformable in conformity with the shape of the nose of the wearer and the wire member deformable in conformity with the shape of the nose of the wearer are not particularly limited. For example, nose-fitting-type tape members and wire members used in conventional masks can be used. Specifically, a metal tape made of aluminum or the like and a rod made of a synthetic resin can be exemplified.

The fixation portions 90 of the mask 100 according to the present invention, which is illustrated in FIG. 1, are coupled to the main-body portion 10, and fix the main-body portion 10 to the lower face portion of the wearer.

Each of the fixation portions 90 is made of a looped stretchable material so as to be looped around each ear of the wearer. The stretchable material is not particularly limited, and an interwoven belt made of a rubber yarn and cotton, an interknitted net made of urethane filaments and polyester filaments, a woolly nylon knitted in a tubular shape, and a stretchable non-woven fabric can be exemplified.

In particular, as proposed in JP 6-328600 A and JP 7-252762 A by the inventor of the present invention, it is preferred to provide slits or cutouts to a composite elastic body having a uni-directional extensibility (for example, fixation portions 92 illustrated in FIGS. 21A and 21B). In addition, it is more preferred to provide slits or cutouts to a composite elastic body having a uni-directional extensibility, the composite elastic body being formed by laminating a non-woven fabric piece(s) on one or both surfaces of an elastomer film. In this case, the main-body portion can be stably fixed during wearing, and in addition, traces are less liable to be left on the skin of the wearer.

In the present invention, the materials for the fixation portions are not limited to the looped stretchable material. Specifically, the followings can be exemplified: two cords provided respectively on both the right and left sides of the main-body portion so as to be looped around the ears of the wearer by being tied to each other; structural bodies each designed like a temple of glasses so as to be hooked to the ears of the wearer from above; a looped headband to be looped around the head of the wearer, which is similar to that of an eye bandage; and a tackifier to be held in close contact with the cheeks of the wearer.

The mask 100 according to the present invention can be obtained by uniting the above-mentioned various members. A uniting method is not particularly limited, and the followings can be exemplified: sewing with use of a sewing thread and the like; adhesion by hot melting and the like; and welding by heat sealing, ultrasonic sealing, and the like. In a case of sewing with use of a sewing thread, sealing treatment with use of a resin, a tackifier tape, and the like can be performed to seams.

Description is made of functions and effects of the mask according to the present invention.

Figure 25:
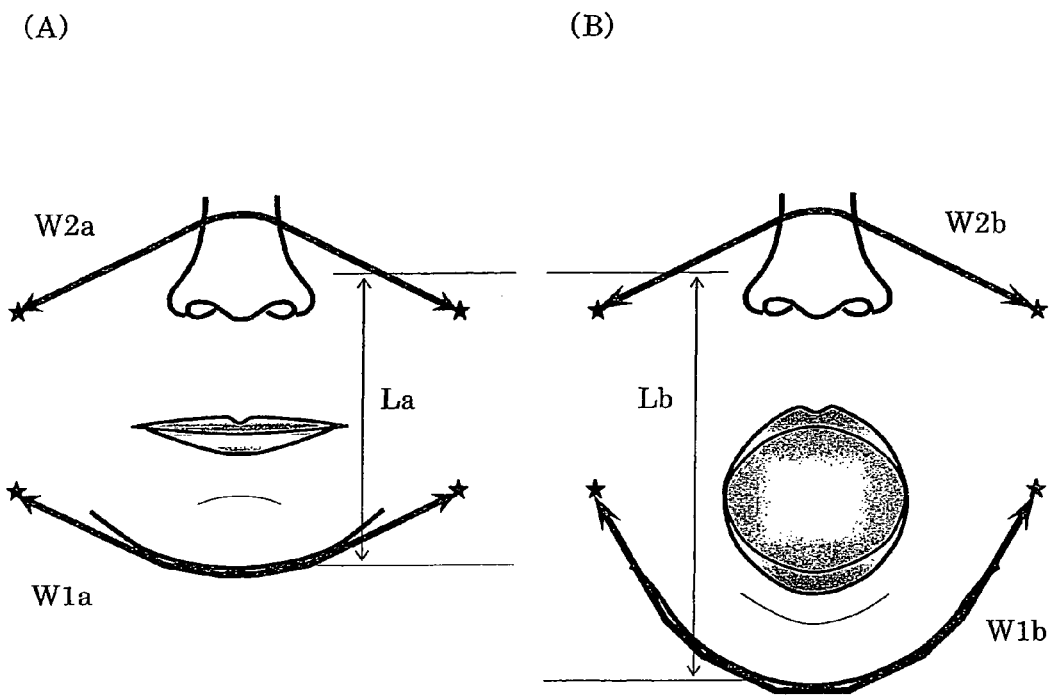
FIGS. 25A and 25B are schematic explanatory diagrams illustrating a dimensional change in accordance with movement of the face of the wearer of the mask.

FIGS. 25A and 25B are schematic explanatory diagrams illustrating a dimensional change of the mask in accordance with movement of the face of the wearer. FIG. 25A illustrates a state in which the wearer has his/her mouth closed, and FIG. 25B illustrates a state in which the wearer has his/her mouth open.

As illustrated in FIGS. 25A and 25B, when the mouth is vertically opened, a distance between the nose tip and a lower jaw end increases from La to Lb (difference therebetween is denoted by $\Delta L$), and a length between both the cheeks via the lower jaw end increases from W1a to W2b (difference therebetween is denoted by $\Delta W$). Meanwhile, a length between both the cheeks via a vicinity of the root of the nose slightly increases from W2a to W2b.

As described above, when the mouth is vertically opened, the distance between the nose tip and the lower jaw end increases by ΔL, and the length between both the cheeks via the lower jaw end increases by ΔW. Therefore, when the mask main body comes into contact with the nose tip and the lower jaw end or when the mask main body comes into contact from both the cheeks to the lower jaw end, those changes in distance have a significant influence on a wearing state of the mask. In the following, more specific description is made of the wearing state.

Figure 26:
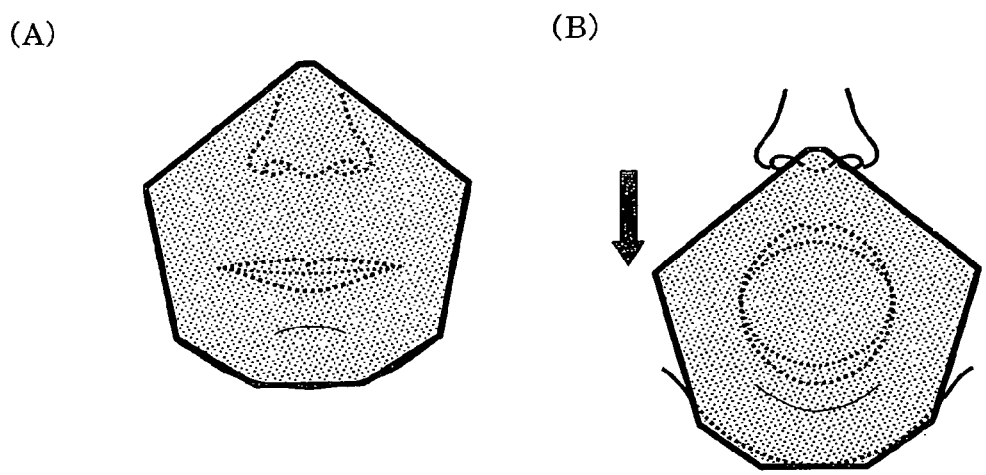
FIGS. 26A and 26B are schematic explanatory diagrams illustrating a change of a wearing state in accordance with movement of the face of a wearer of a conventionally well-known ultra three-dimensional mask.

FIGS. 26A and 26B are schematic explanatory diagrams illustrating a change of a wearing state of the conventionally well-known ultra three-dimensional mask in accordance with the movement of the face of the wearer. FIG. 26A illustrates a state in which the wearer has his/her mouth closed, and FIG. 26B illustrates a state in which the wearer has his/her mouth open. Note that, in FIGS. 26A and 26B, the main-body sheet portion of the ultra three-dimensional mask is indicated by half-tone dot meshing, and other portions are not illustrated.

As illustrated in FIGS. 26A and 26B, when the wearer has his/her mouth open, the main-body sheet portion of the ultra three-dimensional mask greatly shifts downward in accordance with movement of the jaw (as indicated by an arrow). This is because a jaw part of the main-body sheet portion of the ultra three-dimensional mask is held in firm contact with the face. When the wearer repeatedly has his/her mouth opened and closed, the shift repeatedly occurs, which may cause the main-body sheet portion to slip off from the nose in some cases.

Figure 27:
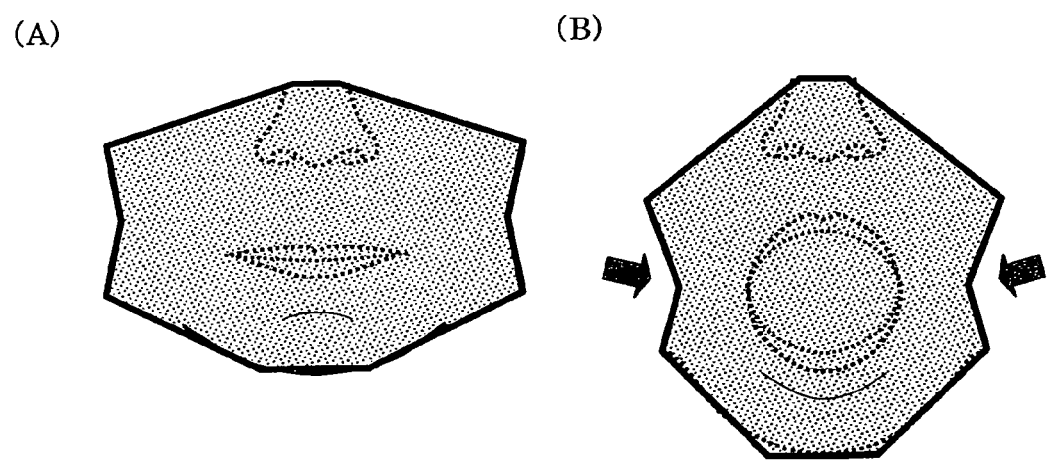
FIGS. 27A and 27B are schematic explanatory diagrams illustrating a change of a wearing state in accordance with movement of the face of a wearer of a conventionally well-known pleated mask.

FIGS. 27A and 27B are schematic explanatory diagrams illustrating a change of a wearing state of the conventionally well-known pleated mask in accordance with the movement of the face of the wearer. FIG. 27A illustrates a state in which the wearer has his/her mouth closed, and FIG. 27B illustrates a state in which the wearer has his/her mouth open. Note that, in FIGS. 27A and 27B, a main-body sheet portion of the pleated mask is indicated by half-tone dot meshing, and other portions are not illustrated.

As illustrated in FIGS. 27A and 27B, when the wearer has his/her mouth open, pleats of the main-body sheet portion of the pleated mask are unfolded, and exhibits a vertically extended shape. However, both right and left edge portions of the main-body sheet portion are pulled toward a center thereof, and large gaps are formed right and left thereof (as indicated by arrows). As a result, exhaled air leaks.

Figure 28:
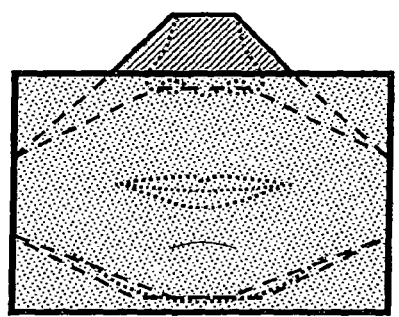
FIGS. 28A and 28B are schematic explanatory diagrams illustrating a change of a wearing state in accordance with movement of the face of a wearer of the mask according to the present invention.
Figure 28:
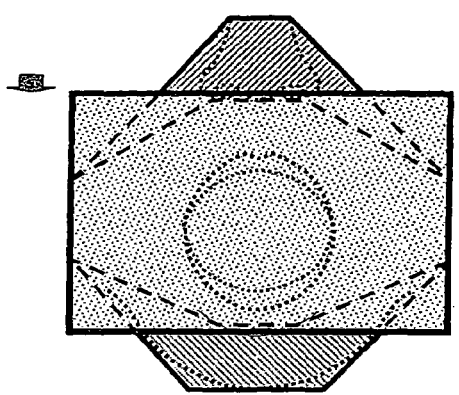

FIGS. 28A and 28B are schematic explanatory diagrams illustrating a change of the wearing state of the mask according to the present invention in accordance with movement of the face of the wearer. FIG. 28A illustrates a state in which the wearer has his/her mouth closed, and FIG. 28B illustrates a state in which the wearer has his/her mouth open. Note that, in FIGS. 28A and 28B, the main-sheet portion of the main-body portion of the mask according to the present invention is indicated by half-tone dot meshing, the lower belt-like body and the upper belt-like body of the main-body portion are indicated by shading, and other portions are not illustrated.

As illustrated in FIGS. 28A and 28B, when the wearer has his/her mouth open, the lower belt-like body of the mask according to the present invention, which accommodates the jaw of the wearer, extends to protrude downward with respect to the lower edge of the main-sheet portion. Thus, the main-sheet portion hardly shifts downward in accordance with the movement of the jaw (as indicated by an arrow). Further, exhaled air does not leak.

As described above, in the conventionally-well known masks, occurrence of a shift of the mask or leakage of exhaled air in accordance with the movement of the face of the wearer is inevitable. In contrast, the mask according to the present invention, the main-sheet portion does not shift or exhaled air does not leak even with the movement of the face of the wearer. This is because at least one of the lower belt-like body and the upper belt-like body is made of a belt-like stretchable material, and hence a stretchable effect of the stretchable material absorbs the movement of the face of the wearer and prevents the same from being transmitted to the main-sheet portion. This effect becomes more significant when the floating state is achieved.

Hereinabove, description has been made of the mask according to the present invention based on the illustrated embodiments, but the present invention is not limited to those embodiments. For example, the configuration of each portion can be replaced with an arbitrary configuration capable of exerting a similar function.

Further, the configurations of the portions according to the embodiments may be arbitrarily combined with each other so that another embodiment of the mask is carried out.

The mask according to the present invention is less liable to shift in wearing position, and hence can be suitably and variously used.

EXAMPLES

In the following, more detailed description is made of the present invention by way of examples. Note that, the present invention is not limited to those examples.

1. Manufacture of Mask

Example 1

Mode of Combining Nose Band and Jaw Wrapping Pocket with Each Other

Figure 30:
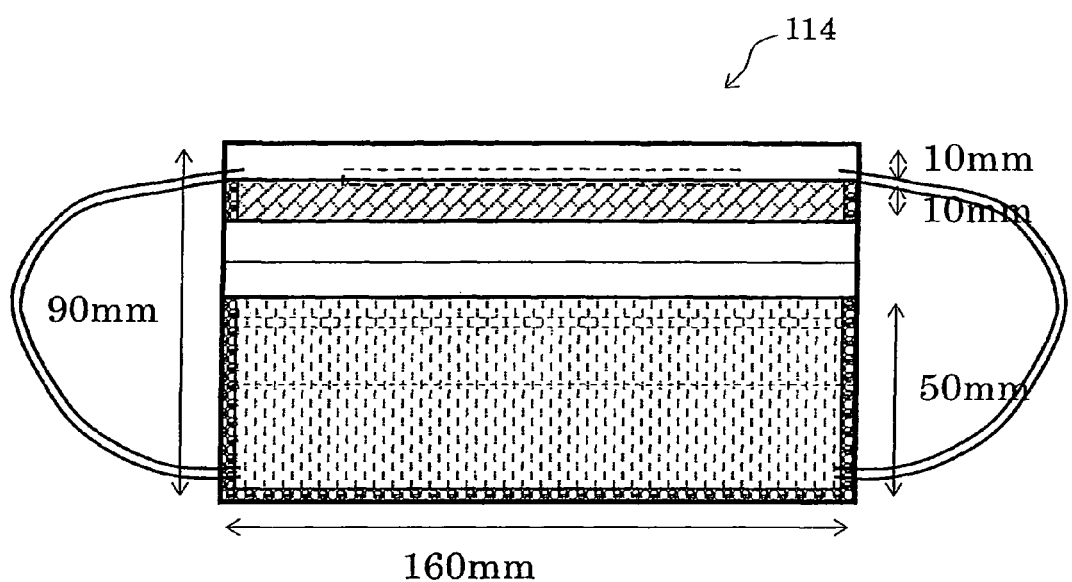
FIG. 30 is a schematic plan view of a mask obtained in Example 1.

A mask 114 illustrated in FIG. 30 was manufactured as described below. Note that, the mask 114 is substantially the same as the mask 106 illustrated in FIG. 5D except that a depth of the jaw wrapping pocket is large and a wire member deformable in conformity with the shape of the nose is provided. The mask 114 is sized as illustrated in FIG. 30.

Figure 31:
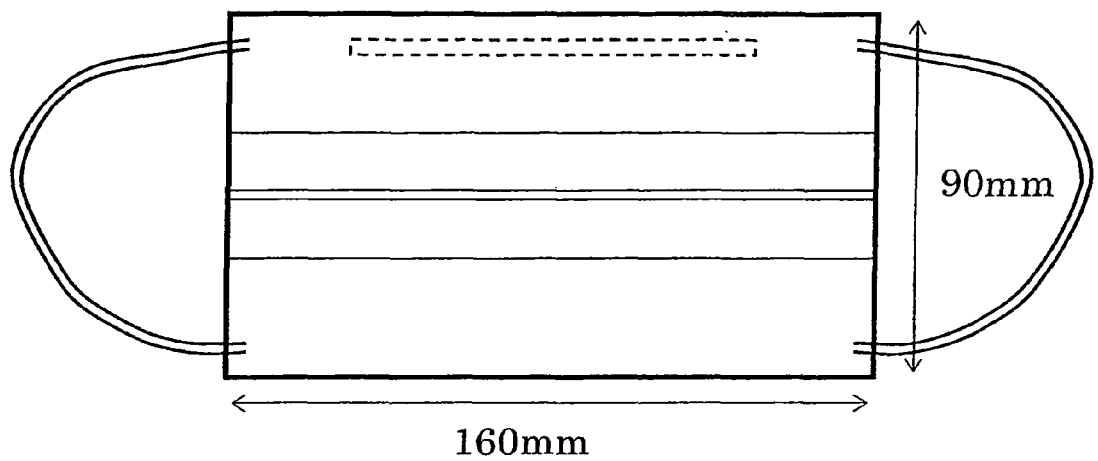
FIG. 31 is a schematic plan view of a commercially available pleated mask.

A commercially available pleated mask illustrated in FIG. 31 (Fitty 7 DAYS mask, manufactured by Tamagawa-Eizai Co., Ltd.) was prepared. This mask includes a wire member deformable in conformity with the shape of the nose, the wire member being provided near a center of an upper edge portion of a main-body sheet portion (illustrated by a dotted line in FIG. 31). The mask is sized as illustrated in FIG. 31.

The mask 114 was obtained by attaching a nose band made of a belt-like stretchable material (upper belt-like body) and a jaw wrapping pocket made of a belt-like stretchable material (lower belt-like body) to this commercially available pleated mask. The attachment was performed as follows.

The nose band was attached by coupling, with a rubber-based adhesive, both right and left ends of a rubber-yarn band out of tension to an inner surface of the main-body sheet portion of the commercially available pleated mask (corresponding to a main-sheet portion of the mask 114) so that an upper edge of the rubber-yarn band was positioned 10 mm below an upper edge of the main-body sheet portion, the rubber-yarn band having a width of 10 mm and obtained by interweaving a rubber yarn and a cotton yarn (pajama rubber, manufactured by FUJIHATO, with a breaking elongation of 210%).

Further, the jaw wrapping pocket having a depth of substantially 50 mm was attached to the commercially available pleated mask by coupling, with a rubber-based coupling agent, a lower edge and both right and left edges of a three-layer-structure stretchable composite body (KONPERA, manufactured by Japan Absorbent Technology Institute, with a breaking elongation of 270%) cut to have a width of 50 mm and extended by approximately 30% to the lower edge and both the right and left edges of the main-body sheet portion, the three-layer-structure stretchable composite body being obtained by heat-coupling a stretchable, spun-lace non-woven fabric (manufactured by UNITIKA Ltd., 50/50 mixed fiber of PE/PET: 1.5 d×51 mm and rayon: 2 d×51 mm, with a basis weight of 20 $g/m^2$) to both front and rear surfaces of a polyurethane film having a thickness of 30 µm.

Example 2

Mode of Combining Nose Band and Jaw Band with Each Other

Figure 32:
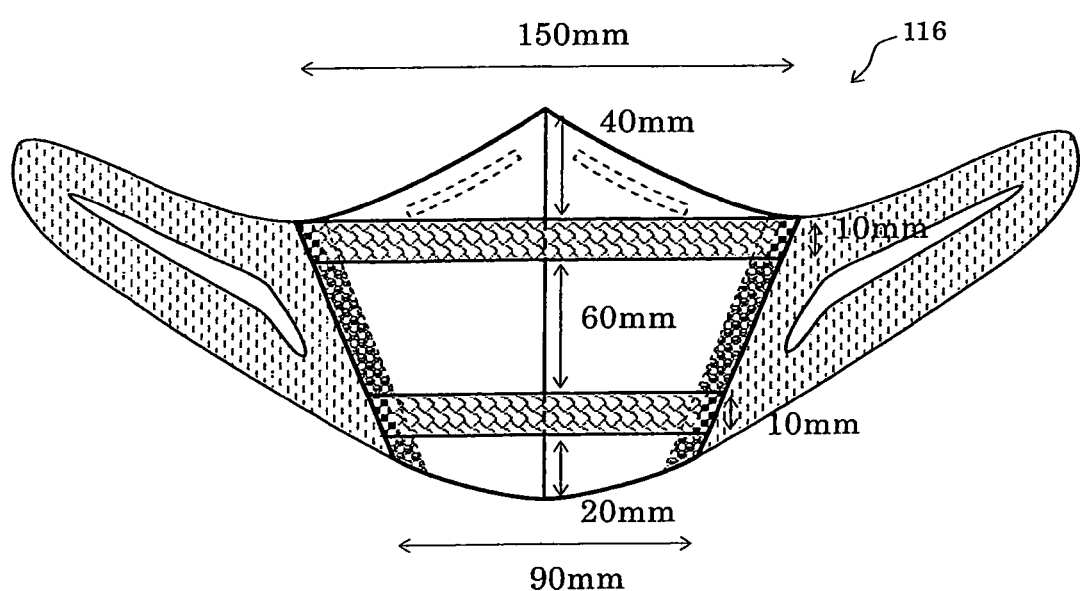
FIG. 32 is a schematic plan view of a mask obtained in Example 2.

A mask 116 illustrated in FIG. 32 was manufactured as described below. The mask 116 is sized as illustrated in FIG. 32.

Figure 33:
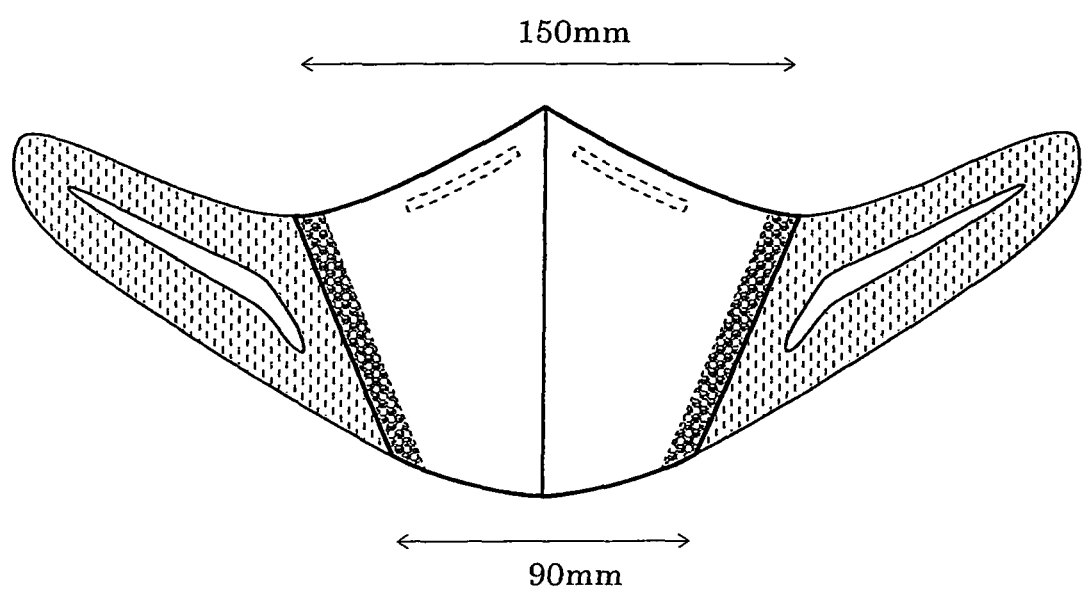
FIG. 33 is a schematic plan view of a commercially available ultra three-dimensional mask.

A commercially available ultra three-dimensional mask illustrated in FIG. 33 ("ultra three-dimensional virus guard, large size" mask manufactured by Unicharm Corporation) was prepared. This mask includes wire members deformable in conformity with the shape of the nose, the wire members being provided on right and left sides near a center of an upper edge portion of a main-body sheet portion (illustrated by dotted lines in FIG. 33). The mask is sized as illustrated in FIG. 33.

The mask 116 was obtained by attaching a nose band made of a belt-like stretchable material (upper belt-like body) and a jaw band made of a belt-like stretchable material (lower belt-like body) to this commercially available ultra three-dimensional mask. The attachment was performed as follows.

The nose band was attached by coupling, with a rubber-based adhesive, both right and left ends of a rubber-yarn band out of tension to an inner surface of the main-body sheet portion of the commercially available ultra three-dimensional mask (corresponding to a main-sheet portion of the mask 116) so that an upper edge of the rubber-yarn band was positioned 40 mm below a peak at a center of an upper edge of the main-body sheet portion, the rubber-yarn band having a width of 10 mm and obtained by interweaving a rubber yarn and a cotton yarn (pajama rubber, manufactured by FUJI-HATO, with a breaking elongation of 210%).

The jaw band was attached by coupling, with a rubber-based adhesive, both the right and left ends of the rubber-yarn band out of tension to the inner surface of the main-body sheet portion of the commercially available ultra three-dimensional mask so that a lower edge of the rubber-yarn band is positioned 20 mm above a peak at a center of a lower edge of the main-body sheet portion, the rubber-yarn band having a width of 10 mm and obtained by interweaving a rubber yarn and a cotton yarn (pajama rubber, manufactured by FUJI-HATO, with a breaking elongation of 210%).

Example 3

Mode of Combining Nose Wrapping Pocket and Jaw Band with Each Other

Figure 34:
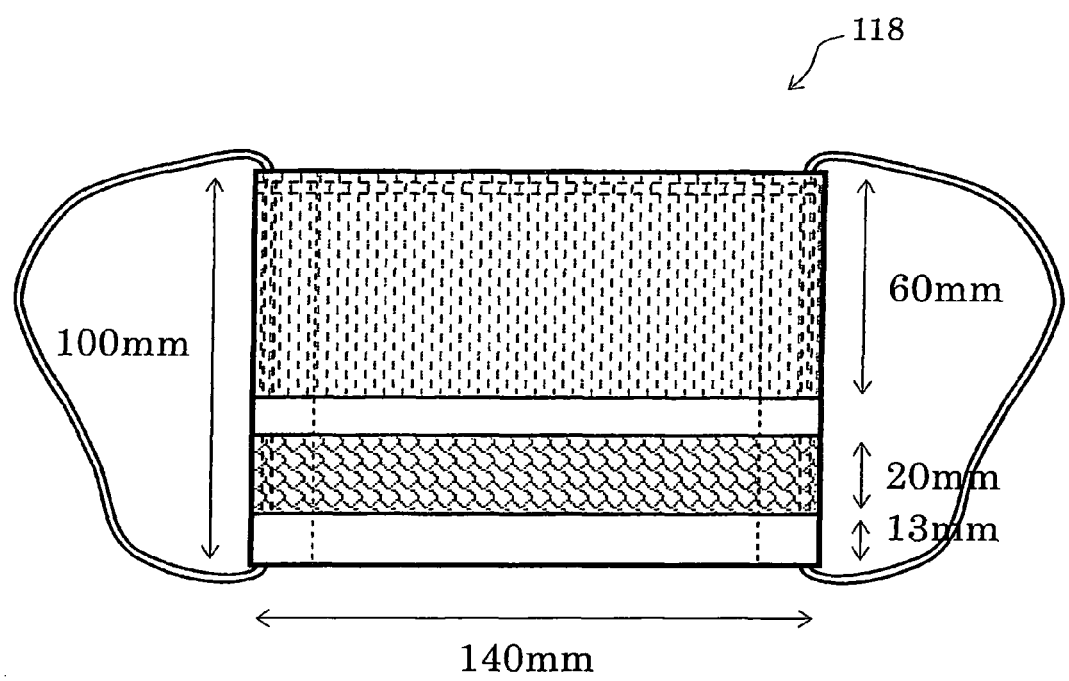
FIG. 34 is a schematic plan view of a mask obtained in Example 3.

A mask 118 illustrated in FIG. 34 was manufactured as described below. Note that, the mask 118 is substantially the same as the mask 104 illustrated in FIG. 5C except that a depth of the nose wrapping pocket is large. The mask 118 is sized as illustrated in FIG. 34.

Figure 35:
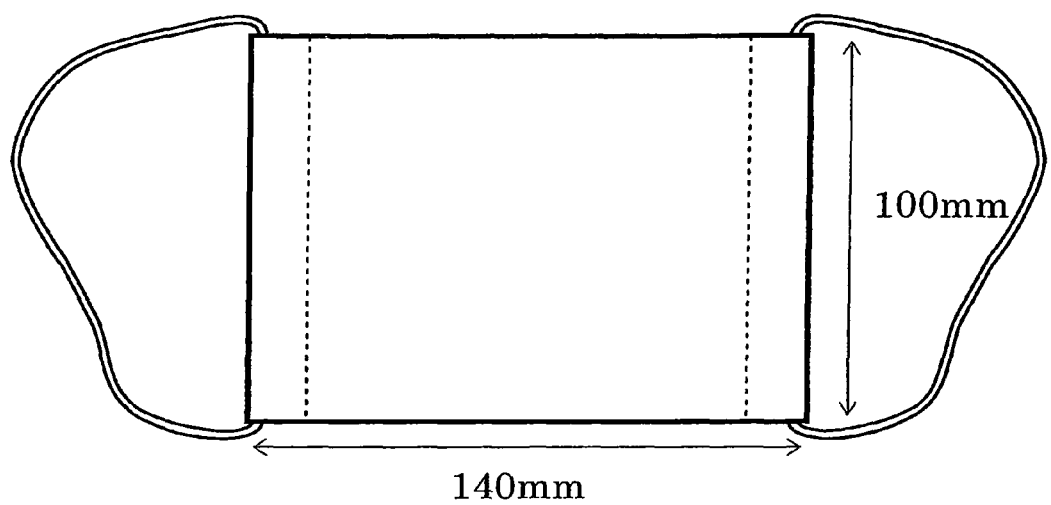
FIG. 35 is a schematic plan view of a commercially available gauze mask.

A commercially available gauze mask illustrated in FIG. 35 (air clean mask manufactured by Shirohato Co., Ltd.) was prepared. The mask is sized as illustrated in FIG. 35.

The mask 118 was obtained by attaching a nose wrapping pocket made of a belt-like stretchable material (upper belt-like body) and a jaw band made of a belt-like stretchable material (lower belt-like body) to this commercially available gauze mask. The attachment was performed as follows.

The nose wrapping pocket was attached by coupling, by sewing in double lines with a sewing machine, an upper edge and both right and left edges of a stretchable bandage out of tension to an upper edge and both right and left edges of an inner surface of a main-body sheet portion of the commercially available gauze mask (corresponding to a main-sheet portion of the mask 118), the stretchable bandage having a width of 60 mm (Antimicrobial SHINSHIKUTAI, manufactured by NICHIBAN CO., LTD., with a breaking elongation of 220%).

The jaw band was attached by coupling, by sewing in double lines with a sewing machine, both right and left edges of a stretchable tubular net bandage out of tension to both the right and left edges of the inner surface of the main-body sheet portion of the commercially available gauze mask so that a lower edge of the tubular net bandage was positioned 13 mm above a lower edge of the main-body sheet portion, the tubular net bandage having a diameter of 20 mm (One-touch net bandage, manufactured by Kowa Company, Ltd., with a breaking elongation of 150%).

Example 4

Mode of Combining Nose Wrapping Pocket and Jaw Wrapping Pocket (Including a Slit for Accommodating the Lower Jaw) with Each Other The mask 112 illustrated in FIG. 29 was manufactured as described below. The mask 112 is sized as illustrated in FIG. 29.

The mask 112 was obtained by attaching a nose wrapping pocket made of a belt-like stretchable material (upper belt-like body) and a jaw wrapping pocket including a slit for accommodating the lower jaw made of a belt-like stretchable material (lower belt-like body) to the commercially available gauze mask illustrated in FIG. 35. The attachment was performed as follows.

The nose wrapping pocket was attached by coupling, by sewing in double lines with a sewing machine, an upper edge and both right and left edges of a stretchable bandage out of tension to the upper edge and both the right and left edges of the inner surface of the main-body sheet portion of the commercially available gauze mask (corresponding to the main-sheet portion of the mask 112), the stretchable bandage having a width of 40 mm (Antimicrobial SHINSHIKUTAI, manufactured by NICHIBAN CO., LTD., with a breaking elongation of 220%).

The jaw wrapping pocket was attached by coupling, by sewing in double lines with a sewing machine, a lower edge and both right and left edges (note that, only lower 30 mm portion s) of a sheet of a tubular net bandage out of tension to a lower edge and both the right and left edges of the inner surface of the main-body sheet portion of the commercially available gauze mask, the sheet of the tubular net bandage ("Pupure," a cutting-type net bandage, manufactured by NISSIN MEDICAL INDUSTRIES CO., LTD.) being formed by cutting out the tubular net bandage that has been cut and opened into a planar shape so as to have a dimension of 40 mm long and 140 mm wide and being provided with a lateral slit having a length of 60 mm at a position 20 mm below the upper edge and at a central portion in the horizontal direction by cutting with use of a pair of scissors.

Example 5

Mode of Combining Nose Wrapping Pocket and Jaw Wrapping Pocket with Each Other

The mask 110 illustrated in FIG. 21 was manufactured as described below. The mask 110 is sized as illustrated in FIG. 21.

The main-sheet portion 20 was formed of a laminated body obtained by sandwiching a sheet (with a basis weight of 40 g/m$^2$), serving as a pathogen inactivating sheet, which was obtained by heat treatment of a web formed by mixing 3% of a silver-coated polyester fiber (Silfiber, manufactured by Mitsubishi Materials Corporation, 2 d×51 mm) with a PE/PET bicomponent fiber (manufactured by UNITIKA Ltd., 1.5 d×51 mm), between a PE non-woven fabric (DELNET, manufactured by SANSHO Co., Ltd., with a basis weight of 20 g/m$^2$), which formed the inner surface of the main-sheet portion 20, and an SMMS non-woven fabric (manufactured by Avgol Ltd., with a basis weight of 13 g/m$^2$), which was made of PP and formed the outer surface of the main-sheet portion 20. The main-sheet portion 20 had a horizontal length of 200 mm and a vertical length of 100 mm.

Each of the lower belt-like body 34 and the upper belt-like body 44 was formed of a stretchable body having a uni-directional extensibility (FlexAire 541 Elastic Laminate manufactured by Tredegar Corporation, with a basis weight of 95 g/m$^2$), which was a composite body obtained by sandwiching both surfaces of a synthetic rubber film with non-woven fabric pieces. This stretchable body was used by being cut on one side into a wave-like shape so as to have a horizontal length of 160 mm, a vertical length at both the right and left end portions of 60 mm, and a vertical length at the central portion of 40 mm.

One of the stretchable bodies was overlapped under a tension of 1.25 times onto the upper portion of the inner surface of the main-sheet portion 20, and the upper edge portion and both the right and left edge portions were coupled to the inner surface of the main-sheet portion 20 by heat sealing. In this way, the nose wrapping pocket (upper belt-like body 44) was formed. Next, another of the stretchable bodies was turned in the vertical direction and overlapped under a tension of 1.25 times onto the lower portion of the inner surface of the main-sheet portion 20 (partially overlapped onto the upper belt-like body 44). Then, the lower edge portion and both the right and left edge portions were coupled to the inner surface of the main-sheet portion 20 by heat sealing. In this way, the jaw wrapping pocket (lower belt-like body 34) was formed.

Further, each of the fixation portions 92 was formed of a stretchable body having a uni-directional extensibility (FlexAire 541 Elastic Laminate manufactured by Tredegar Corporation, with a basis weight of 95 g/m$^2$), which was a composite body obtained by sandwiching both surfaces of a synthetic rubber film with non-woven fabric pieces. The fixation portions 92 thus formed were each provided with an ear-loop cutout, and were attached by coupling respectively to both the right and left end portions of the main-body portion 11 by heat sealing.

Example 6

Mode of Including Nose Wrapping Pocket Formed of Bag-Like Member (#1)

As described below, the mask 108 illustrated in FIG. 12 was manufactured. The mask 108 is sized as illustrated in FIG. 12.

The mask 108 was obtained by attaching the nose-wrapping-pocket structural body 60 including the upper belt-like body 50 made of a belt-like stretchable material to the commercially available pleated mask illustrated in FIG. 31 as described below.

(1) Manufacture of Nose-Wrapping-Pocket Structural Body

The composite sheet 62 was prepared by laminating the PE/PP spun-bonded non-woven fabric (manufactured by Chisso Corporation, with a basis weight of 20 g/m$^2$) 62a and the LLD•PE film (manufactured by Tonen Chemical Corporation, with a thickness of 20 µm) 62b on each other. The composite sheet 62 was cut into a shape with the cutout as illustrated in FIG. 14A. The cutout part was provided for the purpose of facilitating inhalation and exhalation from the nose during wearing of the mask 108.

The stretchable composite sheet 64 was prepared by coupling, by heat fusion, the polyurethane film 64a having an isotropic stretchability in a planar direction (manufactured by Sheedom Co., Ltd., with a thickness of 25 µm) and the PE/PET spun-lace non-woven fabric 64b having a uni-directional stretchability in the horizontal direction (manufactured by UNITIKA Ltd., with a basis weight of 30 g/m$^2$) to each other. The breaking elongation of the stretchable composite sheet 64 was 190%. The stretchable composite sheet 64 had a shape as illustrated in FIG. 14B. The stretchable composite sheet 64 serves as the upper belt-like body 50 in the mask 108.

The nose-wrapping-pocket structural body 60 illustrated in FIGS. 13A and 13B was obtained by overlapping the composite sheet 62 and the stretchable composite sheet 64 prepared as described above on each other and coupling respective three sides thereof, that is, the upper edge and both the right and left edges, to each other by heat fusion.

As illustrated in FIG. 13B, the materials for the nose-wrapping-pocket structural body 60 were laminated in the following order from the inner side (upper side in FIG. 13B): the polyurethane film 64a; the PE/PET spun-lace non-woven fabric 64b; the PE/PP spun-bonded non-woven fabric 62a; and the LLD•PE film 62b.

(2) Attachment of Nose-Wrapping-Pocket Structural Body

The mask 108 was obtained by applying a tackifier to the surface of the LLD•PE film 62b of the nose-wrapping-pocket structural body 60 and applying the LLD•PE film 62b to the inner surface of the main-body sheet portion of the commercially available pleated mask (corresponding to the main-sheet portion 20 of the mask 108) at a position at which the nose-wrapping-pocket structural body 60 protrudes by 10 mm above the upper edge of the main-body sheet portion as illustrated in FIG. 12.

Example 7

Mode of Including Jaw Wrapping Pocket Formed of Bag-Like Member

As described below, the mask 109 illustrated in FIG. 15 was manufactured. The mask 19 is sized as illustrated in FIG. 15.

The mask 109 was obtained by attaching the jaw-wrapping-pocket structural body 80 including the lower belt-like body 70 made of a belt-like stretchable material to the commercially available pleated mask illustrated in FIG. 31 as described below.

(1) Manufacture of Jaw-Wrapping-Pocket Structural Body

The non-woven fabric sheet 82 was formed by cutting the gauze-like TCF non-woven fabric (#403,manufactured by FUTAMURA CHEMICAL CO., LTD., with a basis weight of 30 g/m$^2$) into the shape as illustrated in FIG. 17A. Under a state in which peeling tapes were attached, tackifier tapes for coupling the non-woven fabric sheet 82 to the main-body sheet portion of the commercially available pleated mask were provided to the parts of the outer surface of the non-woven fabric sheet 82, which were surrounded by dotted lines in FIG. 17A.

The stretchable composite sheet 84 was prepared by coupling, by heat fusion, the polyurethane film 84a having an isotropic stretchability in a planar direction (manufactured by Sheedom Co., Ltd., with a thickness of 25 μm) and the PE/PET spun-lace non-woven fabric 84b having a uni-directional stretchability in the horizontal direction (manufactured by UNITIKA Ltd., with a basis weight of 30 g/m$^2$) to each other. The breaking elongation of the stretchable composite sheet 84 was 190%. The stretchable composite sheet 84 had a shape as illustrated in FIG. 17B. The stretchable composite sheet 84 serves as the lower belt-like body 70 in the mask 109.

The jaw-wrapping-pocket structural body 80 illustrated in FIGS. 16A and 16B was obtained by overlapping the non-woven fabric sheet 82 and the stretchable composite sheet 84 prepared as described above on each other and coupling respective three sides thereof, that is, the lower edge and both the right and left edges, to each other with a hot melt adhesive.

As illustrated in FIG. 16B, the materials for the jaw-wrapping-pocket structural body 80 were laminated in the following order from the inner side (upper side in FIG. 16B): the polyurethane film 84a; the PE/PET spun-lace non-woven fabric 84b; and the non-woven fabric sheet (TCF non-woven fabric sheet) 82.

The isosceles triangular part in the upper portion of the jaw-wrapping-pocket structural body 80 illustrated in FIG. 16A is a part at which the stretchable composite sheet 84 does not exist and the non-woven fabric sheet 82 is exposed, and corresponds to a part to be brought into contact with the lips of the wearer in the mask 109.

(2) Attachment of Jaw-Wrapping-Pocket Structural Body

The mask 109 was obtained by peeling the peeling tape from each of the tackifier tapes on the non-woven fabric sheet 82 of the jaw-wrapping-pocket structural body 80 and applying the non-woven fabric sheet 82 to the inner surface of the main-body sheet portion of the commercially available pleated mask (corresponding to the main-sheet portion 20 of the mask 109) at a position at which the jaw-wrapping-pocket structural body 80 protrudes by 10 mm below the lower edge of the main-body sheet portion as illustrated in FIG. 15.

Example 8

Mode of Including Nose Wrapping Pocket Formed of Bag-Like Member (#2)

As described below, a mask 120 illustrated in FIG. 36 was manufactured.

Figure 37:
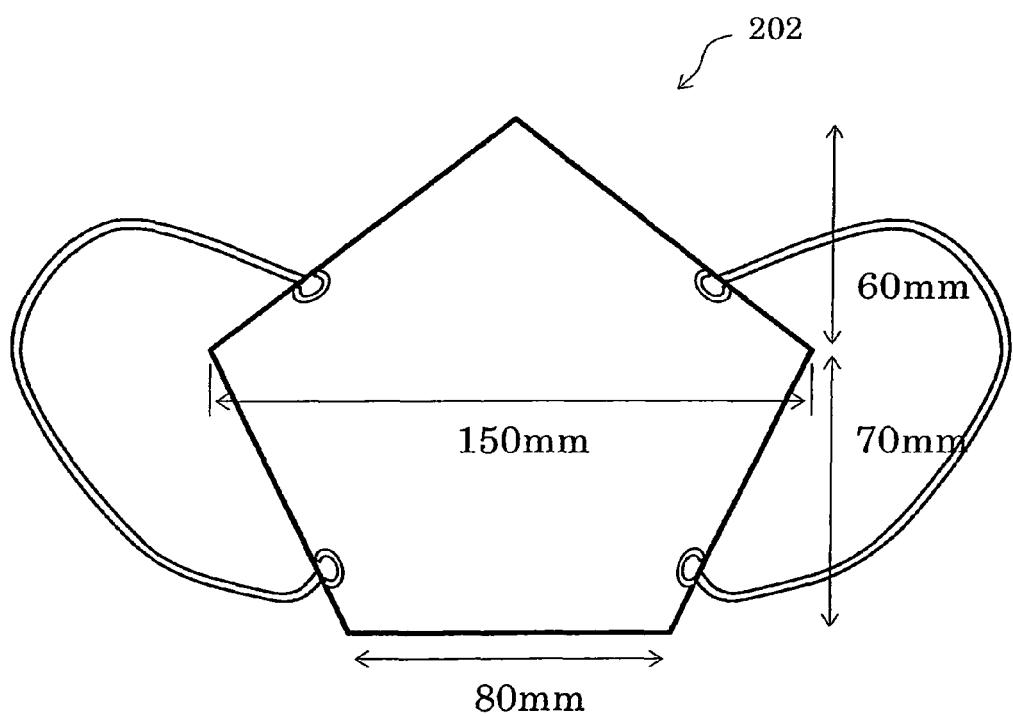
FIG. 37 is a schematic plan view of a mask free from a nose-wrapping-pocket structural body used for manufacturing the mask of Example 8.

First, a mask 202 illustrated in FIG. 37 was manufactured by coupling rubber-cord ear hooks (corresponding to fixation portions 91 of the mask 120) respectively to the left and right of a main-body sheet portion having a pentagonal shape illustrated in FIG. 37 and made of the same material as that for the main-sheet portion 20 in Example 5 (corresponding to a main-sheet portion 22 of the mask 120). The mask 202 is sized as illustrated in FIG. 37.

The mask 120 was obtained by attaching a nose-wrapping-pocket structural body 61 including an upper belt-like body 52 made of a belt-like stretchable material to the mask 202 illustrated in FIG. 37 as described below.

(1) Manufacture of Nose-Wrapping-Pocket Structural Body

Figure 39:
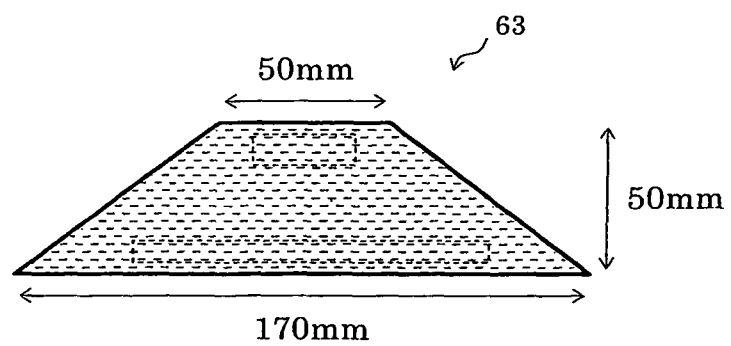
FIGS. 39A and 39B are schematic plan views respectively illustrating a PE/PP spun-bonded non-woven fabric and a stretchable composite sheet forming the nose-wrapping-pocket structural body used for manufacturing the mask of Example 8.
Figure 39:
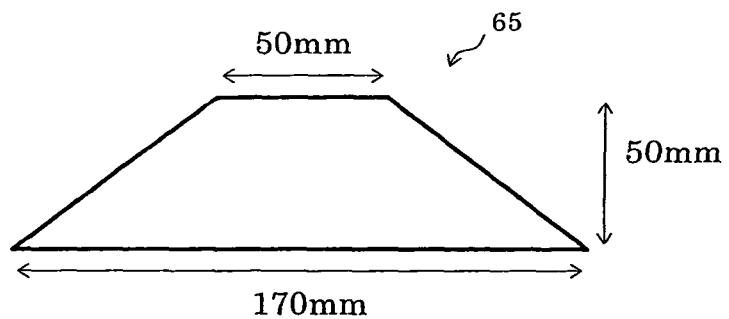

A PE/PET spun-bonded non-woven fabric (manufactured by UNITIKA Ltd., with a basis weight of 20 g/m$^2$) 63 was cut into the shape as illustrated in FIG. 39A. Under a state in which peeling tapes were attached, tackifier tapes for coupling the PE/PET spun-bonded non-woven fabric 63 to the main-body sheet portion of the mask 202 were provided to the parts of an outer surface of the PE/PET spun-bonded non-woven fabric 63, which were surrounded by dotted lines in FIG. 39A.

Next, a stretchable composite sheet 65 was prepared, which was made of the same material as that of the stretchable composite sheet 84 in Example 7 and had a shape illustrated in FIG. 39B. The stretchable composite sheet 65 serves as the upper belt-like body 52 in the mask 120.

Figure 38:
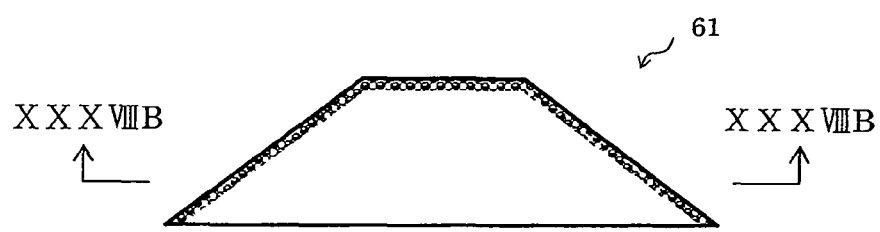
FIGS. 38A and 38B are schematic views of a nose-wrapping-pocket structural body including an upper belt-like body used for manufacturing the mask of Example 8.
Figure 38:
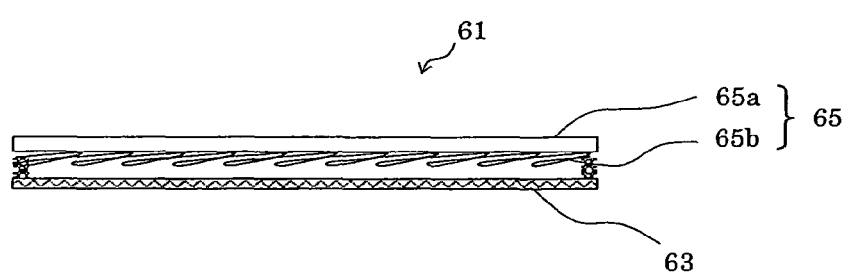

The nose-wrapping-pocket structural body 61 illustrated in FIGS. 38A and 38B was obtained by overlapping the PE/PET spun-bonded non-woven fabric 63 and the stretchable composite sheet 65 prepared as described above on each other and coupling respective three sides thereof, that is, the upper edge and both the right and left edges, to each other by heat fusion. Note that, with regard to FIGS. 38A and 38B, FIG. 38A is a plan view, and FIG. 38B is a lateral sectional view taken along the line XXXVIIIB-XXXVIIIB of FIG. 38A.

As illustrated in FIG. 38B, the materials for the nose-wrapping-pocket structural body 61 were laminated in the following order from the inner side (upper side in FIG. 38B): a polyurethane film 65a; a PE/PET spun-lace non-woven fabric 65b; and the PE/PET spun-bonded non-woven fabric 63.

(2) Attachment of Nose-Wrapping-Pocket Structural Body

Figure 36:
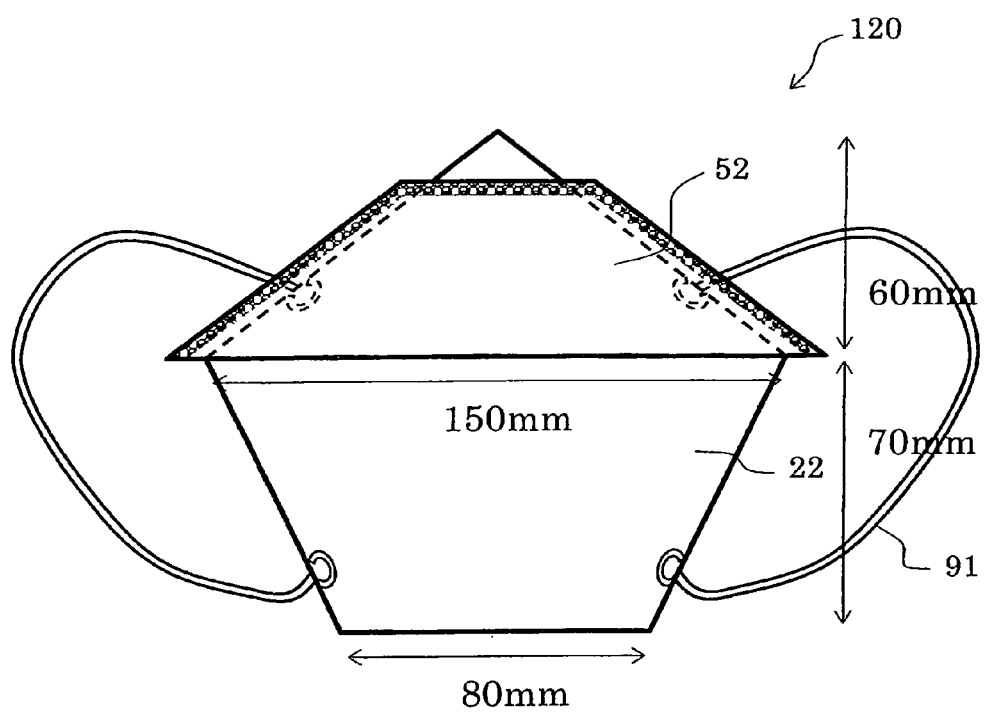
FIG. 36 is a schematic plan view of a mask obtained in Example 8.

The mask 120 was obtained by peeling the peeling tape from each of the tackifier tapes on the PE/PET spun-bonded non-woven fabric 63 of the nose-wrapping-pocket structural body 61 and applying the PE/PET spun-bonded non-woven fabric 63 to the inner surface of the main-body sheet portion of the mask 202 at a position at which the nose-wrapping-pocket structural body 61 extended to protrude slightly from both the right and left edges of the upper portion of the main-body sheet portion as illustrated in FIG. 36.

2. Evaluation of Masks (1) Evaluation of Mask of Example 1

Wearing states of the mask obtained in Example 1 and the commercially available pleated mask illustrated in FIG. 31, which did not have any upper or lower belt-like body attached thereto, were evaluated after the masks were worn by two men and two women (four persons in total).

Evaluation items and results are shown in Table 2. Note that, the measurement of the inner-mask-space distance was performed in 0.5 mm units, and an average (rounded to 0.5 mm unit) of distance values measured on the four wearers was calculated as the inner-mask-space distance (hereinafter, the same applies).

TABLE 2

| Evaluation item | Commercially available pleated mask | Mask of Example 1 |
| --- | --- | --- |
| Inner-mask-space distance (P:Q:R:S from the left, in units of mm) and relation with faces of wearers | 0.0:0.0:0.0:0.0 The inner surface of the main body was held in contact with the face as a whole. | 1.5:4.0:2.0:2.5 A state of floating as a whole was observed. |
| Positional shift of mask in accordance with opening and closing of the mouth | Folds of the pleats were unfolded in accordance with opening and closing of the mouth, and then kept unfolded. Flapping motion around the mouth was observed. | An original state was maintained without involving a shift of the mask or unfolding of the pleats. |
| Formation of gaps which may cause leakage of exhaled air | Tunnel-like gaps were formed at central parts of both the cheeks. Although the nose part was pressed with a nose fitter (wire member), gaps were formed near the wings of the nose. Although the lower jaw was held in contact with the mask, gaps were partially formed. | The originally-attached nose fitter functioned from above the nose band, and formation of the gaps at the nose part was hardly observed. The lower jaw was completely covered with the jaw wrapping pocket, and hence gaps were not formed. |

(2) Evaluation of Mask of Example 2

Wearing states of the mask obtained in Example 2 and the commercially available ultra three-dimensional mask illustrated in FIG. 33, which did not have any upper or lower belt-like body attached thereto, were evaluated after the masks were worn by two men and two women (four persons in total).

Evaluation items and results are shown in Table 3.

TABLE 3

| Evaluation item | Commercially available ultra three-dimensional mask | Mask of Example 2 |
| --- | --- | --- |
| Inner-mask-space distance (P:Q:R:S from the left, in units of mm) and relation with faces of wearers | 0.0:12.5:0.0:0.5 The mask was in close contact with the nose, the jaw, and both the cheeks except the lip part. | 1.5:15.0:1.5:2.5 The mask clearly floated as a whole. |
| Positional shift of mask in accordance with opening and closing of the mouth | The mask immediately shifted downward in accordance with opening and closing of the mouth, and slipped off from the nose as a result of repeated opening and closing of the mouth. | Although vibrating up and down in accordance with opening and closing of the mouth, the mask remained as it was at the original position without shifting. |

(3) Evaluation of Mask of Example 3

Wearing states of the mask obtained in Example 3 and the commercially available gauze mask illustrated in FIG. 35, which did not have any upper or lower belt-like body attached thereto, were evaluated after the masks were worn by two men and two women (four persons in total).

Evaluation items and results are shown in Table 4.

TABLE 4

| Evaluation item | Commercially available gauze mask | Mask of Example 3 |
| --- | --- | --- |
| Inner-mask-space distance (P:Q:R:S from the left, in units of mm) and relation with faces of wearers | 0.0:0.0:0.0:0.0 The inner surface of the mask was entirely held in contact with the face. | 1.5:3.0:1.0:2.0 Although the mask was partially held in contact with the central part of the jaw, other parts of the mask floated. |
| Contact state with respect to lip part | The mask was in close contact with the lip part, and hence was easily tainted. As for the women, a lipstick mark adhered. | Owing to existence of the inner-mask space, a lipstick mark and the like did not adhere. |
| Positional shift of mask in accordance with opening and closing of the mouth | Although the mask did not slip off, the mask moved in accordance with opening and closing of the mouth. | The position of the mask did not change even with opening and closing of the mouth. |

(4) Evaluation of Mask of Example 4

Wearing states of the mask obtained in Example 4 and the commercially available gauze mask illustrated in FIG. 35, which did not have any upper or lower belt-like body attached thereto, were evaluated after the masks were worn by two men and two women (four persons in total). Note that, the mask in Example 4 was worn with the leading end of the lower jaw of the wearer inserted into the slit 36a.

Evaluation items and results are shown in Table 5.

TABLE 5

| Evaluation item | Commercially available gauze mask | Mask of Example 4 |
| --- | --- | --- |
| Inner-mask-space distance (P:Q:R:S from the left, in units of mm) and relation with faces of wearers | 0.0:0.0:0.0:0.0 The inner surface of the mask was entirely held in contact with the face. | 1.5:3.0:2.0:1.5 The mask substantially entirely floated. |
| Contact state with respect to lip part | The mask was in close contact with the lip part, and hence was easily tainted. As for the women, a lipstick mark adhered. | Owing to existence of the inner-mask space, a lipstick mark and the like did not adhere. |
| Positional shift of mask in accordance with opening and closing of the mouth | Although the mask did not slip off, the mask moved in accordance with opening and closing of the mouth. | The position of the mask did not change even with opening and closing of the mouth. |

(5) Evaluation of Mask of Example 5

Wearing states of the mask obtained in Example 5 were evaluated after the mask was worn by two men and two women (four persons in total).

Evaluation items and results are shown in Table 6.

TABLE 6

| Evaluation item | Mask of Example 5 |
| --- | --- |
| Inner-mask-space distance (P:Q:R:S from the left, in | 2.0:12.0:4.0:6.0 The mask substantially entirely |

TABLE 6-continued

| Evaluation item | Mask of Example 5 |
|---|---|
| units of mm) and relation with faces of wearers | floated. |
| Contact state with respect to lip part | Owing to existence of the inner-mask space, a lipstick mark and the like did not adhere. |
| Positional shift of mask in accordance with opening and closing of the mouth | The position of the mask did not change even with opening and closing of the mouth. |
| Formation of gaps which may cause leakage of exhaled air | The nose part and the lower jaw were completely covered with the wrapping pockets, and hence gaps were not formed. |

(6) Evaluation of Mask of Example 6

Generation states of glasses fogging of the mask obtained in Example 6 and the commercially available pleated mask illustrated in FIG. 31, which did not have any nose-wrapping-pocket structural body attached thereto, were evaluated after the masks were worn by two men and two women (four persons in total), who always wore glasses.

As a result, the glasses were fogged approximately in twenty seconds on average after the commercially available pleated mask was worn, but the glasses were not fogged even in fifteen minutes after the mask of Example 6 was worn.

In addition, the mask of Example 6 did not shift even slightly.

(7) Evaluation of Mask of Example 7

The mask obtained in Example 7 and the commercially available pleated mask illustrated in FIG. 31, which did not have any jaw-wrapping-pocket structural body attached thereto, were evaluated in the following manner after the masks were worn by four women.

Before wearing the masks, each of the wearers heavily wore lipstick, and held a cracker in her mouth.

For three minutes after the mask was worn, each of the wearers kept wearing the mask while calmly breathing, and for next two minutes, kept moving her mouth while crunching the cracker. For three minutes thereafter, each of the wearers kept wearing the mask while calmly breathing again, and then took off the mask. After that, as for the mask of Example 7, the jaw-wrapping-pocket structural body 80 was detached from the main-sheet portion 20.

As a result, a lipstick mark thickly adhered and powder of the cracker also adhered over the range of approximately 50 mm long and approximately 60 mm wide of each of all the commercially available pleated masks worn by the wearers. In contrast, motion at the main-sheet portion 20 of the mask of Example 7 was small, and the main-sheet portion 20 floated. Thus, the lipstick mark adhered within a small range of approximately 30 mm long and 40 mm wide, and only a small amount of powder of the cracker adhered.

Further, as a result of observation of the inner surface of the main-sheet portion 20 under a state in which the jaw-wrapping-pocket structural body 80 was detached, dirt except adhesion marks of the tackifier was not found.

(8) Evaluation of Mask of Example 8

Wearing states of the mask obtained in Example 8 and the mask 202 illustrated in FIG. 37, which did not have any nose-wrapping-pocket structural body attached thereto, were evaluated after the masks were worn by two men and two women (four persons in total).

Evaluation items and results are shown in Table 7.

TABLE 7

| Evaluation item | Mask 202 | Mask of Example 8 |
|---|---|---|
| Formation state of gaps during wearing at: | | |
| Nose portion | Large gaps were formed on both sides of the nose. | The nose was completely covered with the bag. |
| Lower jaw portion | Small gaps were formed. | Small gaps were formed. |
| Both cheek portions | Small gaps were formed. | Small gaps were formed. |
| Occurrence of shift by moving the mouth ten times | The masks slipped off from the nose of each of all the wearers by the time the mouth moved ten times, and shifted toward the lower jaw. | Although moving slightly up and down by being pulled toward the jaw, the masks did not slip off from the nose of each of all the wearers. |
| Leakage state of exhaled air during wearing for ten minutes | Exhaled air leaked with a hissing sound from both sides of the nose. | Leakage from the nose was not observed, and slight leakage from both cheek parts was observed. |

The nose-wrapping-pocket structural body 61 and the main-sheet portion 22 of the mask of Example 8 are coupled to each other with a tackifier applied at the two points. In this context, when coupling is performed only with the upper tackifier part so that the nose-wrapping-pocket structural body 61 can move in a wider range, the mask of Example 8 can be worn, with the upper belt-like body covering the nose of the wearer in a cap-like manner without being folded back.

The invention claimed is:

1. A mask, including:
   a main-body portion for covering a lower face portion of a wearer including a nose and a mouth; and
   at least one fixation portion for fixing the main-body portion to the lower face portion of the wearer, the at least one fixation portion being coupled to the main-body portion,
   wherein the main-body portion includes:
   a main-sheet portion; and
   a lower belt for holding a lower jaw below a chin area of the wearer, the lower belt being made of a stretchable material and provided across both right and left end portions of the main-sheet portion in a lower portion on an inner side of the main-sheet portion, the lower belt being coupled with the main-sheet portion at a lower marginal portion of the lower belt, the lower belt being folded back downward and toward the lower jaw below the chin area of the wearer at a position above a coupling position where the lower belt is coupled with the main-sheet portion, and an upper belt for holding the nose of the wearer, the upper belt being made of a stretchable material and provided across both the right and left end portions of the main-sheet portion in an upper portion on the inner side of the main-sheet portion, the upper belt being coupled with the main-sheet portion at an upper marginal portion of the upper belt, the upper belt being folded back upward and toward the nose of the wearer at a position which is below the nose of the wearer and below a coupling position where the upper belt is coupled with the main-sheet portion, wherein at the upper marginal portion of the upper belt, the upper belt is coupled with the main-sheet portion by an adhesive, and at the position where the upper belt is folded back upward and toward the nose of the wearer, the upper belt is not coupled with the main-sheet portion and is spaced apart from the main-sheet portion, a portion of the upper belt which is folded back upward from the position covering an entire nose of the wearer.

2. The mask according to claim 1,
wherein the lower belt and the upper belt is configured to be positioned between the main-sheet portion and skin of the wearer during wearing.

3. The mask according to claim 2,
wherein the lower belt is configured to be held in contact with a face of the wearer, covering a region of the face of the wearer from the lower jaw to both cheeks via a jawbone; and the upper belt is configured to be held in contact with the face of the wearer, covering a region of the face of the wearer from a nose tip to both the cheeks via wings of the nose.

4. The mask according to claim 1,
wherein an inner surface of the main-sheet portion is configured to be out of contact from the skin of the wearer during wearing.

5. The mask according to claim 4,
wherein, during wearing, a shortest distance between the inner surface of the main-sheet portion and a horizontally central, lowermost portion of a part of the nose of the wearer which comes into contact with the main-body portion is 0.5 mm or more.

6. The mask according to claim 4,
wherein, during wearing, a distance between the inner surface of the main-sheet portion and a horizontally central, lowermost portion of an upper lip of the wearer is 3 mm or more.

7. The mask according to claim 4,
wherein, during wearing, a shortest distance between the inner surface of the main-sheet portion and a horizontally central, uppermost portion of a part of a jaw of the wearer which comes into contact with the main-body portion is 0.5 mm or more.

8. The mask according to claim 4,
wherein, during wearing, a distance between the inner surface of the main-sheet portion and a cheek of the wearer is 1 mm or more.

9. The mask according to claim 1,
wherein a maximum stretching rate in a horizontal direction of the at least one of the lower belt and the upper belt is 1.5 or more.

10. The mask according to claim 1,
wherein the main-body portion includes the lower belt, and the lower belt is configured so that an entire lower marginal portion thereof is not coupled to the main-sheet portion and forms a stretchable jaw band to be caught by the lower jaw of the wearer.

11. The mask according to claim 1,
wherein the main-body portion includes the lower belt, and the lower belt is configured so that an entire lower marginal portion or a part of the lower marginal portion thereof is coupled to the main-sheet portion and forms a jaw wrapping pocket for accommodating the lower jaw of the wearer.

12. The mask according to claim 11,
wherein the lower belt is folded back so that a doubled part is formed between the main-sheet portion and the skin of the wearer during wearing.

13. The mask according to claim 11,
wherein a depth of the jaw wrapping pocket is 20 mm or more.

14. The mask according to claim 1,
wherein the main-body portion includes the lower belt, and a jaw wrapping pocket for accommodating the lower jaw of the wearer is formed of a bag-like member having an opening provided on an upper side thereof, the bag-like member being obtained by coupling the lower belt and a sheet-like object, which is provided on an outer side of the lower belt, to each other at lower edge portions and both right and left sides thereof, the bag-like member being coupled to the main-sheet portion at a portion of the sheet-like object so that the lower belt is positioned in a lower portion on the inner side of the main-sheet portion.

15. The mask according to claim 1,
wherein the main-body portion includes the lower belt, and the lower belt includes a slit or a hole so that the lower jaw of the wearer is accommodated in the slit or the hole.

16. The mask according to claim 1,
wherein the main-body portion includes the upper belt, and the upper belt is configured so that an entire upper marginal portion thereof is not coupled to the main-sheet portion and forms a stretchable nose band to be caught by the nose of the wearer.

17. The mask according to claim 1,
wherein the main-body portion includes the upper belt, and the upper belt is configured so that an entire upper marginal portion or a part of the upper marginal portion thereof is coupled to the main-sheet portion and forms a nose wrapping pocket for accommodating the nose of the wearer.

18. The mask according to claim 17,
wherein the upper belt is folded back so that a doubled part is formed between the main-sheet portion and the skin of the wearer during wearing.

19. The mask according to claim 17,
wherein a depth of the nose wrapping pocket is 20 mm or more.

20. The mask according to claim 1,
wherein the main-body portion includes the upper belt, and a nose wrapping pocket for accommodating the nose of the wearer is formed of a bag-like member having an opening provided on a lower side thereof, the bag-like member being obtained by coupling the upper belt and a sheet-like object, which is provided on an outer side of the upper belt, to each other at upper edge portions and both right and left sides thereof, the bag-like member being coupled to the main-sheet portion at a portion of the sheet-like object so that the upper belt is positioned in an upper portion on the inner side of the main-sheet portion.

* * * * *